United States Patent
Sharma et al.

(10) Patent No.: US 6,946,491 B2
(45) Date of Patent: Sep. 20, 2005

(54) COMPOUNDS FOR THE TREATMENT OF METABOLIC DISORDERS

(75) Inventors: Shalini Sharma, Gaithersburg, MD (US); Reid W. von Borstel, Potomac, MD (US)

(73) Assignee: Wellstat Therapeutics Corporation, Gaithersburg, MD (US)

(*) Notice: Subject to any disclaimer, the term of this patent is extended or adjusted under 35 U.S.C. 154(b) by 0 days.

(21) Appl. No.: 10/685,183

(22) Filed: Oct. 14, 2003

(65) Prior Publication Data

US 2004/0092516 A1 May 13, 2004

Related U.S. Application Data

(62) Division of application No. 10/167,839, filed on Jun. 12, 2002.
(60) Provisional application No. 60/297,282, filed on Jun. 12, 2001.

(51) Int. Cl.[7] .................. A61K 31/135; A61K 31/12; A61K 31/075
(52) U.S. Cl. .................. 514/649; 514/675; 514/678; 514/717; 560/8; 560/19; 560/38; 560/39; 560/75; 560/205; 564/123; 564/149
(58) Field of Search ................ 514/649, 675, 514/678, 717; 560/8, 19, 38, 39, 75, 205; 564/123, 149

(56) References Cited

U.S. PATENT DOCUMENTS

| 4,011,321 A | 3/1977 | Coates et al. |
| 4,098,816 A | 7/1978 | Thorne et al. ............ 562/473 |
| 4,638,094 A | 1/1987 | Nakai et al. ............. 568/309 |
| 4,845,231 A | 7/1989 | Kees |
| 5,817,693 A | 10/1998 | Cousins et al. |
| 5,948,803 A | 9/1999 | Maeda et al. |
| 6,555,536 B2 | 4/2003 | Burris et al. ............ 514/230.5 |

FOREIGN PATENT DOCUMENTS

| BE | 667498 | * 11/1965 |
| BR | 9802163 | 11/2000 |
| DE | 1929165 | 12/1969 |
| DE | 2 309 986 | 8/1974 |
| DE | 2459468 | 7/1975 |
| DE | 2512673 | 10/1975 |
| DE | 2527066 | 1/1976 |

(Continued)

OTHER PUBLICATIONS

Chem ikcal Abstract DN 111:108486.*
Chemical Abstract DN 132:22755, also cited as WO 9962520.*
Chemical Abstract DN 111:108486, also cited as Kameo et al in Chem. & Phar. Bull. 37/5, 1260–7(1989).*
Chemical Abstract DN 65:20620 also cited as Carlo et al BE 667498.*
Chemical Abstract DN 128: 154084, also cited as Momose et al WO 9803508.*
Chemical Abstract DN 120: 134060, also cited as Sato et al JP05230009.*
Chemical Abstract DN 82: 124990, also cited as Franke et al, Helvetica Acta, 58/1, 278–83(1975).*
Chemical Abstract DN 131:243262, also cited as Tajima et al WO 9946232.*

(Continued)

*Primary Examiner*—Richard L. Raymond
*Assistant Examiner*—Sudhaker B. Patel
(74) *Attorney, Agent, or Firm*—Lewis J. Kreisler

(57) ABSTRACT

Compounds useful for the treatment of various metabolic disorders, such as insulin resistance syndrome, diabetes, hyperlipidemia, fatty liver disease, cachexia, obesity, atherosclerosis and arteriosclerosis, are disclosed.

19 Claims, 2 Drawing Sheets

FOREIGN PATENT DOCUMENTS

| | | |
|---|---|---|
| DE | 3012012 | 10/1981 |
| EP | 71399 | 2/1983 |
| EP | 288190 | 10/1988 |
| EP | 393400 | 10/1990 |
| EP | 407891 | 1/1991 |
| EP | 470832 * | 2/1992 |
| FR | 2191887 | 2/1974 |
| GB | 1488330 | 10/1977 |
| JP | 47025149 | 10/1972 |
| JP | 50014653 | 2/1975 |
| JP | 52025734 | 2/1977 |
| JP | 55015460 | 2/1980 |
| JP | 56115747 | 9/1981 |
| JP | 61040270 | 2/1986 |
| JP | 01063570 | 3/1989 |
| JP | 04159266 | 6/1992 |
| JP | 05230009 * | 9/1993 |
| JP | 10130241 | 5/1998 |
| JP | 01/181281 | 12/2002 |
| WO | WO 88/08418 | 11/1988 |
| WO | WO 92/12123 | 7/1992 |
| WO | WO 93/08799 | 5/1993 |
| WO | 9412181 * | 6/1994 |
| WO | WO 94/27993 | 12/1994 |
| WO | WO 95/13262 | 5/1995 |
| WO | WO 97/30017 | 8/1997 |
| WO | WO 98/07681 | 2/1998 |
| WO | WO 98/08836 | 3/1998 |
| WO | WO 98/25608 | 6/1998 |
| WO | 9803505 * | 10/1998 |
| WO | WO 99/11255 | 3/1999 |
| WO | 9919291 * | 4/1999 |
| WO | WO 99/20275 | 4/1999 |
| WO | 9946232 * | 9/1999 |
| WO | WO 99/62520 | 12/1999 |
| WO | 9962520 * | 12/1999 |
| WO | WO 00/23409 | 4/2000 |
| WO | WO 00/63161 | 10/2000 |
| WO | WO 01/40170 | 6/2001 |
| WO | WO 01/81340 | 11/2001 |
| WO | WO 02/02119 | 1/2002 |
| WO | WO 02/14291 | 2/2002 |
| WO | WO 02/59077 | 8/2002 |
| ZA | 6705655 | 10/1967 |

OTHER PUBLICATIONS

Chemical Abstract DN 116:214149, also cited as Suzuki et al EP 470832.*

Chemical Abstract DN 130:281874, also cited as Shoda et al WO 9919291.*

Chemical Abstract DN 122:315098, also cited as Egbertson et al WO 9412181.*

Witiak, et al., "Synthesis of Ethyl 6–Substituted–Chroman–and–Chromone–2–carboxylates. A Comparative Structure–Activity Study Employing the 6–Phenyl and Phenoxy Analogs in the Triton Hyperipidemic Rat Model", Journal Medical Chemistry, vol. 18, No. 9, pp. 934–942, 1975.

Karche, et al., "Electronic Effects in Migratory Groups . . . ", Journal of Organic Chemistry, vol. 66, No. 19, pp. 6323–6332, 2001. (Abstract).

Poupardin, et al., "First approach to the cycloisodityrosine unit of RA–IV", Tetrahedron Letters, vol. 42, No. 8, pp. 1523–1526, 2001. (Abstract).

Manthey, et al., "Synthesis of Human Ultraviolet Filter Compounds . . . ", Journal of Organic Chemistry, vol. 64, No. 11, pp. 3930–3933, 1999. (Abstract).

Wu, et al., "Improvement on the preparation of .beta.–keto esters", Huaxue Shiji, vol. 20, No. 6, pp. 376–377, 1998. (Abstract).

Wu, et al., "Total syntheses of furoguaiacin and related analogs", Huaxue Yanjiu Yu Yingyoung, vol. 9, No. 6, pp. 595–599, 1997. (Abstract).

Fadnavis, et al., "Baker's yeast mediated enantiospecific synthesis of anti–(2R,3R) . . . ", Tetrahedron Asymmetry, vol. 8, No. 24, pp. 4003–4006, 1997. (Abstract).

Wu, et al., "A modification of the Knorr oxidative coupling method for preparation of 1,4–diketones", Synthetic Communications, vol. 27, No. 2, pp. 331–336, 1997. (Abstract).

Girard, et al. "Syntheses of the syn and anti .alpha.–amino–.beta.–hydroxy acid of vancomycin . . . ", Tetrahedron Letters, vol. 37, No. 44, pp. 7967–7970, 1996. (Abstract).

Smith, et al., "Synthesis and PAF antagonist activity of some 2,5–diaryltetrahydrofurans incorporating PAF–like functional groups", European Journal of Medicinal Chemistry, vol. 31, No. 5, pp. 347–358, 1996. (Abstract).

Maruyama, et al., "A synthesis of (.+–.)–pinoresinol and its related compound using potassium persulfate (K2S208) oxidation of benzoylacetates", Heterocycles, vol. 37, No. 2, pp. 839–845, 1994. (Abstract).

Rao, et al., "Studies on cyclodepsipeptides. Part II. The total synthesis of jaspamide and geodiamolide–D", Tetrahedron Letters, vol. 34, No. 44, pp. 7085–7088, 1993. (Abstract).

Colotta, et al., "Tricyclic heteroaromatic systems . . . ", Farmaco, vol. 46, No. 10, pp. 1139–1154, 1991. (Abstract).

Dillard, et al., "(Phenylmethoxy) phenyl derivatives of w–oxo– and w–tetrazolylalkanoic acids . . . ", J. Med. Chem., vol. 34, No. 9, pp. 2768–2778, 1991. (Abstract).

Bose, et al., "Synthesis of 4–phenylcoumarins from *Dalbergia volubilis* and *Exostema caribaeum*", Phytochemistry, vol. 30, No. 7, pp. 2438–2439, 1991. (Abstract).

Bose, et al., "Synthesis of 4–phenylcoumarins", Indian J. Chem., Sect. B, vol. 29B, No. 5. pp. 422–444, 1990. (Abstract).

Colotta, et al., "Tricyclic heteroaromatic systems . . . ", J. Med. Chem., vol. 33, No. 9, pp. 2646–2651, 1990. (Abstract).

Kameo, et al., "Studies on hypolipidemic agents, IV. 3–[4–(Phenylthio) benzoyl] propionic acid derivatives", Chem. Pharm. Bull., vol. 37, No. 5, pp. 1260–1267, 1989. (Abstract).

Colotta, et al., "Tricyclic heteroaromatic systems: synthesis . . . " J. Pharm. Sci., vol. 78, No. 3, pp. 239–242, 1989. (Abstract).

Tanaka, et al., "Total synthesis of coumarinolignans, aquillochin (cleomiscosin C) and cleomiscosin D", Chem. Pharm. Bull., vol. 36, No. 10, pp. 3833–3837, 1988. (Abstract).

Parmar, et al., "Synthesis of new naturally occurring 4–phenyl–2H–1–benzopyran–2–ones", Bull. Chem. Soc. Jpn., vol. 61, No. 6, pp. 2277–2279, 1988. (Abstract).

Colotta, et al., "The correct synthesis of 2,3–dihydro–2–aryl–4–R–[1] benzopyrano [4,3–c] pyrazole–3–ones", Tetrahedron Letters, vol. 28, No. 43, pp. 5165–5168, 1987. (Abstract).

Tanaka, et al., "Total synthesis of daphneticin, a coumarinolignoid", Chem. Pharm. Bull., vol. 34, No. 2 pp. 628–632, 1986. (Abstract).

Ahluwalia, et al., "Synthesis of stevenin and melanettin", Symp. Pap.–IUPAC Int. Symp. Chem. Nat. Prod., 11th, vol. 3, pp. 11–13, 1978. (Abstract).

Yamaguchi, "Degradation of protolignin with metallic sodium in liquid ammonia", Ringyo Shikenjo Kenkyu Hokoku, vol. 281, pp. 1–78, 1976. (Abstract).

Okumura, et al., "Synthesis of chromone–3–carboxanilides", Chem. Pharm. Bull., vol. 22, No. 2, pp. 331–336, 1974. (Abstract).

Von Wacek, et al., "Synthesis of methoxylated compounds for a comparative investigation of the stability of methyl ether groups", Monatsh. Chem, vol. 97, No. 3, pp. 744–753, 1966. (Abstract).

Iwasa, et al., "The preparation of the biosynthetic precursor 3,7–dihydroxy–2, 6–dimethoxyphenthroindolizidine", J. Nat. Prod., vol. 51, No. 1, pp. 172–175, 1998. (Abstract).

Wong, et al., "Wedelolactone and coumestan derivatives as new antihepatotoxic and antiphlogistic principles", Arzneim.–Forsch., vol. 38, No. 5, pp. 661–665. 1988. (Abstract).

Witiak, et al., "Synthetic aci–reductiones. 3,4–Dihydroxy–2H–1–benzopyran–2–ones and their cis– and trans–4a, 5,6,7,8,8a–hexahydro diastereomers", J. Med. Chem., vol. 31, No. 7, pp. 1437–1445, 1988. (Abstract).

Entzeroth, et al., "Preparation of 3– (3–indolyl) Lactic acids . . . ", Liebigs Ann. Chem., No. 2, pp. 226–230, 1983. (Abstract).

Bhakuni, et al., Biosynthesis of tylophorine and tylophorinine, Tetrahedron, vol. 37, No. 2, pp. 401–407, 1981. (Abstract).

Naidu, et al., "Debenzylation by nickel–aluminum alloy", J. Indian Inst. Sci., vol. 62, No. 10, pp. 177–180, 1980. (Abstract).

Oka, et al., "Syntheses of N–heterocyclic compounds. XXVI. Syntheses of pyrido [3,4–d] pyridazine derivatives", Chem. Pharm. Bull., vol. 23, No. 10, pp. 2306–2317, 1975. (Abstract).

Saunders, et al., "Syntheses of carbon–14–labeled prizidilol dihydrochloride", J. Labelled Compd. Radiopharm., vol. 22, No. 9, pp. 869–881, 1985. (Abstract).

Arnoldi, et al., "Synthesis and sweet taste of some 2–phenylbenzodioxanes", J. Agric. Food Chem., vol. 34, No. 2, pp. 339–344, 1986. (Abstract).

Winters, et al., "Synthesis and pregnancy terminating activity of pyrazolo [1,5–a] indoles and quinolines", Eur. J. Med. Chem.—Chim. Ther., vol. 19, No. 3, pp. 215–218, 1984. (Abstract).

Herbert, et al., "Biosynthesis of phenanthroindolizidine alkaloids: incorporation of 2–pyrrolidin–2–ylacetophenone and benzoylacetic acid and derivatives", J. Chem. Soc., Perkin Trans. 1, No. 4., pp. 825–831, 1984. (Abstract).

Toja, et al., "Synthesis and pregnancy terminating activity of 2–arylpyrazolo [5,1–a] isoindoles and –isoquinolines", Eur. J. Med. Chem. –Chim. Ther., vol. 17, No. 3, pp. 223–227, 1982. (Abstract).

Ahluwalia, et al., "An unambiguous synthesis of melannein", Indian J. Chem., Sect. B, vol. 21B, No. 3, pp. 186–188, 1982. (Abstract).

Peleter, et al., "Synthesis and NMR spectra of 2,6– and 2,4–diaryl–3,7–dioxabicyclo [3.3.0] octanes", J. Chem. Soc., Perkin Trans. 1, No. 1, pp. 183–190, 1982. (Abstract).

Mangla, et al., "Synthesis of substituted 6,7–diphenyl–1,2, 3,5,8,8a–hexahydroindolizines", Indian J. Chem., Sect. B, vol. 19B, No. 11, pp. 931–937, 1980. (Abstract).

Mangla, et al. "Synthesis of tylophorine", Tetrahedron, vol. 36, No. 17, pp. 2489–2490, 1980. (Abstract).

Ahluwalia, et al., "A novel synthesis of 4–phenylcoumarins having a free hydroxyl group in the phenyl ring: synthesis of melanettin and stevenin", Heterocycles, vol. 14, No. 9, pp. 1329–1330, 1980. (Abstract).

Charlton, et al., "The synthesis of 2–methylchromone–3–carboxylic acid", J. Heterocycl. Chem., vol. 17, No. 3, pp. 593–594, 1980. (Abstract).

Liu, et al., "The New Antidiabetic Drug MCC–555 Acutely Sensitizes Insulin Signaling in Isolated Cardiomyocytes", Endocrinology, vol. 139, No. 11, pp. 4531–4539, (1998).

Kees, et al., "Perfluoro–N–[4–(1 H–tetrazol–5–ylmethyl) Phenyl)]–alkanamides. A New Class of Oral Antidiabetic Agents", Journal of Medicinal Chemistry, vol. 32, pp. 11–13, (1989).

Shinkai, et al. "4–(trans–4–Methylcyclohexyl)–4 Oxobutyric Acid (JTT–608). A New Class of Antidiabetic Agent", Journal of Medicinal Chemistry, vol. 41, No. 27, pp. 5420–5428, (1998).

Abstract 560–P, Hodge et al. "PN2022: Antidiabetic Efficacy and Reversal of Steatohepatitis in ob/ob Mice", Diabetes, Abstract Book 62nd Scientific Sessions, vol. 51 Suppl. 2, p. A139, Jun. 2002.

Abstract 561–P, Hodge, et al., "PN2034: Orally Active Antidiabetic Agent with a Unique Spectrum of of Activity and Enhanced Safety Profile", Diabetes, Abstract Book 62nd Scientific Sessions, vol. 51 Suppl. 2, p. A139, Jun. 2002.

Abstract 568–P, Lu, et al., "A Novel Antidiabetic Agent That is a Selective PPAR Modulator", Diabetes, Abstract Book 62nd Scientific Sessions, vol. 51, Suppl. 2., p. A141, Jun. 2002.

Abstract 586–P, von Borstel, et al. "PN2034: Reversal of Insulin Resistance and Attenuation of Weight Gain in Mice on a High–Fat Diet", Diabetes, Abstract Book 62nd Scientific Sessions, vol. 51, Suppl. 2, p. A145, Jun. 2002.

Poster #560, Hodge, et al., "PN2022: Antidiabetic Efficacy and Reversal of Steatohepatitis in ob/ob Mice." Presentation at the 62nd Scientific Sessions, Meeting of the American Diabetes Association on Jun. 14 18, 2002 and corresponding to Abstract 560–P.

Poster #561, Hodge, et al., "PN2034: Orally Active Antidiabetic Agent with a Unique Spectrum of Activity and Enhanced Safety Profile", Presentation given at the 62nd Scientific Sessions, Meeting of the American Diabetes Association on Jun. 14–18, 2002 and corresponding to Abstract 560–P.

Poster #568, Lu, et al., "PN2034–A Novel Antidiabetic Agent That Is a Selective PPAR Modulator", Presentation given at the 62nd Scientific Sessions, Meeting of the American Diabetes Association on Jun. 14–18, 2002 and corresponding to Abstract 568–P.

Poster #586, von Borstel, et al., "PN2034: Reversal of Insulin Resistance and Attenuation of Weight Gain in Mice on a High–Fat Diet", Presentation given at the 62nd Scientific Sessions, Meeting of the American Diabetes Association on Jun. 14–18, 2002 and corresponding to Abstract 586–P.

Owada, et al., "Improved synthesis of tricin", Nippon Kagaku Zasshi, vol. 91, No. 10, pp. 1002–1003, 1970. (Abstract).

Veronese, et al., "Ozonolysis of derivatices of 7–hydroxytryptophan", Gazz. Chim. Ital., vol. 97, No. 1, pp. 18–24, 1967. (Abstract).

Kawamatsu, et al., Studies on antihyperlipidemic agents. Part 1. Synthesis and hypolipidemic activities of phenoxyphenylalkanoic acid derivatives, Arzneim. Forsch, vol. 30, Issue 3, pp. 445–459, 1980. (Abstract).

Chemical Abstract DN 132:22755, also cited as WO99/62520.

Chemical Abstract DN 126:74645, also cited as J. Chem. Soc., Parkins Transactions 1, Org & Bio–Org. Chem., 21, 2603–2613, 1996.

Chemical Abstract DN 117:251790, also cited as Wo 92/12123.

Chemical Abstract DN 113: 115839, also cited as Synthetic communications, 20/5,773–81, 1990.

Chemical Abstract DN 99: 122287, also cited as EP 71399.

Kawamatsu et al., Arzneim. Forsh., vol. 30 ISS3, 454–459, 1980.

* cited by examiner

COMPOUNDS FOR THE TREATMENT OF METABOLIC DISORDERS

CROSS-REFERENCE TO PRIOR APPLICATIONS

This is a divisional of U.S. patent application Ser. No. 10/167,839, filed Jun. 12, 2002, the content of which is incorporated herein by reference. This application claims the benefit of U.S. Provisional Patent Application No. 60/297,282, filed Jun. 12, 2001, the content of which is incorporated herein by reference.

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions. Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary-defects of insulin resistance and islet failure with fewer or milder side effects than existing drugs.

Currently there are no safe and effective treatments for fatty liver disease. Therefore such a treatment would be of value in treating this condition.

SUMMARY OF THE INVENTION

This invention provides a biologically active agent, wherein the agent is a compound of the formula:

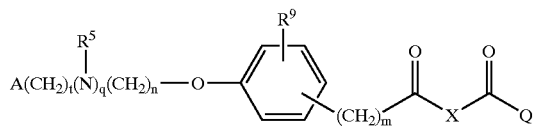

wherein n is 1 or 2; m is 0 or 1; q is 0 or 1; t is 0 or 1; $R^5$ is alkyl having from 1 to 3 carbon atoms; $R^9$ is hydrogen, halo, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and X is —$CH_2$—, Q is —$OR^1$ and $R^1$ is ethyl; or X is —$CH_2CR^{12}R^{13}$— or —$CH_2CH$ (NHAc)— wherein each of $R^{12}$ and $R^{13}$ is independently hydrogen or methyl, Q is $OR^1$ and $R^1$ is hydrogen or alkyl having from 1 to 7 carbon atoms; or X is —$CH_2CH_2$— and Q is $NR^{10}R^{11}$ wherein one of $R^{10}$ and $R^{11}$ is hydrogen, alkyl having from 1 to 3 carbon atoms or hydroxy, and the other is hydrogen or alkyl having from 1 to 3 carbon atoms; or when $R^1$ is hydrogen, a pharmaceutically acceptable salt of the compound.

This invention provides a biologically active agent, wherein the agent is a compound of the formula:

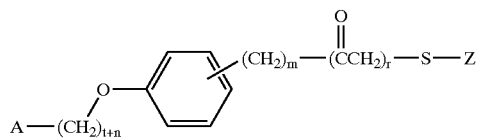

wherein n is 1 or 2; t is 0 or 1; m is 0 and r is 1, or m is 1 and r is 0; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are mono-substituted by methyl or ethyl; or a 5 or 6 membered heteroaromatic ring having 1 or 2 ring heteroatoms selected from N, S and O and the heteroaro matic ring is covalently bound to the remainder of the compound of formula II by a ring carbon; Z is

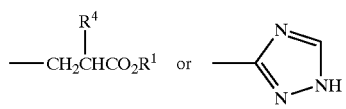

$R^1$ is hydrogen or alkyl having from 1 to 7 carbon atoms; $R^4$ is hydrogen; —NHCOOC(CH$_3$)$_3$; —NHCH$_3$; or —NHCH$_2$CH$_3$; or when $R^1$ is hydrogen, a pharmaceutically acceptable salt of the compound.

This invention provides a biologically active agent, wherein the agent is a compound of the formula:

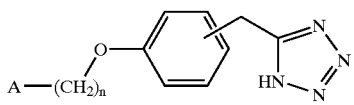

III wherein
n is 1 or 2; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein one or both ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula III by a ring carbon.

This invention provides a biologically active agent, wherein the agent is a compound of the formula:

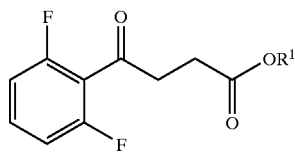

IV wherein $R^1$ is hydrogen or alkyl having from 1 to 7 carbon atoms; or when $R^1$ is hydrogen, a pharmaceutically acceptable salt of the compound.

This invention provides a biologically active agent, wherein the agent is a compound of the formula:

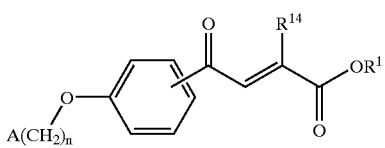

V' wherein n is 1 or 2; $R^1$ is hydrogen or alkyl having from 1 to 7 carbon atoms; $R^{14}$ is hydroxy or hydrogen; and A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

This invention provides a biologically active agent, wherein the agent is a compound of the formula:

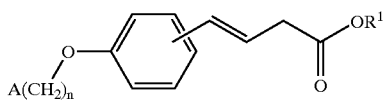

XCI wherein n is 1 or 2; $R^1$ is hydrogen or alkyl having from 1 to 3 carbon atoms; and A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

This invention provides a biologically active agent, wherein the agent is a compound of the formula:

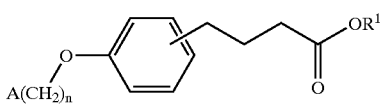

CXVI wherein n is 1 or 2; $R^1$ is hydrogen or alkyl having from 1 to 3 carbon atoms; and A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

This invention provides a biologically active agent, wherein the agent is a compound of the formula:

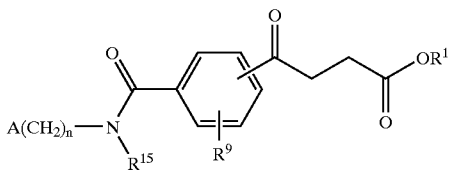

CXVII wherein n is 0, 1 or 2; $R^1$ is hydrogen or alkyl having from 1 to 3 carbon atoms; $R^{15}$ is hydrogen or alkyl having from 1 to 3 carbon atoms; $R^9$ is hydrogen, halo, hydroxy, or alkoxy having from 1 to 3 carbon atoms; A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

The biologically active agents described above have activity in one or more of the biological activity assays described below, which are established animal models of human diabetes and insulin resistance syndrome. Therefore such agents would be useful in the treatment of diabetes and insulin resistance syndrome. All of the exemplified compounds that were tested demonstrated activity in the biological activity assay or assays in which they were tested.

This invention provides the use of the biologically active agents described above in the manufacture of a medicament for the treatment of insulin resistance syndrome, diabetes, cachexia, hyperlipidemia, fatty liver disease, obesity, atherosclerosis or arteriosclerosis. This invention also provides methods of treating a mammalian subject with insulin resistance syndrome, diabetes, cachexia, hyperlipidemia, fatty liver disease, obesity, atherosclerosis or arteriosclerosis comprising administering to the subject an effective amount of a biologically active agent in accordance with this invention. This invention also provides a pharmaceutical composition comprising a biologically active agent of this invention and a pharmaceutically acceptable carrier.

This invention provides certain novel intermediates, which are useful in producing the biologically active agents of this invention. The invention also provides processes of producing the biologically active agents and intermediates.

DETAILED DESCRIPTION OF THE INVENTION

Definitions

Figure 1:
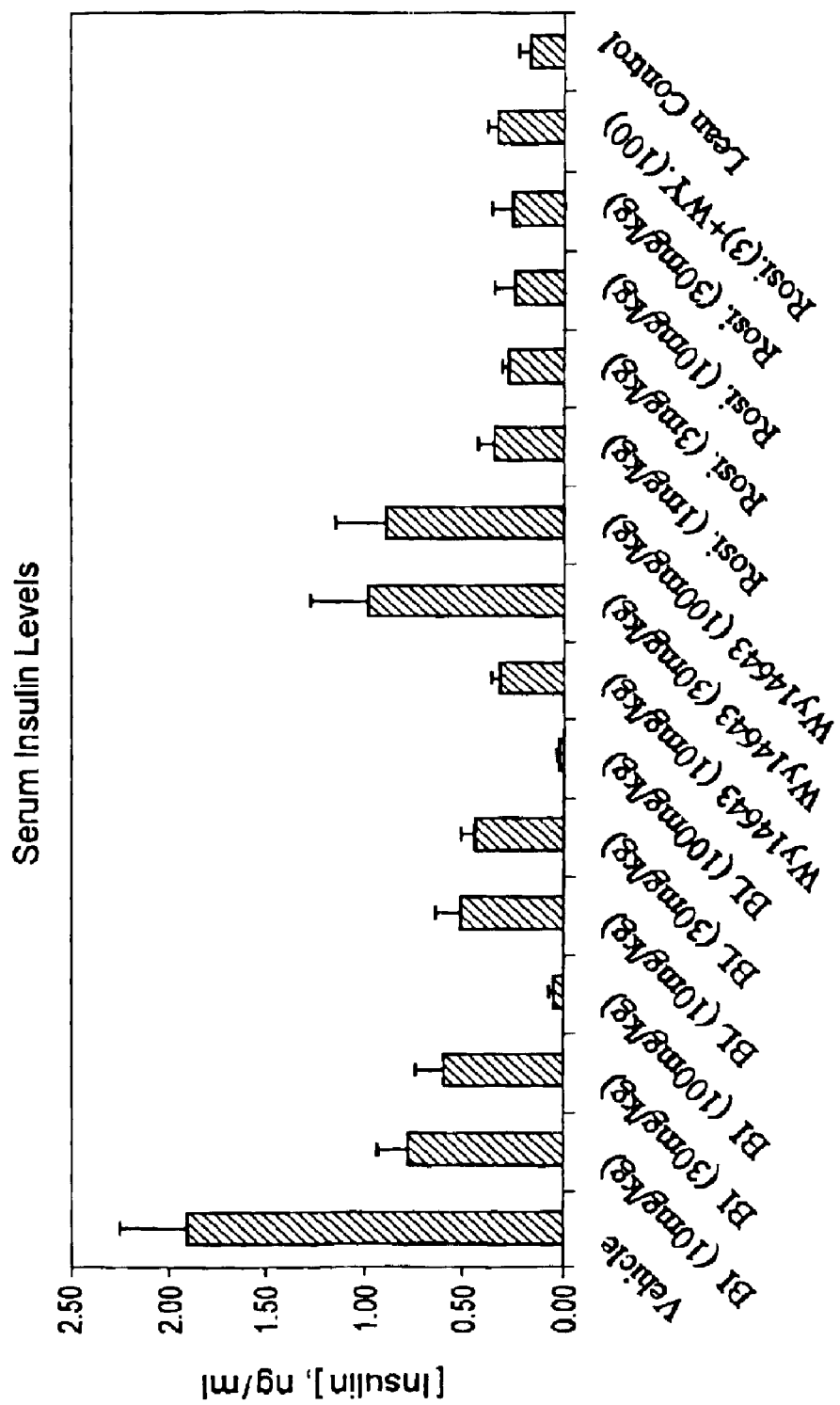
FIG. 1: Serum insulin levels in high fat-fed C57B1/6J mice receiving vehicle (negative control), Compound BI, Compound BL, Wy14643 or rosiglitazone.

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Examples of the biologically active compounds of the instant invention are listed below. These compounds are referred to herein by their chemical name or by the two-letter code shown below.

AA 4-(4-(2-Fluorobenzyloxy)phenyl)-4-oxobutyric acid;
AB 4-(4-(2-Methoxybenzyloxy)phenyl)-4-oxobutyric acid;
AC 3-[(4-(2-Fluorobenzyloxy)phenyl)-methylthio] propionic acid;
AD 4-(4-(3-Fluorobenzyloxy)phenyl)-4-oxobutyric acid;
AE 4-(4-(4-Fluorobenzyloxy)phenyl)-4-oxobutyric acid;
AF 4-(4-((2-Pyridinyl)-methoxy)phenyl)-4-oxobutyric acid;
AG 4-(4-(Benzyloxy)phenyl)-4-oxobutyric acid;
AH 4-(4-(2,6-Difluorobenzyloxy)phenyl)-4-oxobutyric acid;
AI 4-(4-(2-Chlorobenzyloxy)phenyl)-4-oxobutyric acid;
AJ 4-(4-(2-(2-Fluorophenyl)ethoxy)phenyl)-4-oxobutyric acid;
AK Ethyl 4-(4-(2-fluorobenzyloxyl)phenyl)-4-oxobutyrate;
AL 4-(4-(2-Methylbenzyloxy)phenyl)-4-oxobutyric acid;
AM 4-[4-(2-(N-(2-fluorobenzyl)-N-methylamino)ethoxy) phenyl]-4-oxobutyric acid;
AN 4-(3-(2-Methylbenzyloxy)phenyl)-4-oxobutyric acid;
AO Ethyl 4-(3-(2-fluorobenzyloxyl)phenyl)-4-oxobutyrate;
AP Ethyl 4-(4-(2-methylbenzyloxyl)phenyl)-4-oxobutyrate;
AQ Ethyl 4-(4-(2,6-difluorobenzyloxyl)phenyl)-4-oxobutyrate;
AR 4-(4-(2-(2-Thienyl)ethoxy)phenyl)-4-oxobutyric acid;
AS 4-(2,6-Difluorophenyl)-4-oxobutyric acid;
AT 4-(4-(2,5-Dimethylbenzyloxy)phenyl)-4-oxobutyric acid;
AU 4-(4-(2,5-Difluorobenzyloxy)phenyl)-4-oxobutyric acid;
AV 4-(4-(2,4-Difluorobenzyloxy)phenyl)-4-oxobutyric acid;
AW 4-(3-(2,6-Difluorobenzyloxy)phenyl)-4-oxobutyric acid;
AX 4-(4-((Cyclopropyl)-methoxy)phenyl)-4-oxobutyric acid;
AY 4-(4-(2-Trifluoromethylbenzyloxy)phenyl)-4-oxobutyric acid;
AZ 3-[(4-(2,6-Difluorobenzyloxy)phenyl)-methylthio] propionic acid;
BA 4-(2-(2,6-Difluorobenzyloxy)phenyl)-4-oxobutyric acid;
BB Ethyl 4-(4-(2,6-difluorobenzyloxy)phenyl)-3-oxobutyrate;
BC 3-(2-(4-(2,6-Difluorobenzyloxy)phenyl)-2-oxoethyl) thio-1H-1,2,4-triazole;
BD 5-[(4-(2,6-Difluorobenzyloxy)phenyl)-methyl]-1H-tetrazole;
BE (2RS)2-(N-Boc)-3-[2-(4-(2,6-difluorobenzyloxy) phenyl)-2-oxoethyl]thiopropionic acid;
BF Ethyl 2-Hydroxy-4-oxo-4-(4-(2,6-difluorobenzyloxy) phenyl)but-2-enoate;
BG (2RS)2-(N-Acetyl)-4-(4-(2,6-difluorobenzyloxy) phenyl)-4-oxobutyric acid;
BH 4-(3-((Cyclopropyl)-methoxy)phenyl)-4-oxobutyric acid;
BI 4-(3-(2,6-Dimethylbenzyloxy)phenyl)-4-oxobutyric acid;
BJ 4-(3-(2-Fluoro-6-methylbenzyloxy)phenyl)-4-oxobutyric acid;
BK Ethyl 4-(3-(2,6-dimethylbenzyloxyl)phenyl)-4-oxobutyrate;
BL 4-(3-(2,6-Dimethylbenzyloxy)phenyl)-4-oxobutyric acid Sodium salt;
BM 4-(4-(2,6-Dimethylbenzyloxy)phenyl)-4-oxobutyric acid;
BN 4-(3-(2,6-Dimethylbenzyloxy)phenyl)-4-oxobutyric acid Potassium salt;
BO 4-(3-(2,6-Dimethoxybenzyloxy)phenyl)-4-oxobutyric acid;
BP 4-(3-(2,6-Dimethylbenzyloxy)phenyl)-4-oxo-2,2-dimethylbutyric acid;
BQ 4-(3-(4-Trifluoromethylbenzyloxy)phenyl)-4-oxobutyric acid;
BR 4-(3-((Cyclobutyl)-methoxy)phenyl)-4-oxobutyric acid;
BS 4-(3-(2,6-Dimethylbenzyloxy)phenyl)butyric acid;

BT 4-[[4-(2,6-Dimethylbenzyloxy)-3-methoxy]phenyl]-4-oxobutyric acid;
BU 4-{3-[((4-Trifluoromethylbenzylamino)-carbonyl)-4-methoxy]phenyl}-4-oxobutyric acid;
BV 4-{3-[((2,6-Dimethyllbenzylamino)-carbonyl)-4-methoxy]phenyl}-4-oxobutyric acid;
BW 4-(3-(2,6-Dimethylbenzyloxy)phenyl)-4-oxobutanecarbohydroxamic acid;
BX 4-(3-(2,6-Dimethylbenzyloxy)phenyl)-4-oxobutyramide;
BY 4-(3-(2,6-Dimethylbenzyloxy)phenyl)-4-oxo-2-butenoic acid; and
BZ 4-(3-(2,6-Dimethylbenzyloxy)phenyl)-3-butenoic acid.

As used herein the transitional term "comprising" is open-ended. A claim utilizing this term can contain elements in addition to those recited in such claim.

DETAILED DESCRIPTION OF ACTIVE COMPOUNDS

In an embodiment of the agent of Formula I', the agent is a compound of the formula:

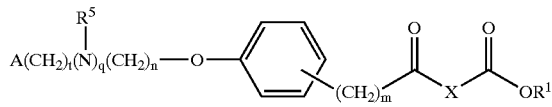

I wherein n is 1 or 2; m is 0 or 1; q is 0 or 1, t is 0 or 1; $R^5$ is alkyl having from 1 to 3 carbon atoms; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and X is —$CH_2$— and $R^1$ is ethyl; or X is —$CH_2CH_2$— or —$CH_2CH(NHAc)$— and $R^1$ is hydrogen or alkyl having from 1 to 7 carbon atoms; or when $R^1$ is hydrogen, a pharmaceutically acceptable salt of the compound.

In different embodiments of the agent of Formula I, $R^1$ is hydrogen or ethyl; q is 0; or X is —$CH_2CH_2$—.

In another embodiment of the agent of Formula I, A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy each halo is independently fluoro or chloro. In a specific embodiment each halo substituent on phenyl ring A is fluoro. In a more specific embodiment phenyl ring A is substituted by 2 fluoro groups. In a specific embodiment the alkyl, perluoroalkyl, alkoxy or perfluoroalkoxy has 1 carbon atom.

In another embodiment of the agent of Formula I, A is cycloalkyl having from 3 to 6 ring carbon atoms wherein the cycloalkyl is unsubstituted or one or two ring carbons are independently mono-substituted by methyl or ethyl. In a specific embodiment the cycloalkyl is unsubstituted or one or both ring carbons adjacent to the ring carbon covalently bound to the remainder of the compound of formula I are independently mono-substituted by methyl or ethyl. In a more specific embodiment A is unsubstituted cyclopropyl.

In another embodiment of the agent of Formula I, q is 1 and $R^5$ is methyl.

In another embodiment the agent is a compound of the formula:

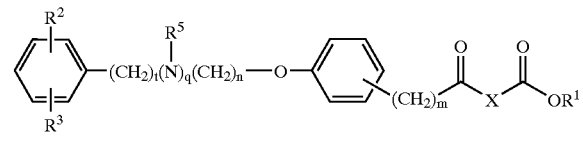

IA wherein n is 1 or 2; m is 0 or 1; q is 0 or 1; t is 0 or 1; $R^2$ and $R^3$ are each independently selected from hydrogen, halo, alkyl having 1 or 2 carbon atoms, perfluoromethyl, alkoxy having 1 or 2 carbon atoms, and perfluoromethoxy; $R^5$ is alkyl having from 1 to 3 carbon atoms; and X is —$CH_2$— and $R^1$ is ethyl; or X is —$CH_2CH_2$— or —$CH_2CH(NHAc)$— and $R^1$ is hydrogen or alkyl having from 1 to 7 carbon atoms; or when $R^1$ is hydrogen, a pharmaceutically acceptable salt of the compound. In a more specific embodiment $R^1$ is hydrogen or ethyl. Examples of compounds of Formula IA include Compound AM and Compound BG.

In a specific embodiment the agent is a compound of the formula:

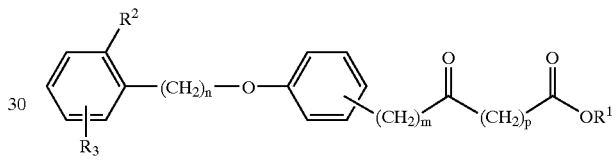

IA1 wherein n is 1 or 2; m is 0 or 1; p is 1 and $R^1$ is ethyl; or p is 2 and $R^1$ is hydrogen or alkyl having from 1 to 7 carbon atoms; $R^2$ and $R^3$ are each independently selected from hydrogen, halo, alkyl having 1 or 2 carbon atoms, perfluoromethyl, alkoxy having 1 or 2 carbon atoms, and perfluoromethoxy; or when $R^1$ is hydrogen, a pharmaceutically acceptable salt of the compound. In a more specific embodiment $R^1$ is hydrogen or ethyl. In a still more specific embodiment one of $R^2$ and $R^3$ is hydrogen or halo and the other is halo. Examples of such compounds include Compound AD, Compound AE and Compound AI. In another still more specific embodiment $R^2$ is fluoro and $R^3$ is hydrogen. Examples of such compounds include Compound AA, Compound AJ, Compound AK, and Compound AO. In another still more specific embodiment $R^2$ is fluoro and $R^3$ is fluoro. Examples of such compounds include Compound AU, Compound AV and Compound BB.

In a more specific embodiment the agent is a compound of the formula:

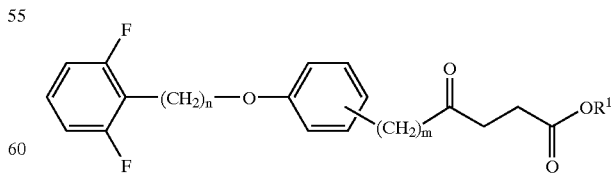

IA1a wherein n is 1 or 2; m is 0; $R^1$ is H or alkyl having from 1 to 7 carbon atoms; or when $R^1$ is hydrogen, a pharmaceutically acceptable salt of the compound. Examples of such compounds include Compound AH, Compound AQ, Compound AW and Compound BA. In a still more specific embodiment one of $R^2$ and $R^3$ is methyl, methoxy or perfluoromethyl and the other is hydrogen or methyl. In one embodiment $R^2$ is methyl, methoxy or perfluoromethyl and $R^3$ is hydrogen. Examples of such compounds include Compound AB, Compound AL, Compound AN, Compound AP and Compound AY. In another embodiment $R^2$ is methyl and $R^3$ is methyl. Examples of such compounds include Compound AT and Compound BI. In another embodiment $R^2$ is hydrogen and $R^3$ is hydrogen. Examples of such compounds include Compound AG.

In another embodiment the agent is a compound of the formula:

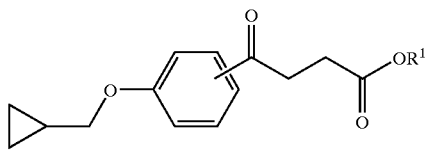

IB wherein $R^1$ is hydrogen or alkyl having from 1 to 7 carbon atoms, or when $R^1$ is hydrogen, a pharmaceutically acceptable salt of the compound. In a specific embodiment $R^1$ is hydrogen or ethyl. Examples of such compounds include Compound AX and Compound BH.

In another embodiment the agent is a compound of the formula:

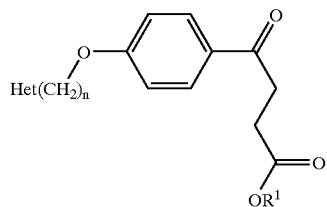

IC wherein n is 1 or 2; $R^1$ is hydrogen or alkyl having from 1 to 7 carbon atoms; and Het is a 5 or 6 membered heteroaromatic ring having 1 or 2 ring heteroatoms selected from N, S and O and the heteroaromatic ring is covalently bound to the remainder of the compound of formula IC by a ring carbon. In a specific embodiment $R^1$ is hydrogen or ethyl. Examples of such compounds include Compound AF and Compound AR.

In an embodiment of the agent of Formula II, A is cycloalkyl having from 3 to 6 ring carbon atoms wherein the cycloalkyl is unsubstituted or one or both of the ring carbons adjacent to the remainder of the compound of formula II are mono-substituted by methyl or ethyl. In another embodiment of the agent of Formula II, A is phenyl, unsubstituted or substituted by 1 or 2 groups selected from: fluoro, alkyl having 1 or 2 carbon atoms, perfluoromethyl, alkoxy having 1 or 2 carbon atoms, and perfluoromethoxy.

In another embodiment, the agent is a compound of the formula:

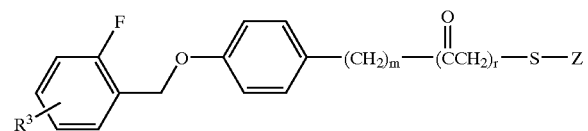

IIA wherein m is 0 or 1; r is 0 or 1; Z is

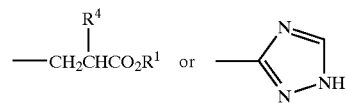

$R^1$ is hydrogen or alkyl having from 1 to 7 carbon atoms; $R^4$ is hydrogen; —NHCOOC(CH$_3$)$_3$; —NHCH$_3$; or —NHCH$_2$CH$_3$; $R^3$ is hydrogen or halo; or when $R^1$ is hydrogen, a pharmaceutically acceptable salt of the compound. In a specific embodiment $R^1$ is hydrogen or ethyl. Examples of such compounds include Compound AC, Compound AZ, Compound BC and Compound BE.

In an embodiment of the agent of Formula III, A is phenyl, unsubstituted or substituted by. 1 or 2 groups selected from: halo, alkyl having 1 or 2 carbon atoms, perfluoromethyl, alkoxy having 1 or 2 carbon atoms, and perfluoromethoxy. Examples of such compounds include Compound BD.

In an embodiment of the agent of Formula IV, $R^1$ is hydrogen or ethyl. Examples of such compounds include Compound AS.

In an embodiment of the agent of Formula V', the agent is a compound of the formula:

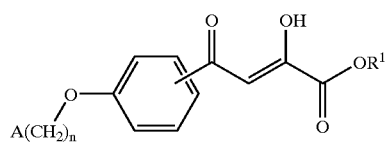

V wherein n is 1 or 2; $R^1$ is hydrogen or alkyl having from 1 to 7 carbon atoms; A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; or a pharmaceutically acceptable salt of the compound.

In an embodiment of the agent of Formula V, the agent is a compound of the formula:

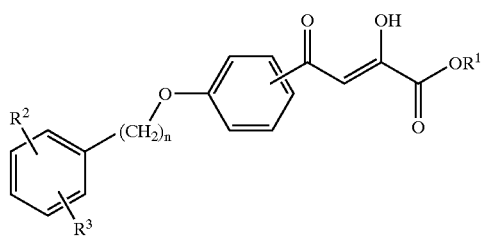

VA wherein n is 1 or 2; $R^1$ is hydrogen or alkyl having from 1 to 7 carbon atoms; $R^2$ and $R^3$ are each independently selected from hydrogen, halo, alkyl having 1 or 2 carbon atoms, perfluoromethyl, alkoxy having 1 or 2 carbon atoms, and perfluoromethoxy, or a pharmaceutically acceptable salt of the compound. In a specific embodiment $R^1$ is hydrogen or ethyl. Examples of such compounds include Compound BF.

Use in Methods of Treatment

This invention provides a method for treating a mammalian subject with a condition selected from the group consisting of insulin resistance syndrome and diabetes (both primary essential diabetes such as Type I Diabetes or Type II Diabetes and secondary nonessential diabetes), comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. As shown in the Examples, compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or amelioriating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. For oral administration to a human the anticipated preferred daily dose of Compound AH is from 100 mg to 400 mg; of Compound AW is from 30 to 300 mg; and of Compound BI is from 10 to 200 mg. In the case of oral administration to a mouse the agent is generally administered in a daily dose from 0.1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5–80 mg/day; clofibrate 2000 mg/day; gemfibrozil 1200 to 2400 mg/day, rosiglitazone 4 to 8 mg/day; pioglitazone 15 to 45 mg/day; acarbose 75–300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, e.g. 50 to 400 mg/day of Compound AH, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. Suitable daily dose ranges for selected compounds of the invention for treatment of NIDDM (either as monotherapy or in combination with other antidiabetic drugs) are from 50 mg to 400 mg of Compound AH, from 15 mg to 300 mg of Compound AW, or from 5 mg to 200 mg of Compound BI. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Suitable daily dose ranges for selected compounds of the invention for treatment of hypertriglyceridemia are from 50 mg to 400 mg of Compound AH, from 15 mg to 300 mg of Compound AW, or from 5 mg to 200 mg of Compound BI. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. As is shown in the Examples, compounds of the invention, e.g. Compound AW, reduce serum liver transaminases and liver fat content in an established animal model of NASH (ob/ob obese mice), and are therefore useful for treatment of fatty liver disease. An appropriate dose range of Compound AW for treatment of fatty liver disease is 15 to 300 mg/day. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. Accordingly, preferred oral compositions for treatment of humans comprise from 50 mg to 400 mg of Compound AH, from 15 mg to 300 mg of Compound AW, or from 5 mg to 200 mg of Compound BI. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semil-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

Reaction Schemes

The biologically active compounds of the present invention can be made in accordance with the following reaction schemes.

The compound of formula I' where X is —$CH_2CR^{12}R^{13}$—, q and m are 0, t is 0 or 1, and n is 1 or 2, $R^9$ is hydrogen, halo, or alkoxy having 1 to 3 carbon atoms, Q is $OR^1$ where $R^1$ is hydrogen or alkyl having from 1 to 7 carbons, i.e. compounds of formula:

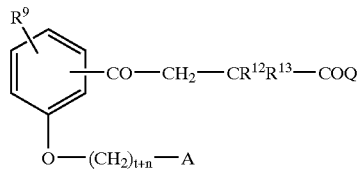

wherein A is as described above, and $R^1$ is hydrogen or alkyl having from 1 to 7 carbon atoms, $R^{12}$ and $R^{13}$ is independently hydrogen or methyl can be prepared from the compound of formula VI via the reaction scheme in Scheme 1.

In the reaction scheme of Scheme 1, A, t, n and $R^9$ are as above. $R^6$ is an alkyl group containing from 1 to 7 carbon atoms, $R^{12}$ and $R^{13}$ is independently hydrogen or methyl and Y is a leaving group.

The compound of formula VI is converted to the compound of formula VIII via reaction of step (a) using Mitsunobu condensation of VI with VII using triphenylphosphine and diethyl azodicarboxylate. Any of the conditions conventionally used in Mitsunobu reactions can be utilized to carry out the reaction of step (a).

The compound of formula VIII can also be prepared by etherifying or alkylating the compound of formula VI with a compound of formula IX as in reaction of step (b). In the compound of formula IX, Y can be any conventional leaving group such as mesyloxy, tosyloxy or a halide. Any conventional method of etherifying of a hydroxyl group through reaction with a halide or leaving group can be utilized to carry out the reaction of step (b). The reaction of step (b) is preferred over step (a) if compund of formula IX is readily available.

The compound of formula VIII is converted to the compound of formula XI via reaction of step (c) by alkylating the compound of formula VIII with the compound of formula X. This reaction is carried out utilizing a conventional base which converts acetophenone to 3-keto ester (i.e. gamma-keto ester). Any conventional base for this purpose can be utilized in the reaction of step (c). In carrying out this reaction it is generally preferred to utilize alkali metal salts of hexamethyldisilazane such as lithium bis(trimethylsilyl) amide as base. Generally this reaction is carried out in an inert solvent such as tetrahydrofuran: 1,3-Dimethyl-3,4,5,6-tetrahydro-2(1H)-pyrimidinone (5:1). Any of the conditions conventional in such alkylation reactions can be utilized to carry out the reaction of step (c).

The compound of formula XI is the compound of formula I' where $R^1$ is an alkyl group containing from 1 to 7 carbon atoms. The compound of formula XI can be converted to the free acid i.e. the compound of formula I' where $R^1$ is H by ester hydrolysis. Any conventional method of ester hydrolysis will produce the compound of formula I' where $R^1$ is H.

The compound of general formula VII can be prepared by reducing the corresponding acid of formula A-$(CH_2)_{t+n}$—$CO_2H$. The reaction is carried out first by esterification of compound of formula A-$(CH_2)_{t+n}CO_2H$ with methyl iodide, followed by reduction utilizing a conventional base for example, lithium aluminium hydride or the like in an inert organic solvent for example, tetrahydrofuran or the like. Any of the conditions conventional in such reduction reactions can be utilized to carry out this reaction.

Scheme 1

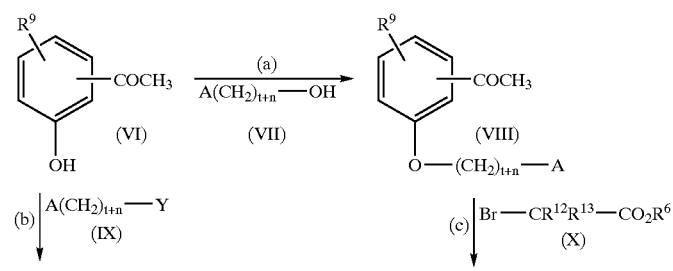

-continued

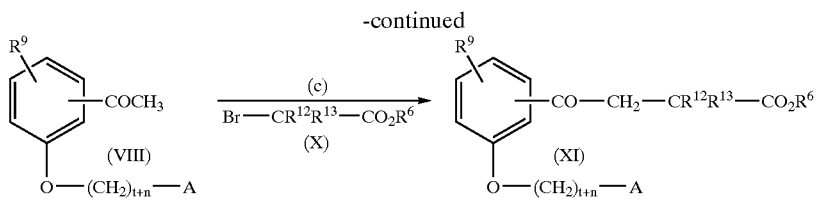

The compound of formula VII where A is 2,6 Dimethyl phenyl can be prepared from the compound of formula XCI, via the reaction scheme in Scheme 2.

In Scheme 2, the compound of formula XCI can be converted to compound of formula VII by esterification with methyl iodide, followed by reduction with lithium aluminum hydride via reaction of step (r''). The reaction of step (r'') can be carried out utilizing a conventional reducing agent. In carrying out this reaction it is generally preferred to utilize lithium aluminum hydride as the reducing agent. Any of the conditions conventional in reduction reactions can be utilized to carry out this reaction.

Scheme 2

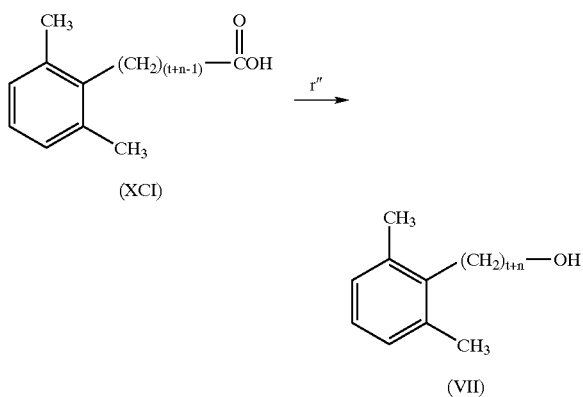

The compound of formula I where X is —$CH_2$—, q is 0, m is 1, t is 0 or 1 and n is 1 or 2, i.e. compounds of the formula:

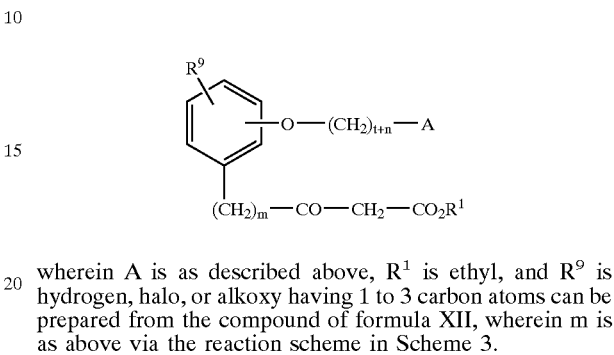

wherein A is as described above, $R^1$ is ethyl, and $R^9$ is hydrogen, halo, or alkoxy having 1 to 3 carbon atoms can be prepared from the compound of formula XII, wherein m is as above via the reaction scheme in Scheme 3.

In Scheme 3, A is as above, Y is a leaving group such as halide, mesyloxy or tosyloxy. $Y^1$ is chloro.

In Scheme 3, the compound of formula XII is converted into the ethyl ester of formula XIII using ethanol via reaction of step (d). Any conventional method of converting acid to ethyl ester can be utilized to carry out this reaction.

The compound of formula XIII can be converted to compound of formula XIV in the same manner as described in the connection with reaction of step (a) or (b) hereinbefore.

In the step of (f), the compound of formula XIV is hydrolyzed to produce the compound of formula XV. Any conventional method of basic hydrolysis to hydrolyze ester can be utilized to carry out this reaction.

The compound of formula XV is converted to the acid chloride of formula XVI via reaction of step (g) by reaction with thionyl chloride. Any of the conventional methods of converting acid to acid halide can be utilized to carry out this reaction of step (g).

The compound of formula XVII is reacted with acid chloride of formula XVI to produce the compound of formula XVIII via reaction of step (h). Any conventional base can be utilized to carry out this reaction with the preferred base being pyridine. The resulting acylated Meldrum acids were not isolated, and instead after workup they were refluxed in absolute ethanol to give the 2-ketoesters. Any conventional conditions to carry out the reaction of step (h) can be utilized.

The compound of formula XVIII is the compound of formula I where $R^1$ is ethyl.

Scheme 3

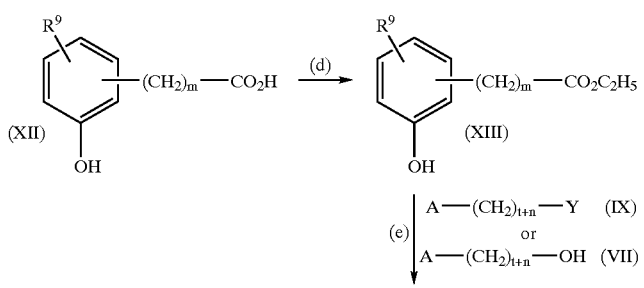

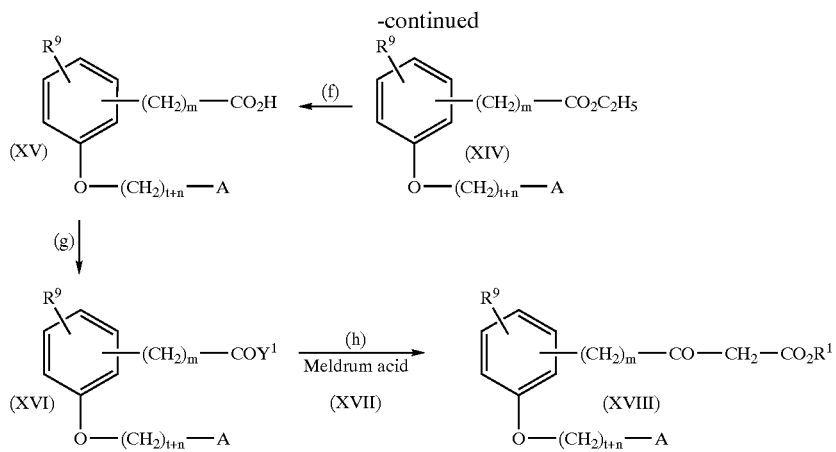

The compound of formula I' where q is 1, $R^5$ is an alkyl group having 1 to 3 carbon atoms where X is $-CH_2CR^{12}R^{13}-$, m is 0, t is 0 or 1 and n is 1 or 2, i.e. compounds of the formula:

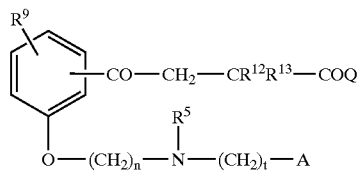

wherein A is as above, $R^1$ is hydrogen or alkyl having from 1 to 7 carbon atoms, and $R^{12}$ and $R^{13}$ is independently hydrogen or methyl, $R^9$ is hydrogen, halo, or alkoxy having 1 to 3 carbon atoms, Q is $OR^1$ where $R^1$ is hydrogen or alkyl having from 1 to 7 carbons, can be prepared from the compound of formula XIX, wherein t and A are as above via the reaction scheme in Scheme 4.

In Scheme 4, t, n, A, $R^1$, $R^9$, $R^{12}$, $R^{13}$ and $R^5$ are as above. $R^6$ is an alkyl group having 1 to 7 carbon atoms. $Y^1$ is chloro.

In Scheme 4, the compound of formula XIX is mesylated to furnish the compound of formula XX via reaction of step (i). Any conventional conditions to carry out mesylation can be utilized. The compound of formula XX is then heated with the compound of formula XXI to produce the compound of formula XXII. Any of the conditions conventional to produce amino alcohol can be utilized in reaction of step (j).

In the compound of formula XXII, alcohol is then displaced by chloro by treating the compound of formula XXII with thionyl chloride to produce compound of formula XXIII via reaction of step (k). Any conventional method to displace alcohol with halo can be utilized to carry out this reaction.

The compound of formula XXIII is reacted with a compound of formula VI in the presence of base using dimethylformamide as solvent via reaction of step (l) to produce the corresponding compound of formula XXIV. The position of the substituents in the compound of formula VI will determine the position of the substituents in the compound of formula XXIV. Any conventional method of etherification of a hydroxyl group in the presence of base (preferred base being potassium carbonate) with a halide can be utilized to carry out the reaction of step (l). The compound of formula XXIV is converted to the compound of formula XXV via reaction of step (m) by alkylating the compound of formula XXIV with the compound of formula X in the presence of alkali metal silyl amide as base (eg. lithium hexamethyldisilane or sodium hexamethyldisilane). This reaction is carried out in the same manner as described in connection with reaction of step (c) of Scheme 1.

The compound of formula XXV is the compound of formula I' where $R^1$ is an alkyl group having 1 to 7 carbon atoms. The compound of formula XXV can be converted to the free acid i.e. the compound of formula I' where $R^1$ is H by ester hydrolysis. Any conventional method of ester hydrolysis will produce the compound of formula I' where $R^1$ is H.

Scheme 4

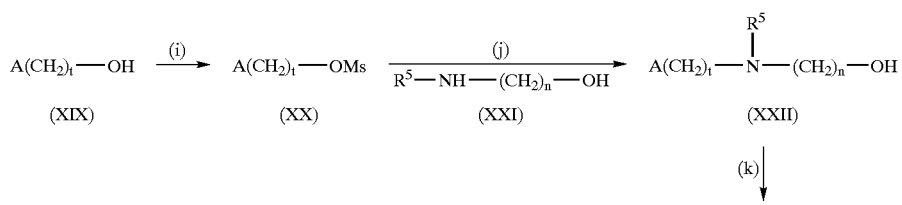

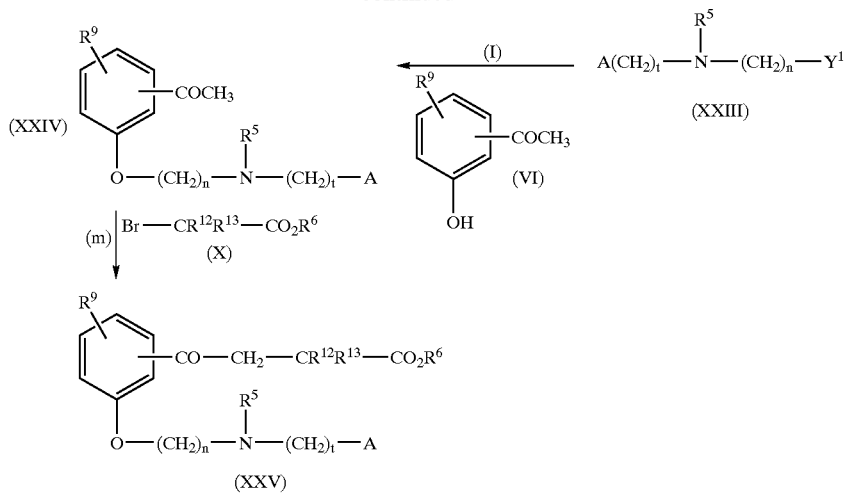

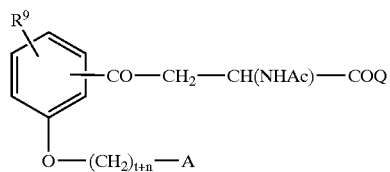

The compound of formula I' where X is —CH$_2$CH(NHAc),— m is 0, q is 0, t is 0 or 1 and n is 1 or 2, i.e. compounds of the formula:

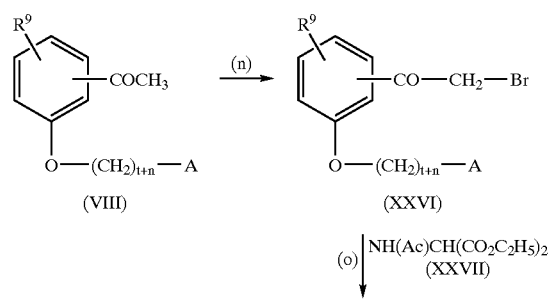

wherein A is as above, R$^1$ is hydrogen on alkyl having from 1 to 7 carbon atoms, and R$^9$ is hydrogen, halo, or alkoxy having 1 to 3 carbon atoms, Q is OR$^1$ where R$^1$ is hydrogen or alkyl having from 1 to 7 carbons can be prepared from the compound of formula VIII, via the reaction scheme in Scheme 5.

In Scheme 5, t, n, A, R$^9$ and R$^1$ are as above. R$^7$ is an alkyl group having 1 to 7 carbon atoms.

The compound of formula VIII is prepared in the same manner as described hereinbefore in connection with reaction of step (a) or (b) in Scheme 1.

The compound of formula VIII is converted to compound of formula XXVI by selective bromination of the methyl ketone moiety via reaction of step (n) by treating the compound of formula VIII with CuBr$_2$. Any selective bromination conditions to convert methyl ketone to 1-bromoketone can be utilized to carry out the reaction of step (n).

The compound of formula XXVI can be converted to compound of formula XXVIII via reaction of step (o) by treating the compound of formula XXVI with the sodium salt of compound of formula XXVII in ethanol. Any conventional conditions for this alkylation reaction can be utilized to carry out this reaction.

The compound of formula XXVIII is converted to compound of formula XXIX via reaction of step (p) by de-esterification employing 4 equivalents of sodium hydroxide.

Initial mono de-esterification followed by slow hydrolysis of the remaining ethyl ester was observed. Removal of solvent and incubation of the residue in acetic acid produced the compound of formula XXIX.

The compound of formula XXIX is the compound of formula I' where R$^1$ is H.

The compound of formula XXIX can be converted to compound of formula XXXI where R$^7$ is an alkyl chain having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (q).

The compound of formula XXXI is the compound of formula I' where R$^1$ is an alkyl chain having 1 to 7 carbon atoms.

Scheme 5

-continued

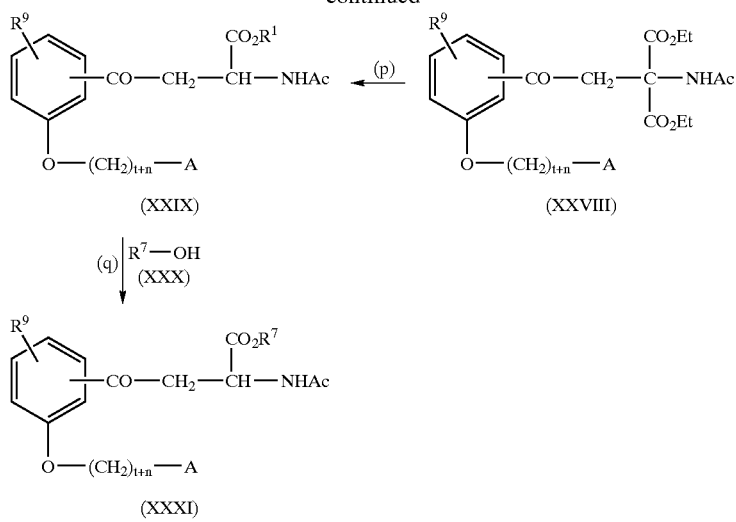

The compound of formula I where X is —$CH_2$—, q and m are 0, t is 0 or 1 and n is 1 or 2, i.e. compounds of formula:

[Structure with $R^9$, COCH$_2$CO$_2$R$^1$, O—(CH$_2$)$_{t+n}$—A]

wherein t, n, and A are as described above, $R^9$ is hydrogen, halo, or alkoxy having 1 to 3 carbon atoms and $R^1$ is ethyl can be prepared from the compound of formula LX, via the reaction scheme in Scheme 6.

In the reaction scheme of Scheme 6, A, t, $R^9$ and n are as above, Y is a leaving group and $Y^1$ is chloro.

In Scheme 6, the compound of formula LX is converted to compound of formula LXI in the same manner as described hereinbefore in connection with the reaction of steps (a) or (b) in Scheme 1.

In the step of (q'), the compound of formula LXI is hydrolyzed to produce the compound of formula LXII in the same manner as described in connection with the reaction of step (f) in Scheme 3.

The compound of formula LXII is converted to compound of formula LXIII via reaction of step (r') in the same manner as described in connection with reaction of step (g) in Scheme 3.

The compound of formula LXIV is first treated with 2 equivalents of n-butyllithium at low temperature and then compound of formula LXIII is added to produce compound of formula LXV (Weirenga, W.; Skulnick, H. I. J.O.C. 1979, 44, 310–311).

The compound of formula LXV is the compound of formula 1 where $R^1$ is ethyl.

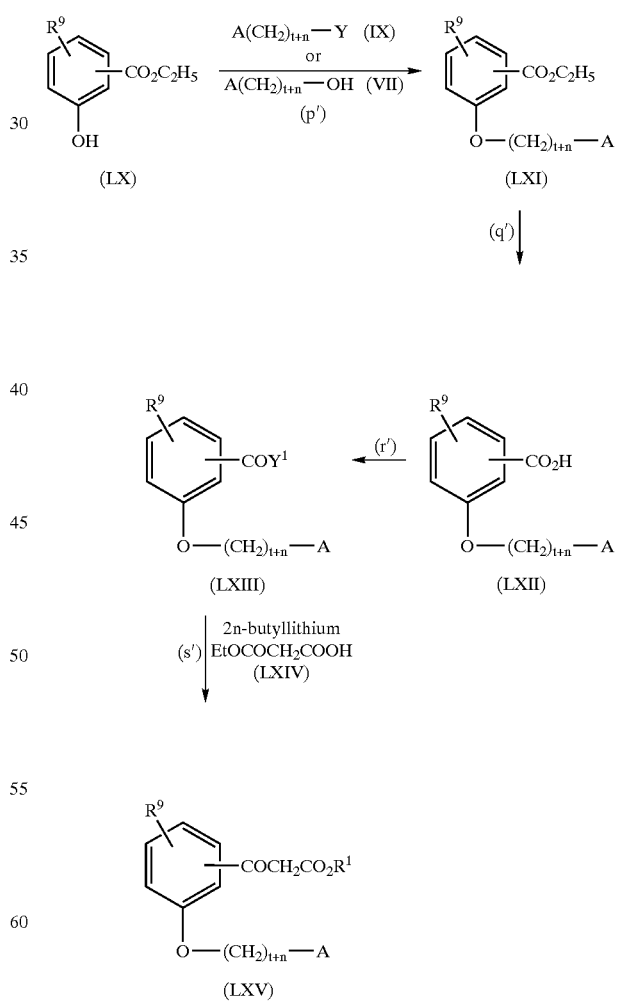

The compound of formula I where q is 1, $R^5$ is an alkyl group having 1 to 3 carbon atoms, where X is —$CH_2$—, m is 0, t is 0 or I and n is 1 or 2, i.e. compounds of formula:

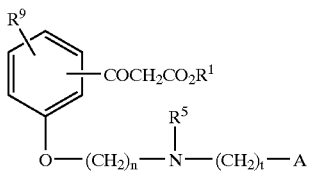

wherein A is as described above, $R^9$ is hydrogen, halo, or alkoxy having 1 to 3 carbon atoms and $R^1$ is ethyl can be prepared from the compound of formula LX via the reaction scheme in Scheme 7.

In the reaction scheme of Scheme 7, A, t, $R^9$ and n are as above, $Y^1$ is chloro. $R^5$ is an alkyl group having from 1 to 3 carbon atoms.

In Scheme 7, the compound of formula LX is reacted with compound of formula XXIII (prepared in the same manner as described in Scheme 4) to produce the compound of formula LXVI via reaction of step (t'). This rection is carried out in the same manner as described hereinbefore in the connection with reaction of step (l) in Scheme 4.

In the step of (u'), the compound of formula LXVI is hydrolyzed to produce the compound of formula LXVII in the same manner as described in the reaction of step (f) in Scheme 3.

The compound of formula LXVII is converted to compound of formula LXVIII via reaction of step (v') in the same manner as described in connection with the reaction of step (g) in Scheme 3.

The compound of formula LXIV is first treated with 2 equiv of n-butyllithium at low temperature and then compound of formula LXIII is added to produce compound of formula LXV (Weirenga, W.; Skulnick, H. I. J.O.C. 1979, 44, 310–311).

The compound of formula LXIX is the compound of formula 1 where $R^1$ is an alkyl group having 2 carbon atoms.

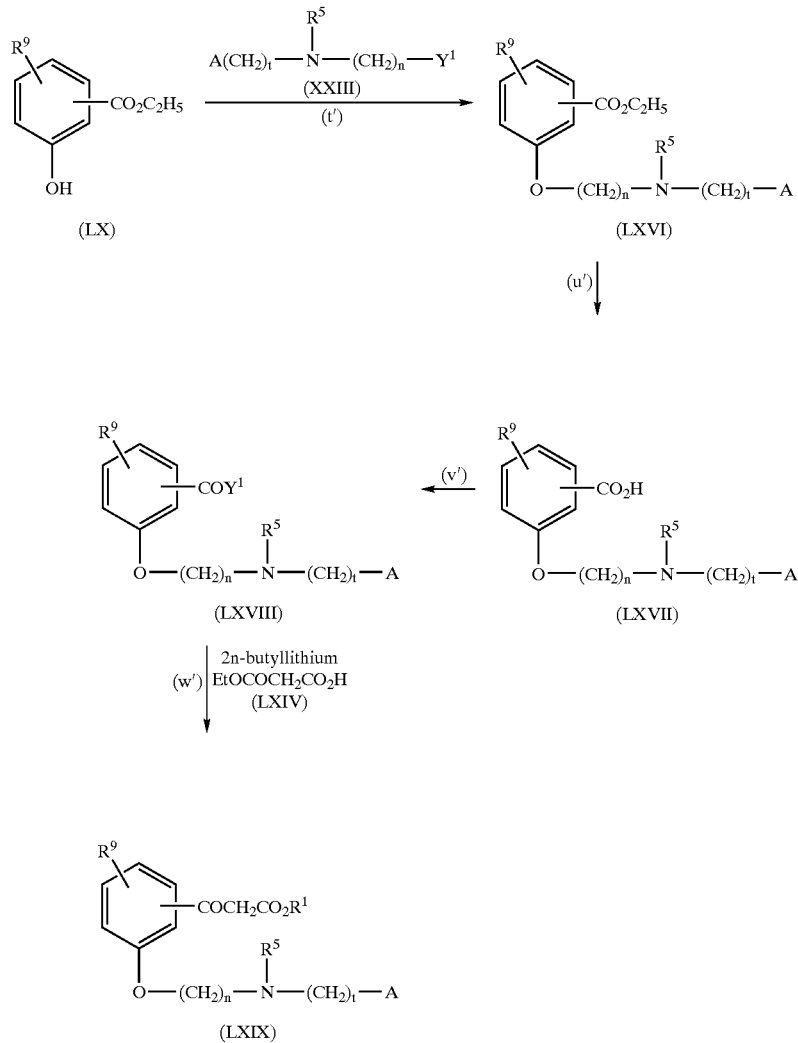

Scheme 7

The compound of formula I' where q is 1, $R^5$ is an alkyl group having 1 to 3 carbon atoms, $R^1$ is hydrogen or alkyl having from 1 to 7 carbons, $R^9$ is hydrogen, halo, or alkoxy having 1 to 3 carbon atoms, Q is $OR^1$ where $R^1$ is hydrogen or alkyl having from 1 to 7 carbons, X is —$CH_2CH$(NHAc)—, m is 0, t is 0 or 1 and n is 1 or 2, i.e. compounds of the formula:

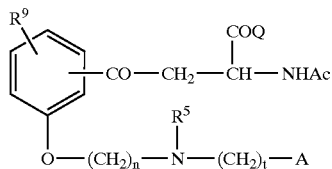

wherein t, n, A and $R^1$ are as above, can be prepared from the compound of formula VI, via the reaction scheme in Scheme 8.

In Scheme 8, t, n, A, $R^9$ and $R^1$ are as above. $R^7$ is an alkyl group having 1 to 7 carbon atoms. $R^5$ is an alkyl group having 1 to 3 carbon atoms. $Y^1$ is chloro.

The compound of formula XXIV is prepared in the same manner as described hereinbefore in connection with reaction of step (l) in Scheme 4.

The compound of formula XXIV is converted to compound of formula LXX by selective bromination of the methyl ketone moiety via reaction of step (x') by treating the compound of formula XXIV with $CuBr_2$. Any selective bromination conditions to convert methyl ketone to 1-bromoketone can be utilized to carry out the reaction of step (x').

The compound of formula LXX can be converted to the compound of formula LXXI via reaction of step (y') by treating the compound of formula LXX with the sodium salt of compound of formula XXVII in ethanol. Any conventional conditions can be utilized to carry out alkylation reaction.

The compound of formula LXXI is converted to the compound of formula LXXII via reaction of step (z') by de-esterification employing 4 equiv. of sodium hydroxide. This indicated an initial mono de-esterification followed by slow hydrolysis of the remaining ethyl ester. Removal of solvent and incubation of the residue in acetic acid produced the compound of formula LXXII.

The compound of formula LXXII is the compound of formula I' where $R^1$ is H.

The compound of formula LXXII can be converted to compound of formula LXXIII where $R^7$ is an alkyl group having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (a").

The compound of formula LXXIII is the compound of formula I' where $R^1$ is an alkyl group having 1 to 7 carbon atoms.

Scheme 8

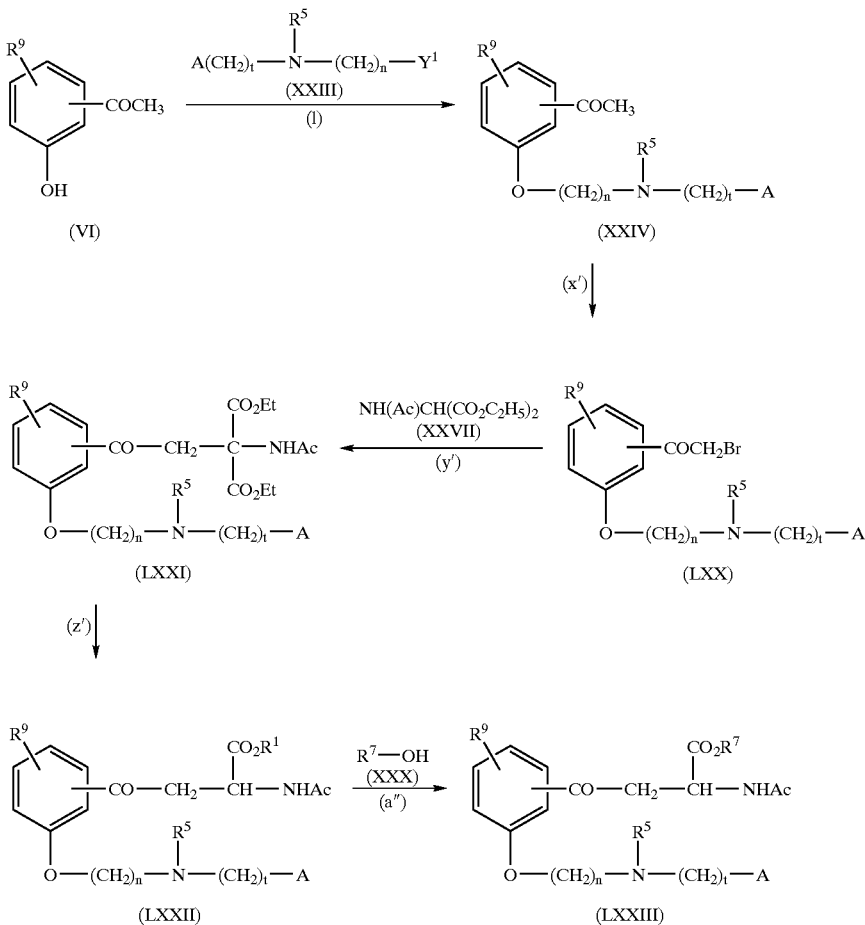

The compound of formula I' where X is —CH$_2$CH(NHAc)—, R$^9$ is hydrogen, halo, or alkoxy having 1 to 3 carbon atoms, Q is OR$^1$ where R$^1$ is hydrogen or alkyl having from 1 to 7 carbons, m is 1, q is 0, t is 0 or 1 and n is 1 or 2, i.e. compounds of the formula:

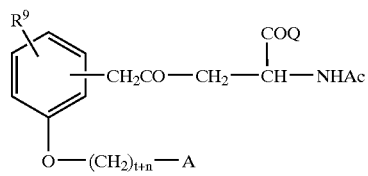

wherein A is as above, and R$^1$ is hydrogen or alkyl having from 1 to 7 carbon atoms can be prepared from the compound of formula LXXIV via the reaction scheme in Scheme 9.

In Scheme 9, t, n, A, R$^9$ and R$^1$ are as above. R$^7$ is an alkyl group having 1 to 7 carbon atoms. R$^5$ is an alkyl group having 1 to 3 carbon atoms.

The compound of formula LXXIV can be prepared according to method described in Murphy et al J.C.S. Perkin 1, 1980, 1555–1566.

The compound of formula LXXIV can be alkylated to produce compound of formula LXXV via reaction of step (b″) employing either compound of formula VII using same method as described in the connection of reaction step of (a) in Scheme 1 or compound of formula IX using potassium carbonate as the base for alkylation. The reaction is carried out in the same manner as described hereinbefore in connection with the reaction of step (l) in Scheme 4.

The compound of formula LXXV is then selectively brominated at 0° C. using 30 wt % HBr in acetic acid dropwise to produce compound of formula LXXVI via reaction of step (c″). Any conventional method to convert selectively substituted acetone to 1-Bromoacetone can be utilized to carry out this reaction of step (c″).

The compound of formula LXXVI is converted to compound of formula LXXVII via reaction of step (d″) in the same manner as described hereinbefore in connection with the reaction of step (o) in Scheme 5.

The compound of formula LXXVII is converted to compound of formula LXXVIII via reaction of step (e″) by de-esterification employing 4 equiv. of sodium hydroxide. Initial mono de-esterification followed by slow hydrolysis of the remaining ethyl ester was observed. Removal of solvent and incubation of the residue in acetic acid produced the compound of formula LXXVIII.

The compound of formula LXXVIII is the compound of formula I' where R$^1$ is H.

The compound of formula LXXVIII can be converted to compound of formula LXXIX where R$^7$ is an alkyl group having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (f″).

The compound of formula LXXIX is the compound of formula I' where R$^1$ is an alkyl group having 1 to 7 carbon atoms.

Scheme 9

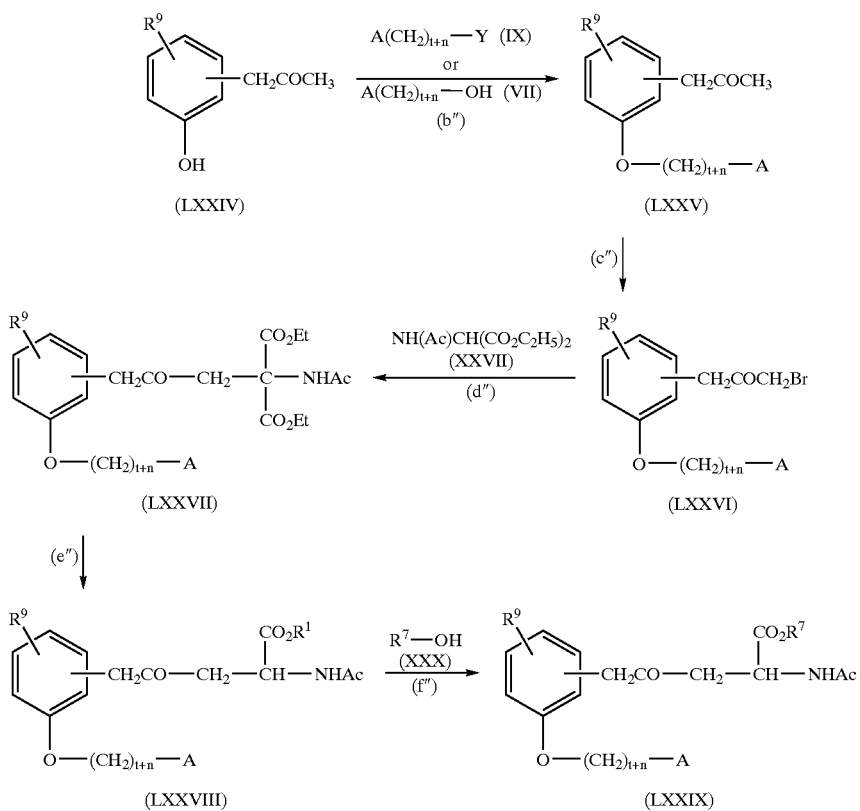

The compound of formula I' where q is 1, $R^5$ is an alkyl group having 1 to 3 carbon atoms, X is —$CH_2CH(NHAc)$—, m is 1, t is 0 or 1 and n is 1 or 2, $R^9$ is hydrogen, halo, or alkoxy having 1 to 3 carbon atoms, Q is $OR^1$ where $R^1$ is hydrogen or alkyl having from 1 to 7 carbons, i.e. compounds of the formula:

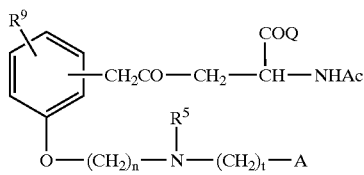

wherein A is as above, and $R^1$ is hydrogen or alkyl having from 1 to 7 carbon atoms can be prepared from the compound of the formula LXXIV via the reaction scheme in Scheme 10.

In Scheme 10, t, n, A, $R^9$ and $R^1$ are as above. $R^7$ is an alkyl group having 1 to 7 carbon atoms. $R^5$ is an alkyl group having 1 to 3 carbon atoms. $Y^1$ is chloro.

The compound of formula LXXIV can be prepared according to method described in Murphy et. al. J. C. S. Perkin 1, 1980, 1555–1566.

In Scheme 10, the compound of formula LXXIV is reacted with compound of formula XXIII (prepared in the same manner as described in Scheme 4) to produce the compound of formula LXXX via reaction of step (g"). This rection is carried out in the same manner as described hereinbefore in connection with the reaction of step (l) in Scheme 4.

The compound of formula LXXX is then selectively brominated at 0° C. using 30 wt % HBr in acetic acid dropwise to produce compound of formula LXXXI via reaction of step (h"). Any conventional method to convert substituted acetone to 1-Bromoacetone can be utilized to carry out the reaction of step (h").

The compound of formula LXXXI is converted to the compound of formula LXXXII via reaction of step (i") in the same manner as described hereinbefore in connection with the reaction of step (o) in Scheme 5.

The compound of formula LXXXII is converted to compound of formula LXXXIII via reaction of step (j") in the same manner as described in reaction of step (p) in Scheme 5.

The compound of formula LXXXIII is the compound of formula I' where $R^1$ is H.

The compound of formula LXXXIII can be converted to compound of formula LXXXIV where $R^7$ is an alkyl chain having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (k").

The compound of formula LXXXIV is the compound of formula I' where $R^1$ is an alkyl group having 1 to 7 carbon atoms.

Scheme 10

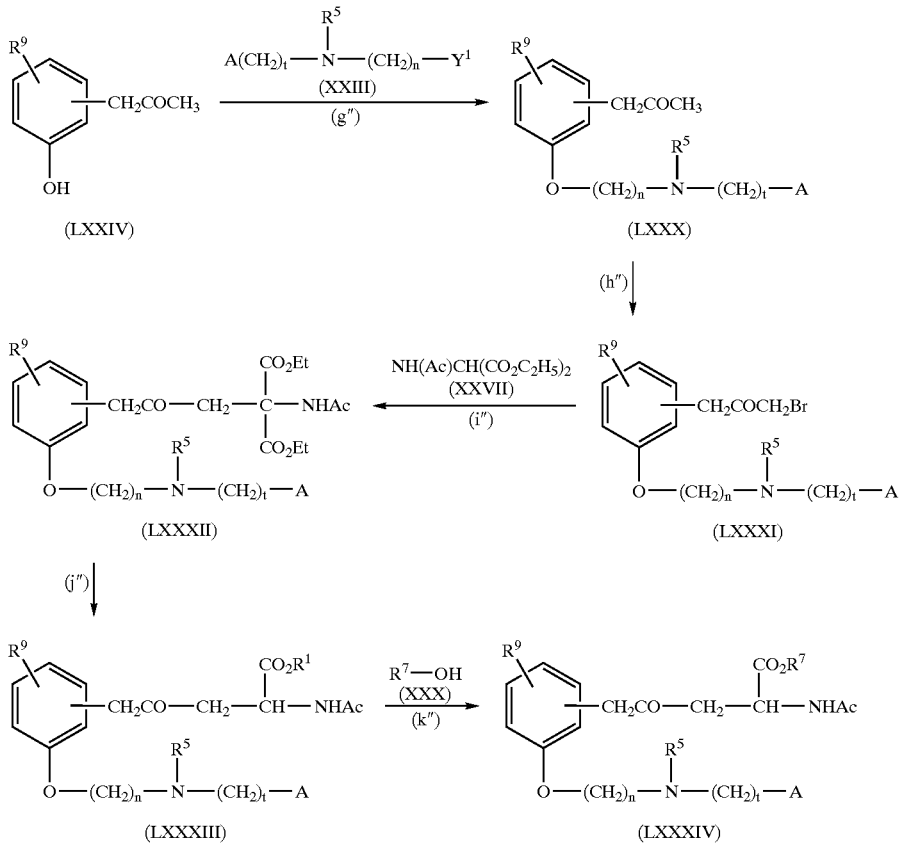

The compound of formula I' where X is —CH$_2$CR$^{12}$R$^{13}$—, R$^9$ is hydrogen, halo, or alkoxy having 1 to 3 carbon atoms, Q is OR$^1$ where R$^1$ is hydrogen or alkyl having from 1 to 7 carbons, q is 0, m is 1, t is 0 or 1 and n is 1 or 2, i.e. compounds of formula:

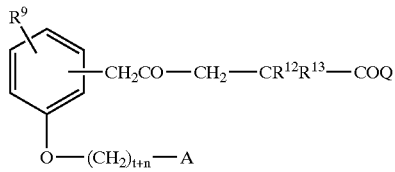

wherein A is as described above, R$^1$ is hydrogen or alkyl having from 1 to 7 carbon atoms, and R$^{12}$ and R$^{13}$ is independently hydrogen or methyl can be prepared from the compound of the formula LXXIV, via the reaction scheme in Scheme 11.

In the reaction scheme of Scheme 11, A, t, R$^9$, R$^{12}$, R$^{13}$ and n are as above. R$^6$ is an alkyl group containing from 1 to 7 carbon atoms, and Y is a leaving group.

The compound formula LXXV is produced from compound of formula LXXIV in the same manner as described hereinbefore in connection with the reaction of step (b") in Scheme 9.

The compound of formula LXXV is converted to compound of formula LXXXV via reaction of step (i") by selectively alkylating the compound of formula LXXV with the compound of formula X. This reaction is carried out utilizing a conventional base which converts substituted ketone to gamma-keto ester. In carrying out this reaction it is generally preferred to utilize lithium diisopropylamide as base. Alkylation will occur at the less hindered methyl group. Generally this reaction is carried out in an inert solvent such as tetrahydrofuran or 1,2-dimethoxyethane at −78° C.

The compound of formula LXXXV is the compound of formula I' where R$^1$ is an alkyl group containing from 1 to 7 carbon atoms. The compound of formula LXXXV can be converted to the free acid i.e. the compound of formula I' where R$^1$ is H by ester hydrolysis. Any conventional method of ester hydrolysis will produce the compound of formula I' where R$^1$ is H.

Scheme 11

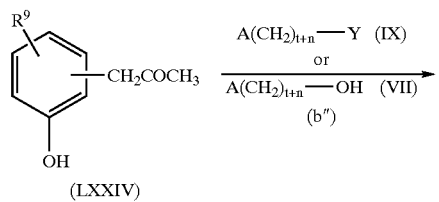

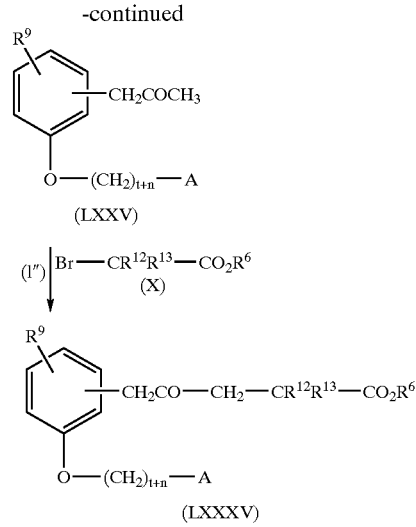

The compound of formula I where q is 1, R$^5$ is an alkyl group having 1 to 3 carbon atoms where X is —CH$_2$—, m is 1, t is 0 or 1 and n is 1 or 2, i.e. compounds of the formula:

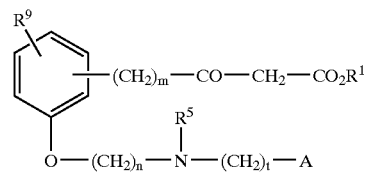

wherein A is as above, R$^9$ is hydrogen, halo, or alkoxy having 1 to 3 carbon atoms and R$^1$ is ethyl can be prepared from the compound formula XIII wherein, m is as above via the reaction scheme in Scheme 12.

In Scheme 12, A is as above. Y$^1$ is chloro.

The compound of formula XIII (prepared in the same manner as described hereinbefore in connection with the reaction of step (d) in Scheme 3) can be converted to compound of formula LXXXVI via reaction of step (m") in the same manner as described in the connection with reaction of step (l) in Scheme 4 hereinbefore.

In the step of (n"), the compound of formula LXXXVI is hydrolyzed to produce the compound of formula LXXXVII. Any conventional method of basic hydrolysis to hydrolyze ester can be utilized to carry out this reaction.

The compound of formula LXXXVII is converted to acid chloride of formula LXXXVIII via reaction of step (o") by reaction with thionyl chloride. Any of the conventional method of converting acid to acid halide can be utilized to carry out the reaction.

The compound of formula XVII is reacted with the compound of formula LXXXVIII to produce the compound of formula LXXXIX via reaction of step (p"). Any conventional base can be used to carry out this reaction with the preferred base being pyridine. Any conventional conditions to carry out the reaction of step (p") can be utilized.

The compound of formula LXXXIX is the compound of formula I where R$^1$ is ethyl.

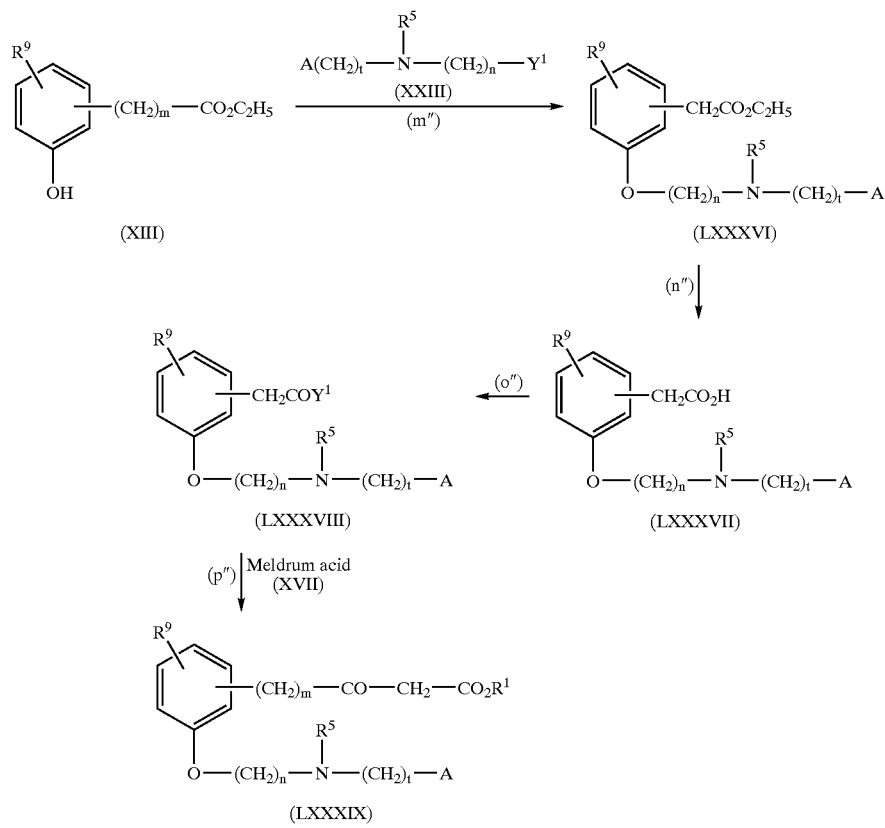

Scheme 12

The compound of formula I' where q is 1, $R^5$ is an alkyl group having 1 to 3 carbon atoms, where X is $-CH_2CR^{12}R^{13}-$, $R^9$ is hydrogen, halo, or alkoxy having 1 to 3 carbon atoms, Q is $OR^1$ where $R^1$ is hydrogen or alkyl having from 1 to 7 carbons, m is 1, t is 0 or 1 and n is 1 or 2, i.e. compounds of formula:

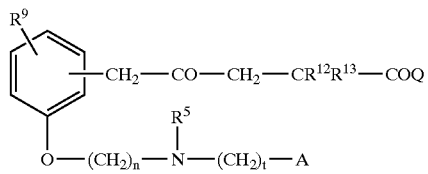

wherein A is as described above, $R^1$ is hydrogen or alkyl having from 1 to 7 carbon atoms, and $R^{12}$ and $R^{13}$ is independently hydrogen or methyl can be prepared from the compound of the formula LXXIV, via the reaction scheme in Scheme 13.

In the reaction scheme of Scheme 13, $R^9$, $R^{12}$, $R^{13}$, $R^5$, A, t, and n are as above. $R^6$ is an alkyl group containing from 1 to 7 carbon atoms.

The compound formula LXXX is produced from compound of formula LXXIV in the same manner as described hereinbefore in connection with the reaction of step (g") in Scheme 10.

The compound of formula LXXX is converted to compound of formula XC via reaction of step (q") by alkylating the compound of formula LXXX with the compound of formula X. This reaction is carried out utilizing a conventional base which converts ketone to 3-keto ester. In carrying out this reaction it is generally preferred to utilize lithium diisopropylamide as base. Alkylation will occur at the less hindered methyl group. Generally this reaction is carried out in an inert solvent such as tetrahydrofuran or 1,2-dimethoxyethane at −78° C.

The compound of formula XC is the compound of formula I' where $R^1$ is an alkyl group containing from 1 to 7 carbon atoms. The compound of formula XC can be converted to the free acid i.e. the compound of formula I' where $R^1$ is H by ester hydrolysis. Any conventional method of ester hydrolysis will produce the compound of formula I' where $R^1$ is H.

Scheme 13

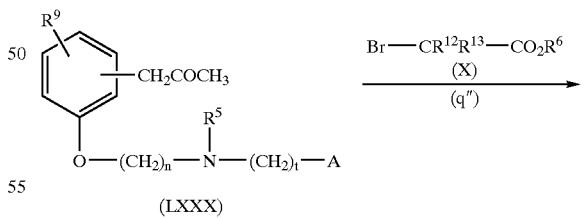

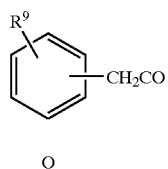

The compound of formula II where Z is

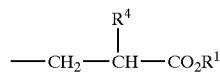

m is 0, r is 1, q is 0, t is 0 or 1 and n is 1 or 2, $R^4$ is —NHCO$_2$C(CH$_3$)$_3$, —NHCH$_3$, or —NHCH$_2$CH$_3$, i.e. the compounds of formula:

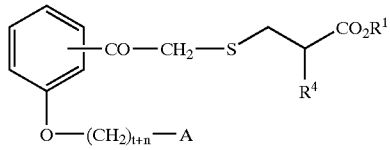

wherein A and $R^1$ are as above, can be prepared from the compound of formula XXVI via reaction scheme in Scheme 14.

In Scheme 14, t, n, A and $R^1$ are as above. $R^7$ is an alkyl group having 1 to 7 carbon atoms. $R^8$ is an alkyl group containing from 1 to 2 carbon atoms. $Y^1$ is halo preferably bromo.

In Scheme 14, the compound of formula XXVI (prepared in the same manner as described hereinbefore in connection with reaction of step (n) in Scheme 5) is reacted with the compound of formula XXXII in the presence of a base to produce the compound of formula XXXIII via reaction of step (r). In carrying out this reaction it is generally preferred to utilize triethylamine as base. Any conventional method of reacting Boc-cys-OEt with halide can be utilized to carry out this reaction.

The compound of formula XXXIII is compound of formula II where $R^4$ is —NHCO$_2$C(CH$_3$)$_3$ and $R^1$ is ethyl.

The compound of formula XXXIII can be converted to the free acid i.e. the compound of formula II where $R^1$ is H by ester hydrolysis. Any conventional method of ester hydrolysis will produce the compound of formula II where $R^1$ is H and $R^4$ is —NHCO$_2$C(CH$_3$)$_3$. The compound of formula XXXIII is converted to compound of formula XXXV first via reaction of step (s) by deprotecting t-butoxy group using trifluoroacetic acid and replacing by lower alkyl having 1 to 2 carbon atoms via reaction of step (t). Any conventional method to condense amine with alkyl halide can be used to carry out this reaction.

The compound of formula XXXV is compound of formula II where $R^4$ is an amine having 1 to 2 carbon atoms and $R^1$ is an alkyl group having 2 carbon atoms. The compound of formula XXXV can be converted to the free acid i.e. the compound of formula XXXVI where $R^1$ is H by basic hydrolysis via reaction of step (u). The compound of formula XXXVI is compound of formula II where $R^4$ is —NHCH$_3$ or —NHCH$_2$CH$_3$ and $R^1$ is H.

The compound of formula XXXVI can be converted to compound of formula XXXVII where $R^7$ is an alkyl group having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (v).

The compound of formula XXXVII is compound of formula II where $R^1$ is an alkyl having 1 to 7 carbon atoms and $R^4$ is —NHCH$_3$ or —NHCH$_2$CH$_3$.

Scheme 14

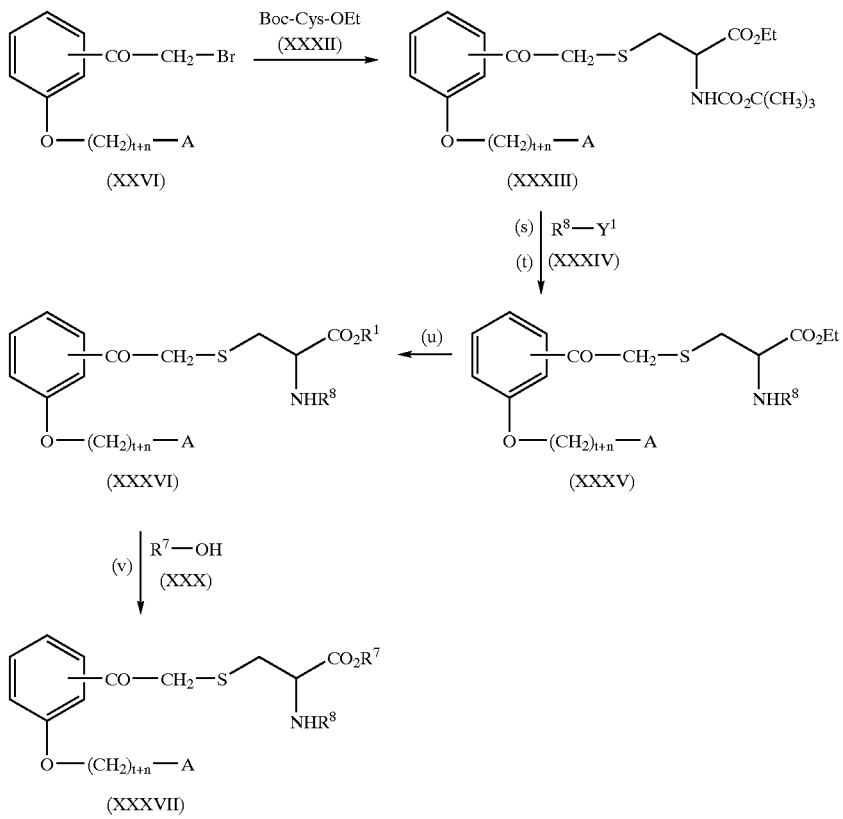

The compound of formula II where Z is

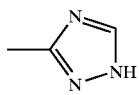

m and q are 0, r is 1, t is 0 or 1, n is 1 or 2, i.e. compounds of the formula:

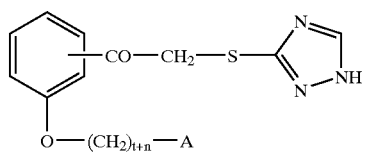

A is as above, can be prepared from the compound of formula VIII, wherein t, n and A are as above, via the reaction scheme in Scheme 15.

In Scheme 15, the compound of formula VIII (prepared in the same manner as described hereinbefore in connection with reaction of step (a) or (b) in Scheme 1) is converted to compound of formula XXVI in the same manner as described in reaction of step (n) in Scheme 5.

The compound of formula XXVI is reacted with compound of formula XXXVIII in the presence of base preferred base being triethylamine to produce the compound of formula XXXIX. Any conventional method to react thiol with halide can be utilized to carry out the reaction of step (w).

The compound of formula II where Z is

m is 0, r is 1, t is 0 or 1 and n is 1 or 2, $R^4$ is H, i.e. compounds of formula:

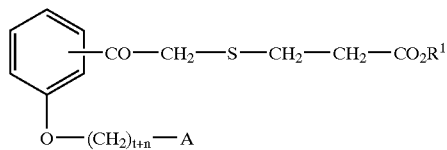

wherein t, n, A and $R^1$ are as above, can be prepared from the compound of formula VIII via the reaction scheme in Scheme 15.

In the reaction scheme of Scheme 15, t, n, A and $R^1$ are as above. $R^6$ is an alkyl group having 1 to 7 carbon atoms.

The compound of formula VIII is prepared in same manner as described hereinbefore in connection with the reaction of step (a) or (b) in Scheme 1.

The compound of formula XXVI is prepared from compound of formula VIII in the same manner as described hereinbefore in connection with the reaction of step (n) in Scheme 5.

The compound of formula XXVI is reacted with compound of formula XL in the presence of base preferred base being triethylamine to produce compound of formula XLI. Any conventional method to react thiol with 1-bromoketone can be utilized to carry out the reaction of step (x).

The compound of formula XLI is the compound of formula II where $R^1$ is an alkyl group containing from 1 to 7 carbon atoms. The compound of formula XLI can be converted to the free acid i.e. the compound of formula II where $R^1$ is H by ester hydrolysis. Any conventional method of ester hydrolysis will produce the compound of formula II where $R^1$ is H.

Scheme 15

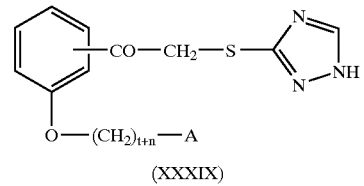

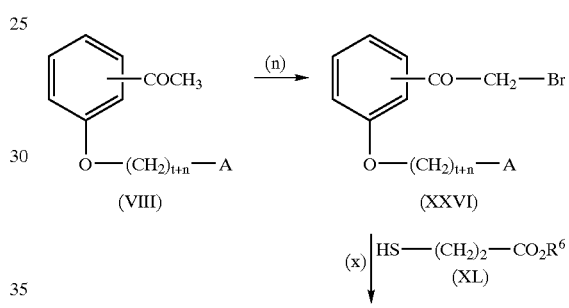

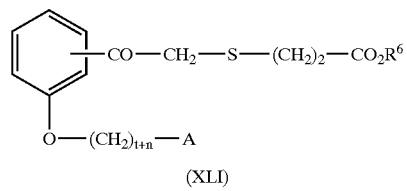

The compound of formula II where Z is

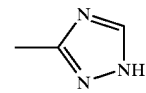

r is 0, m is 1, t is 0 or 1 and n is 1 or 2, i.e. compounds of formula:

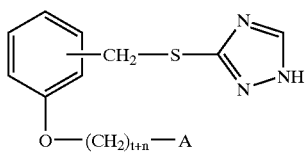

wherein n, t and A are as above, can be prepared from the compound of formula XLII via the reaction scheme in Scheme 16.

In Scheme 16, t, n, and A are as above. Y is a leaving group such as halide, mesyloxy or tosyloxy. $Y^1$ is halo preferably bromo.

In Scheme 16, the compound of formula XLII is converted to compound of formula XLIII via the reaction of step (y) by selective displacement of hydroxyl group of primary alcohol by halogen. Any conventional halogenating agent can be utilized to carry out this reaction with the preferred halogenating agent being phosphorous tribromide. This reaction is carried out in low temperature. Any conditions conventional for this method can be utilized to carry out the reaction of step (y). The compound of formula XLIII was used immediately without further purification.

The compound of formula XLIII is reacted with compound of formula XXXVIII in the presence of base to produce the compound of formula XLIV. Any conventional method of condensing thiol with halide can be utilized to carry out the reaction of step (z). Any conventional base can be utilized to carry out this reaction with the preferred base being triethylamine.

The compound of formula XLIV is converted to the compound of formula XLV by reaction with compound of formula VII via the reaction of step (a'). This reaction is carried out in the same manner as described hereinbefore in connection with reaction of step (a) in Scheme 1.

The compound of formula II where Z is

r is 0, m is 1, t is 0 or 1 and n is 1 or 2, $R^4$ is H, i.e. the compounds of formula:

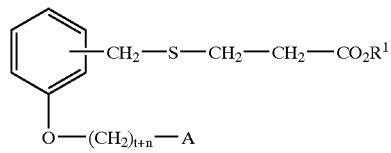

wherein A and $R^1$ are as above, can be prepared from the compound of formula XLII via the reaction scheme in Scheme 16.

In Scheme 16, t, n, and A are as above. Y is a leaving group such as halide, mesyloxy or tosyloxy. $Y^1$ is halo preferably bromo. $R^6$ is an alkyl group having 1 to 7 carbon atoms.

The compound of formula XLII is converted to compound of formula XLIII in the same manner as described hereinbefore in connection with the reaction of step (y).

The compound of formula XLIII is reacted with compound of formula XL via reaction of step (b') as described in connection with the reaction of step (x) in Scheme 15.

The compound of formula XLVI is converted to compound of formula XLVII via reaction of step (c'). This reaction is carried out in the same manner as described in the reaction of step (a) or (b) in Scheme 1.

The compound of formula XLVII is the compound of formula II where $R^1$ is an alkyl group containing from 1 to 7 carbon atoms. The compound of formula XLVII can be converted to the free acid i.e. the compound of formula II where $R^1$ is H by ester hydrolysis. Any conventional method of ester hydrolysis will produce the compound of formula II where $R^1$ is H.

Scheme 16

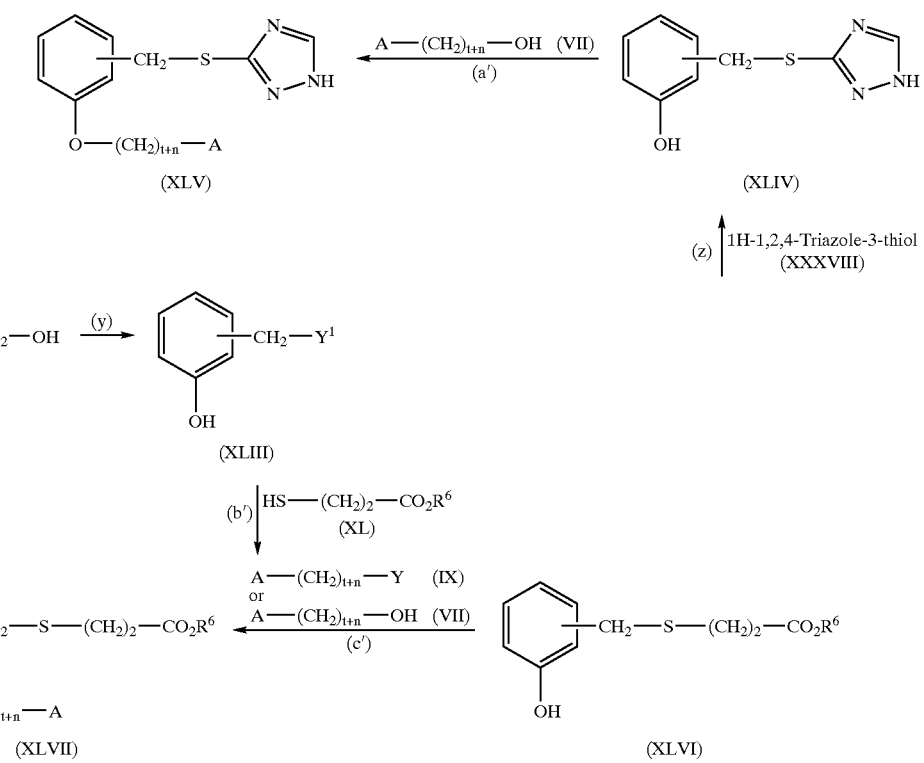

The compound of formula II where Z is

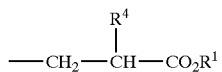

r is 0, m is 1, t is 0 or 1 and n is 1 or 2, i.e. compounds of formula:

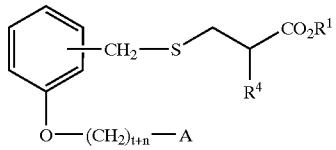

wherein t, n, A and $R^1$ are as above, $R^4$ is —$NHCO_2C(CH_3)_3$, —$NHCH_3$, —$NHCH_2CH_3$, can be prepared from the compound of formula XLIII via reaction scheme in Scheme 17.

In Scheme 17, t, n, A and $R^1$ are as above. Y is a leaving group such as halide, mesyloxy or tosyloxy. $R^7$ is an alkyl group having 1 to 7 carbon atoms and $R^8$ is an alkyl group containing from 1 to 2 carbon atoms. $Y^1$ is halo preferably bromo.

In Scheme 17, the compound of formula XLIII (prepared in the same manner as described hereinbefore in reaction of step (y) in Scheme 16) is reacted with the compound of formula XXXII in the presence of a base to produce the compound of formula XLVIII via reaction of step (d'). In carrying out this reaction it is generally preferred to utilize triethylamine as base. Any conventional method of reacting Boc-cyst-OEt with halide can be utilized to carry out this reaction.

The compound of formula XLIX is produced by reacting compound of formula XLVIII with compound of formula VII or IX. This reaction is carried out in the same manner as described in the reaction of step (a) or (b) in Scheme 1.

The compound of formula XLIX is compound of formula II where $R^4$ is —$NHCO_2C(CH_3)_3$ and $R^1$ is an alkyl group having 2 carbon atoms.

The compound of formula XLIX can be converted to the free acid i.e. the compound of formula II, where $R^1$ is H by ester hydrolysis. Any conventional method of ester hydrolysis will produce the compound of formula II where $R^1$ is H and $R^4$ is —$NHCO_2C(CH_3)_3$.

The compound of formula XLIX is converted to compound of formula L first via reaction of step (f') by de protecting t-butoxy group using trifluoroacetic acid and replacing by lower alkyl containing from 1 to 2 carbon atoms via reaction of step (g'). Any conventional method to condense amine with alkyl halide can be used to carry out this reaction.

The compound of formula L is compound of formula II where $R^4$ is
an amine having 1 to 2 carbon atoms and $R^1$ is an alkyl group having 2 carbon atoms.

The compound of formula L can be converted to the free acid i.e. the compound of formula LI where $R^1$ is H by basic hydrolysis via reaction of step (h').

The compound of formula LI is compound of formula II where $R^4$ is —$NHCH_3$ or —$NHCH_2CH_3$ and $R^1$ is H. Any conventional method of ester hydrolysis will produce the compound of formula II where $R^1$ is H.

The compound of formula LI can be converted to compound of formula LII where $R^7$ is an alkyl group having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (i').

The compound of formula LII is compound of formula II where $R^1$ is an alkyl group having 1 to 7 carbon atoms and $R^4$ is —$NHCH_3$ or —$NHCH_2CH_3$.

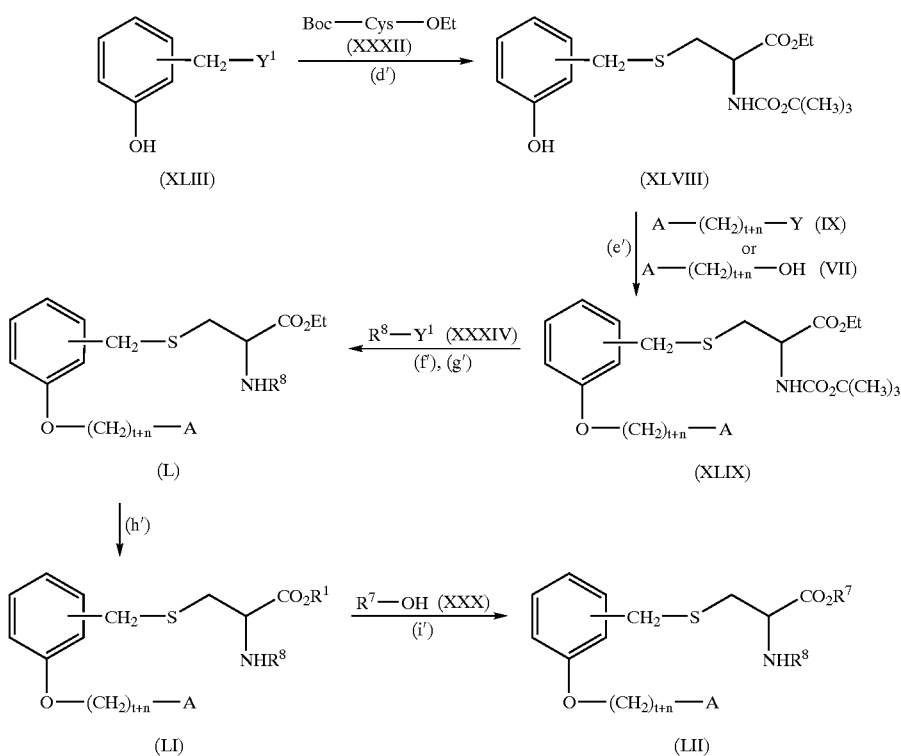

The compound of formula III

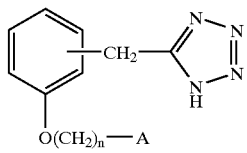

wherein n is 1 or 2 and A is as above, can be prepared from the compound of formula LIII, via reaction scheme in Scheme 18, wherein n, A and Y are as above.

In Scheme 18, the compound of formula LIII is converted to the compound of formula LIV in the same manner as described in connection with reaction of step (a) or (b) in Scheme 1.

The compound of formula LIV is converted to the compound of formula III via reaction of step (k') by heating the compound of formula LIV with sodium azide in the presence of ammonium chloride in dimethylformamide. Any conventional conditions to convert nitrile to terazole can be utilized to carry out this reaction.

Scheme 18

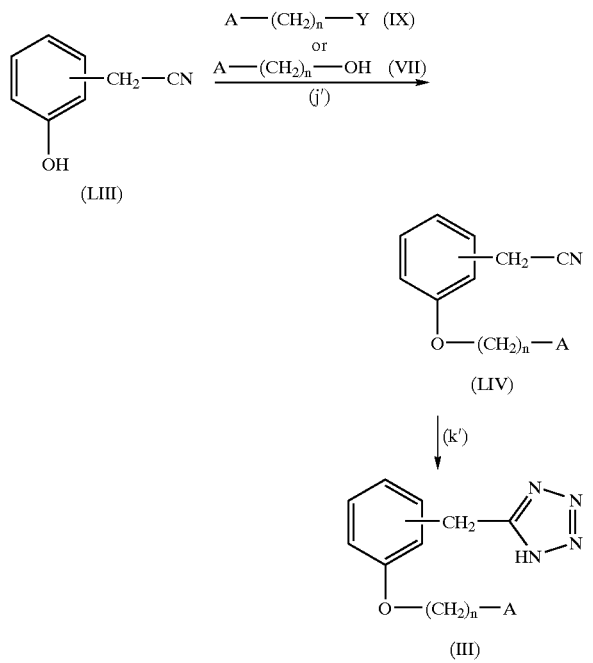

The compound of formula IV

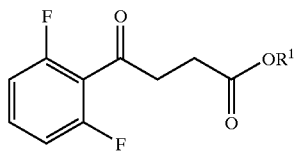

wherein $R^1$ is as above, can be prepared from 2',6'-difluoroacetophenone via reaction scheme in Scheme 19.

In Scheme 19, $R^6$ is an alkyl group having 1 to 7 carbon atoms.

The compound of formula LV is converted to compound of formula LVI via reaction of step (l') in same manner as described hereinbefore in connection with reaction of step (c) in Scheme 1.

The compound of formula LVI is the compound of formula IV where $R^1$ is an alkyl group having 1 to 7 carbon atoms. The compound of formula LVI can be converted to the free acid i.e. the compound of formula IV where $R^1$ is H by ester hydrolysis. Any conventional method of ester hydrolysis will produce the compound of formula IV where $R^1$ is H.

Scheme 19

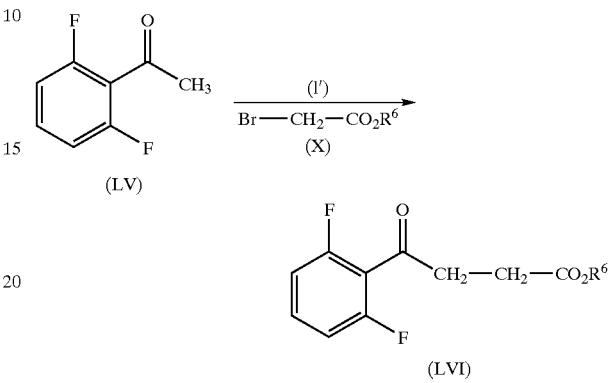

The compound of formula V

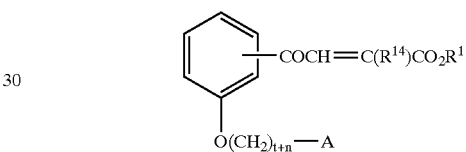

wherein n, A and $R^1$ are as above, $R^{14}$ is hydroxy can be prepared from the compound of formula VI, via reaction scheme in Scheme 20.

In Scheme 20, n, A are as above. Y is a leaving group such as halide, mesyloxy or tosyloxy. $R^7$ is an alkyl group having 1 to 7 carbon atoms and $R^8$ is an alkyl group having from 1 to 2 carbon atoms.

The compound of formula VI is converted to compound of formula VIII in same manner as described hereinbefore in connection with the reaction of step (a) or (b) of Scheme 1.

The compound of formula VIII is reacted with compound of formula LVII via reaction of step (m') in the presence of freshly prepared sodium alkoxide at room temperature to produce compound of formula LVIII. Any conventional conditions for this alkylation reaction can be utilized to carry out the reaction.

The compound of formula LVIII is the compound of formula V where $R^1$ is an alkyl group having 1 to 2 carbon atoms. The compound of formula LVIII can be converted to the free acid i.e. the compound of formula V where $R^1$ is H by ester hydrolysis via reaction of step (n'). Any conventional method of ester hydrolysis will produce the compound of formula V where $R^1$ is H.

The compound of formula LVIII can be converted to compound of formula LIX where $R^7$ is an alkyl group having 1 to 7 carbon atoms by esterification of carboxylic acid with compound of formula XXX using N,N-dicyclohexylcarbodiimide as dehydrating condensing agent. Any conditions conventional for this reaction can be utilized to carry out the reaction of step (o').

The compound of formula LIX is the compound of formula V where $R^1$ is an alkyl group having 1 to 7 carbon atoms.

Scheme 20

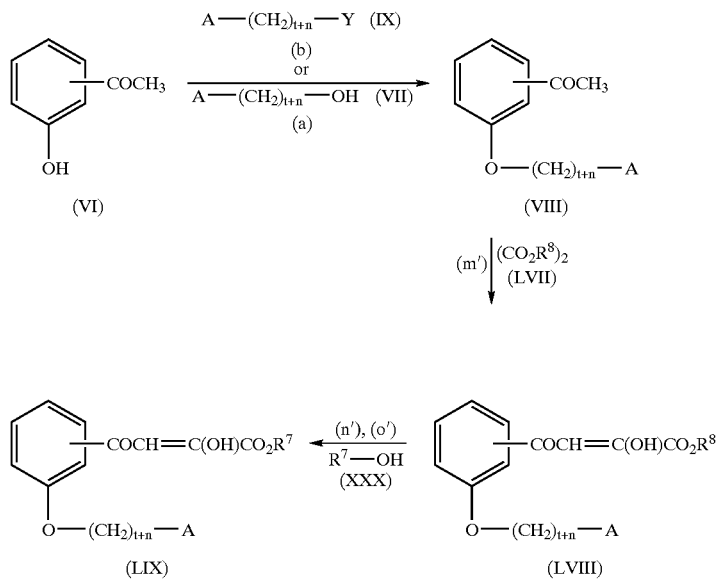

The compound of formula I' where X is —CH$_2$CH$_2$—, R$^9$ is hydrogen, halo, or alkoxy having 1 to 3 carbon atoms, q and m are 0, t is 0 or 1, and n is 1 or 2, i.e. compounds of formula:

XCII

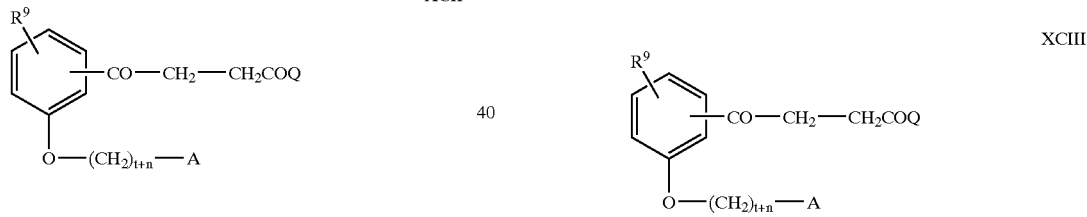

wherein Q is NR$^{10}$R$^{11}$ where R$^{10}$ is hydrogen and R$^1$ is hydroxyl group. t, n, A, and R$^9$ are as described above, can be prepared from the compound of the formula

XI

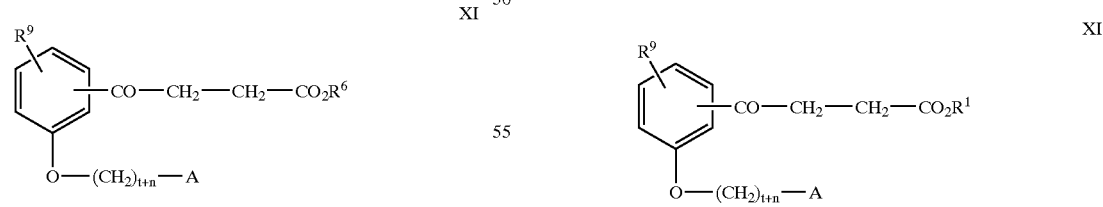

via the reaction scheme of Scheme 21.

In the reaction scheme 21, A, t, R$^9$, R$^6$ and n are as above.

The compound of formula XI is prepared in the same manner as described in the reaction scheme of Scheme 1.

The compound of formula XI can be converted to the compound of formula XCII via reaction step (s'') by treating the compound of formula XI with hydroxylamine hydrochloride in an organic solvent, for example ethanol, tetrahydrofuran or the like. The reaction is carried out using organic base for example, potassium hydroxide or the like. Any conditions conventional for the synthesis of hydroxamic acids can be utilized to carry out this reaction.

The compound of formula I' where X is —CH$_2$—CH$_2$—, q and m are 0, t is 0 or 1, and n is 1 or 2, R$^9$ is hydrogen, halo, or alkoxy having 1 to 3 carbon atoms, i.e. compounds of formula:

XCIII wherein t, n, A, and R$^9$ are described as above. Q is NR$^{10}$R$^{11}$ where R$^{10}$ and R$^{11}$ are hydrogen. can be prepared from the compound of the formula

XI via the reaction scheme in Scheme 21.

In the reaction scheme of Scheme 21, A, t, R$^9$ and n are as above. R$^1$ is H, R$^6$ is an alkyl having 1 to 7 carbon atoms.

The compound of formula XI is prepared in the same manner as described in the reaction scheme of Scheme 1. The compound of formula XI is the compound of formula I' where R$^1$ is an alkyl group containing from 1 to 7 carbon atoms. The compound of formula XI can be converted to the free acid i.e. the compound of formula I' where $R^1$ is H by ester hydrolysis.

The compound of formula XI can be converted to compound of formula XCIII via reaction step (t") by first activating by for example, benzotriazole-1-yloxytrispyrrolidinophosphonium hexafluorophosphate, or the like in an organic solvent, for example, methylene chloride, N,N-dimethylformamide or the like followed by addition of aqueous ammonium hydroxide or ammonia. The reaction is carried out using organic base for example, triethylamine, diisopropylethylamine or the like.

Any conditions conventional to synthesize amide can be utilized to carry out the reaction of step (t").

The compound of formula I' where X is $-CH_2-CH_2-$, q and m are 0, t is 0 or 1, and n is 1 or 2, $R^9$ is hydrogen, halo, or alkoxy having 1 to 3 carbon atoms, i.e. compounds of formula:

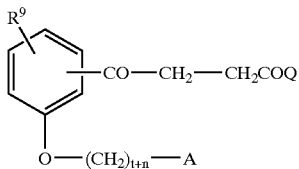

XCIV wherein t, n, A, and $R^9$ are described as above. Q is $NR^{10}R^{11}$ where $R^{10}$ and $R^{11}$ are independently hydrogen or alkyl having 1 to 3 carbon atoms.

can be prepared from the compound of the formula

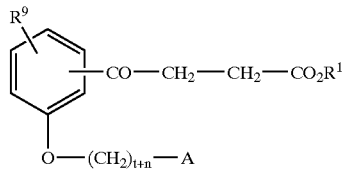

XI via the reaction scheme in Scheme 21.

In the reaction scheme of Scheme 21, A, t, $R^9$ and n are as above. $R^1$ is H and $R^6$ is an alkyl having 1 to 7 carbon atoms.

The compound of formula XI is prepared in the same manner as described in the reaction scheme of Scheme 1. The compound of formula XI is the compound of formula I' where $R^1$ is an alkyl group containing from 1 to 7 carbon atoms. The compound of formula XI can be converted to the free acid i.e. the compound of formula I' where $R^1$ is H by ester hydrolysis.

The compound of formula XI can be converted to the compound of formula XCIV either by first reacting with a chlorinating reagent for example, thionyl chloride or the like then reacting acid halide with corresponding amine. Any conventional method of condensing amine with an acid halide can be utilized to carry out the reaction of step (u") or by condensing corresponding amine with the compound of formula XI using 1,3-Dicyclohexylcarbodiimide as condensing agent.

Any conventional method of condensing amine with an acid can be utilized to carry out the reaction of step (u").

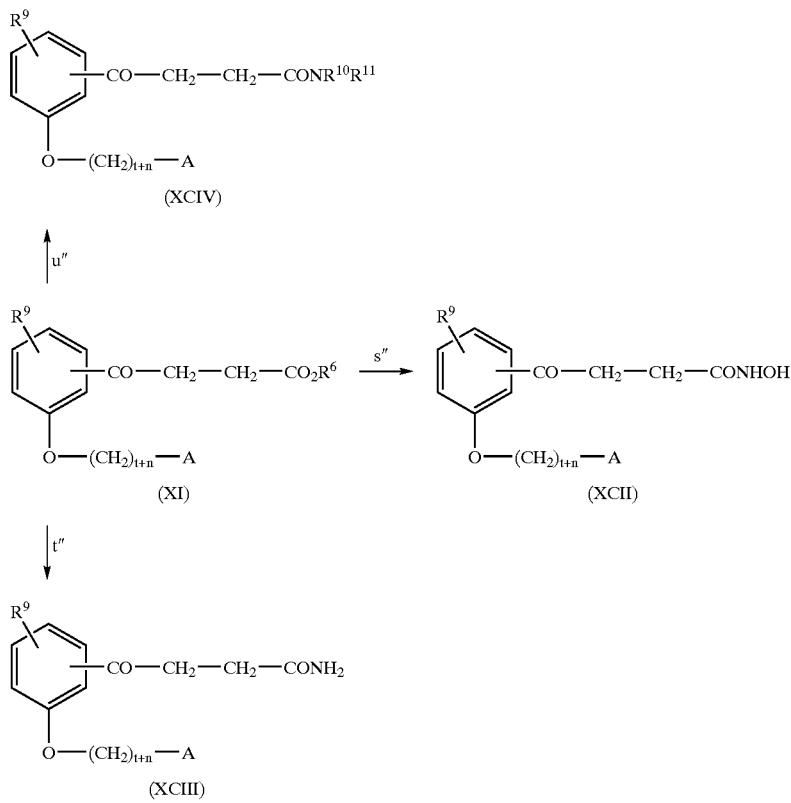

Scheme 21

The compound of formula I' where X is —CH$_2$—CH$_2$—, q is 1, R$^5$ is an alkyl group having 1 to 3 carbon atoms, R$^9$ is hydrogen, halo, or alkoxy having 1 to 3 carbon atoms, m is 0, t is 0 or 1, and n is 1 or 2, i.e. compounds of formula:

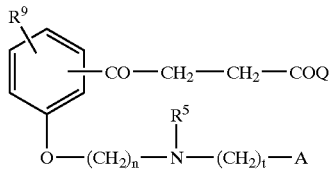

XCV wherein Q is NR$^{10}$R$^{11}$ where R$^{10}$ is hydrogen and R$^{11}$ is hydroxyl group. A, t, n, and R$^9$ are as described above, can be prepared from the compound of the formula

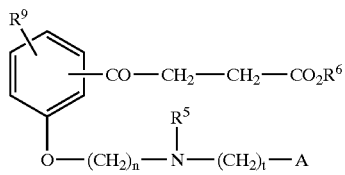

XXV via the reaction scheme in Scheme 22.

In the reaction scheme 22, q, A, t, R$^5$, R$^9$ and n are described as above. R$^6$ is an alkyl having 1 to 7 carbon atoms.

The compound of formula XXV is prepared in the same manner as described in the reaction scheme of Scheme 4.

The compound of formula XXV can be converted to the compound of formula XCV via reaction step (v") in the same manner as described in reaction step (s") of Scheme 21.

The compound of formula I' where X is —CH$_2$—CH$_2$—, q is 1, R$^5$ is an alkyl group having 1 to 3 carbon atoms, R$^9$ is hydrogen, halo, or alkoxy having 1 to 3 carbon atoms, m is 0, t is 0 or 1, and n is 1 or 2, R$^1$ is H, i.e. compounds of formula:

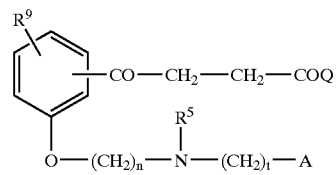

XCVI wherein q, t, n, A, R$^5$ and R$^9$ are described as above. Q is NR$^{10}$R$^{11}$ where R$^{10}$ and R$^{11}$ are hydrogen and can be prepared from the compound of the formula

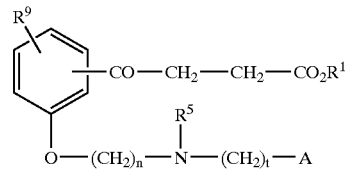

XXV via the reaction scheme in Scheme 22.

In the reaction scheme of Scheme 22, q, A, t, R$^5$, R$^9$ and n are as above. R$^1$ is H and R$^6$ is an alkyl having 1 to 7 carbon atoms.

The compound of formula XXV is prepared in the same manner as described in the reaction scheme of Scheme 4. The compound of formula XXV is the compound of formula I' where R$^1$ is an alkyl group containing from 1 to 7 carbon atoms. The compound of formula XXV can be converted to the free acid i.e. the compound of formula I' where R$^1$ is H by ester hydrolysis.

The compound of formula XXV can be converted to the compound of formula XCVI via reaction step (w") in the same manner as described in step (t") of reaction scheme 21.

The compound of formula I' where X is —CH$_2$—CH$_2$—, q is 1, R$^5$ is an alkyl group having 1 to 3 carbon atoms, R$^9$ is hydrogen, halo, or alkoxy having 1 to 3 carbon atoms, m is 0, t is 0 or 1, and n is 1 or 2, i.e. compounds of formula:

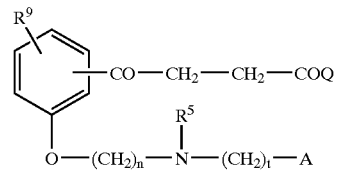

XCVII wherein q, t, n, A, R$^5$ and R$^9$ are as described above, Q is NR$^{10}$R$^{11}$ where R$^{10}$ and R$^{11}$ are independently hydrogen or alkyl having 1 to 3 carbon atoms.
can be prepared from the compound of the formula

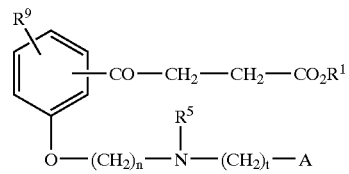

XXV via the reaction scheme in Scheme 22.

In the reaction scheme 22, q, A, t, R$^5$, R$^9$ and n are as above. R$^6$ is an alkyl having 1 to 7 carbon atoms. R$^1$ is H.

The compound of formula XXV is prepared in the same manner as described in the reaction scheme of Scheme 4. The compound of formula XXV is the compound of formula I' where R$^1$ is an alkyl group containing from 1 to 7 carbon atoms. The compound of formula XXV can be converted to the free acid i.e. the compound of formula I' where R$^1$ is H by ester hydrolysis.

The compound of formula XXV can be converted to the compound of formula XCVII via reaction step (x") in the same manner as described in step (u") of reaction scheme 21.

Scheme 22

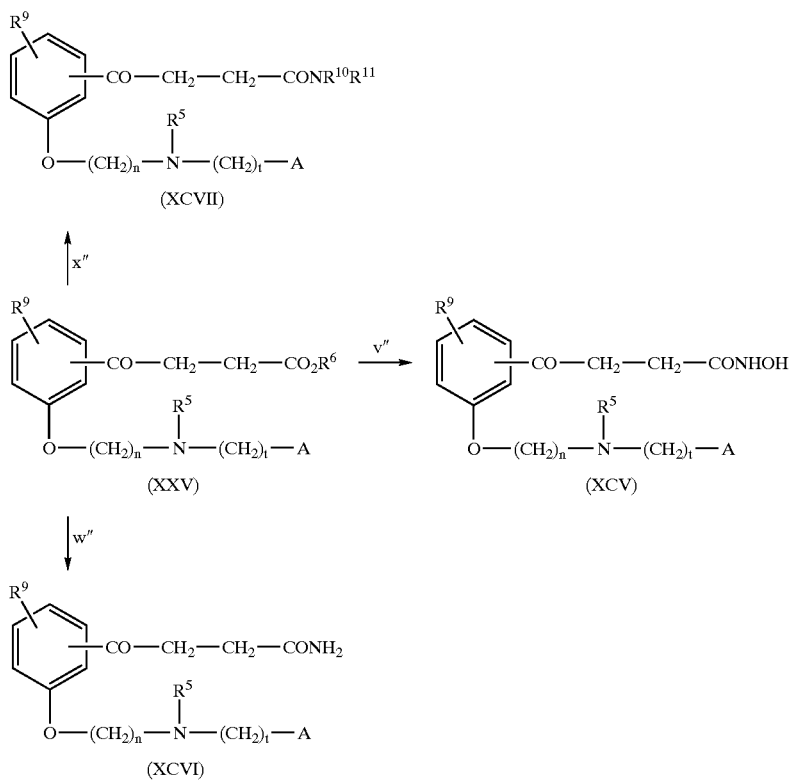

The compound of formula I' where X is —CH$_2$—CH$_2$—, R$^9$ is hydrogen, halo, or alkoxy having 1 to 3 carbon atoms, m is 1, q is 0, t is 0 or 1 and n is 1 or 2, i.e. compounds of the formula:

XCVIII

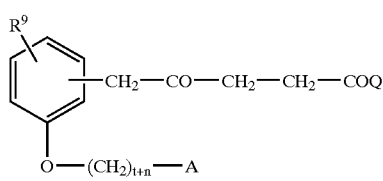

wherein Q is NR$^{10}$R$^{11}$ where R$^{10}$ is hydrogen, R$^{11}$ is hydroxyl group. t, n, A, and R$^9$ are as described above, can be prepared from the compound of the formula

LXXXV

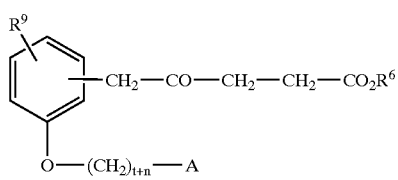

via the reaction scheme in Scheme 23.

In the reaction scheme 23, A, t, R$^9$ and n are as described above. R$^6$ is an alkyl having 1 to 7 carbon atoms.

The compound of formula LXXXV is prepared in the same manner as described in the reaction scheme of Scheme 11.

The compound of formula LXXXV can be converted to the compound of formula XCVIII via reaction step (y'') in the same manner as described in reaction step (s'') of Scheme 21.

The compound of formula I' where X is —CH$_2$—CH$_2$—, R$^9$ is hydrogen, halo, or alkoxy having 1 to 3 carbon atoms, m is 1, q is 0, t is 0 or 1 and n is 1 or 2, i.e. compounds of the formula:

XCIX

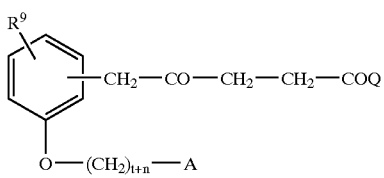

wherein t, n, A, and R$^9$ are described as above. Q is NR$^{10}$R$^{11}$ where R$^{10}$ and R$^{11}$ are hydrogen.

can be prepared from the compound of the formula

LXXXV

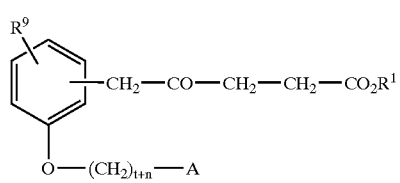

via the reaction scheme in Scheme 23.

In the reaction scheme of Scheme 23, A, t, $R^5$, $R^9$ and n are as above. $R^1$ is H. $R^6$ is an alkyl having 1 to 7 carbon atoms.

The compound of formula LXXXV is prepared in the same manner as described in the reaction scheme of Scheme 11. The compound of formula LXXXV is the compound of formula I' where $R^1$ is an alkyl group containing from 1 to 7 carbon atoms. The compound of formula LXXXV can be converted to the free acid i.e. the compound of formula I' where $R^1$ is H by ester hydrolysis.

The compound of formula LXXXV can be converted to the compound of formula XCIX via reaction step (z") in the same manner as described in reaction step (t") of reaction scheme 21.

The compound of formula I' where X is —$CH_2$—$CH_2$—, $R^9$ is hydrogen, halo, or alkoxy having 1 to 3 carbon atoms, m is 1, q is 0, t is 0 or 1 and n is 1 or 2, i.e. compounds of the formula:

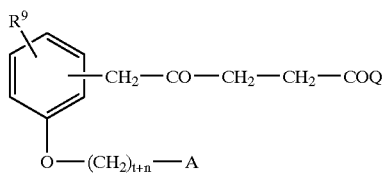

C wherein t, n, A, and $R^9$ are as described above, Q is $NR^{10}R^{11}$ where $R^{10}$ and $R^{11}$ are independently hydrogen or alkyl having 1 to 3 carbon atoms.

can be prepared from the compound of the formula

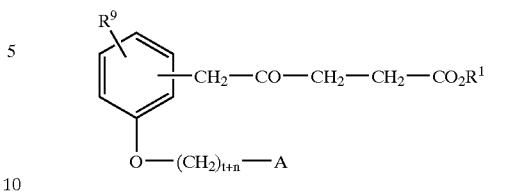

LXXXV via the reaction scheme in Scheme 23.

In the reaction scheme 23, A, t, $R^9$ and n are as above. $R^1$ is H. $R^6$ is an alkyl having 1 to 7 carbon atoms.

The compound of formula LXXXV is prepared in the same manner as described in the reaction scheme of Scheme 11. The compound of formula LXXXV is the compound of formula I' where $R^1$ is an alkyl group containing from 1 to 7 carbon atoms. The compound of formula LXXXV can be converted to the free acid i.e. the compound of formula I' where $R^1$ is H by ester hydrolysis.

The compound of formula LXXXV can be converted to the compound of formula C via reaction step (a''') in the same manner as described in step (u") of reaction scheme 21.

Scheme 23

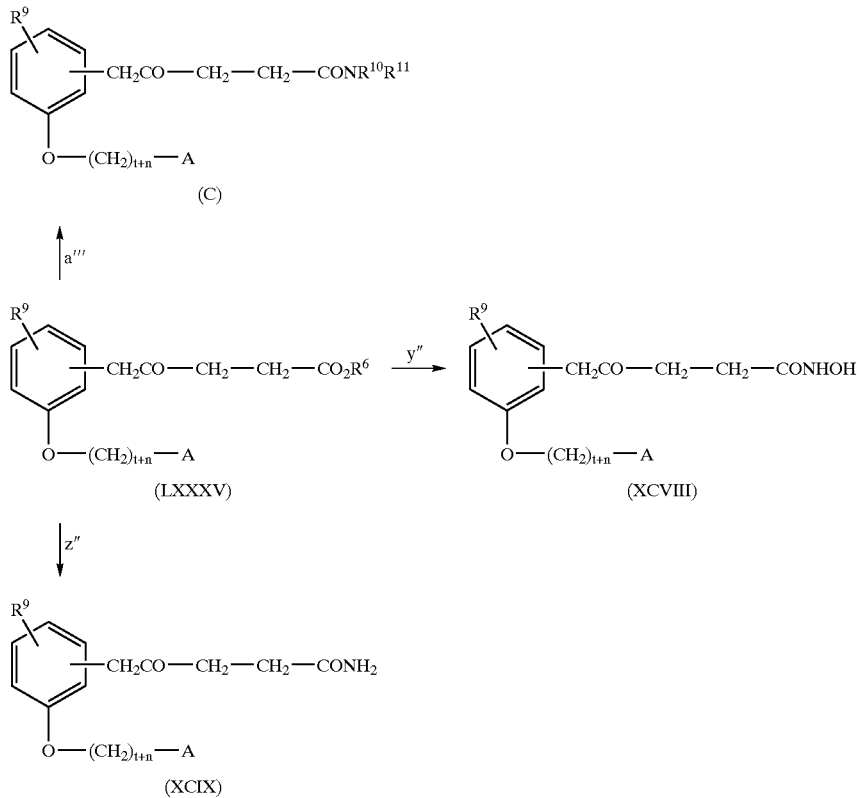

The compound of formula I' where X is —CH$_2$—CH$_2$—, R$^9$ is hydrogen, halo, or alkoxy having 1 to 3 carbon atoms, q is 1, R$^5$ is an alkyl group having 1 to 3 carbon atoms, m is 1, t is 0 or 1, and n is 1 or 2, i.e. compounds of formula:

CII

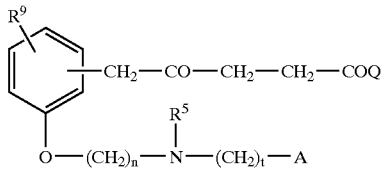

wherein Q is NR$^{10}$R$^{11}$ where R$^{10}$ is hydrogen and R$^{11}$ is hydroxyl group. t, n, A, R$^5$ and R$^9$ are as described above, can be prepared from the compound of the formula

XC

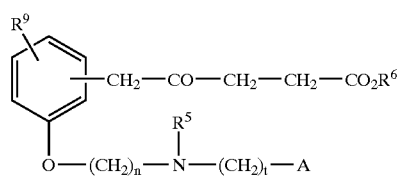

via the reaction scheme in Scheme 24.

In the reaction scheme 24, q, A, t, n, R$^5$, R$^9$, and R$^6$ are described as above.

The compound of formula XC is prepared in the same manner as described in the reaction scheme of Scheme 13.

The compound of formula XC can be converted to the compound of formula CII via reaction step (b''') in the same manner as described in reaction step (s'') of Scheme 21.

The compound of formula I' where X is —CH$_2$—CH$_2$—, R$^9$ is hydrogen, halo, or alkoxy having 1 to 3 carbon atoms, q is 1, R$^5$ is an alkyl group having 1 to 3 carbon atoms, m is 1, t is 0 or 1, and n is 1 or 2, i.e. compounds of formula:

CIII

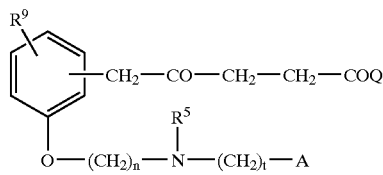

wherein q, t, n, A, R$^5$ and R$^9$ are described as above. Q is NR$^{10}$R$^{11}$ where R$^{10}$ and R$^{11}$ are hydrogen.
can be prepared from the compound of the formula

XC

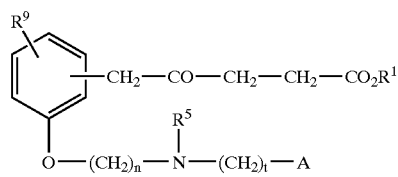

via the reaction scheme in Scheme 24.

In the reaction scheme of Scheme 24, q, A, t, R$^5$, R$^9$ and n are as above. R$^1$ is H. R$^6$ is an alkyl having 1 to 7 carbon atoms.

The compound of formula XC is prepared in the same manner as described in the reaction scheme of Scheme 13. The compound of formula XC is the compound of formula I' where R$^1$ is an alkyl group containing from 1 to 7 carbon atoms. The compound of formula XC can be converted to the free acid i.e. the compound of formula I' where R$^1$ is H by ester hydrolysis.

The compound of formula XC can be converted to the compound of formula CIII via reaction step (c''') in the same manner as described in step (t'') of reaction scheme 21.

The compound of formula I' where X is —CH$_2$—CH$_2$—, R$^9$ is hydrogen, halo, or alkoxy having 1 to 3 carbon atoms, q is 1, R$^5$ is an alkyl group having 1 to 3 carbon atoms, m is 1, t is 0 or 1, and n is 1 or 2, i.e. compounds of formula:

CIV

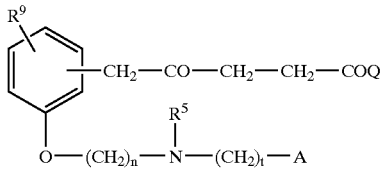

wherein q, t, n, A, R$^5$ and R$^9$ are as described above, Q is NR$^{10}$R$^{11}$ where R$^{10}$ and R$^{11}$ are independently hydrogen or alkyl having 1 to 3 carbon atoms.

can be prepared from the compound of the formula

XC

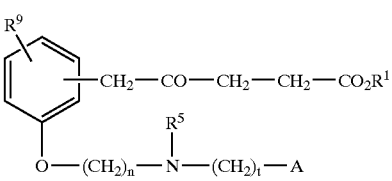

via the reaction scheme in Scheme 24.

In the reaction scheme 24, q, A, t, R$^5$, R$^9$ and n are as above. R$^1$ is H. R$^6$ is an alkyl having 1 to 7 carbon atoms.

The compound of formula XC is prepared in the same manner as described in the reaction scheme of Scheme 13. The compound of formula XC is the compound of formula I' where R$^1$ is an alkyl group containing from 1 to 7 carbon atoms. The compound of formula XC can be converted to the free acid i.e. the compound of formula I' where R$^1$ is H by ester hydrolysis.

The compound of formula XC can be converted to the compound of formula CIV via reaction step (d''') in the same manner as described in step (u'') of reaction scheme 21.

Scheme 24

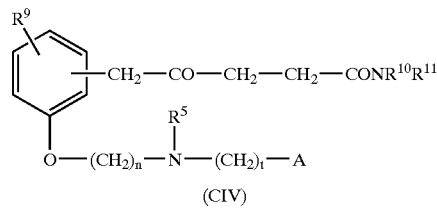

-continued

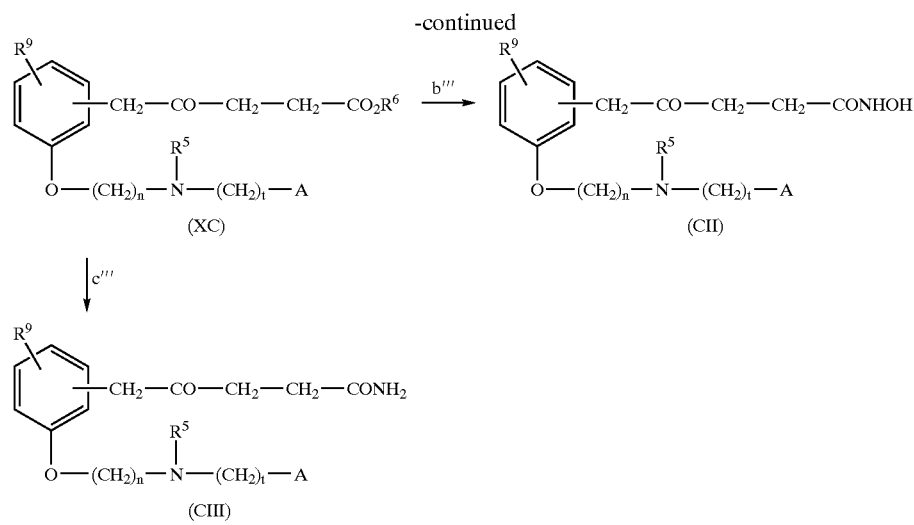

The compound of formula V' where n is 1 or 2, t is 0, $R^1$, $R^9$ and $R^{14}$ are H, i.e. compounds of formula:

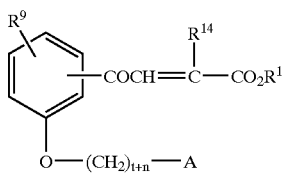

CVI wherein t, n, A, $R^9$, $R^{14}$ and $R^1$ are as described above, can be prepared from the compound of the formula

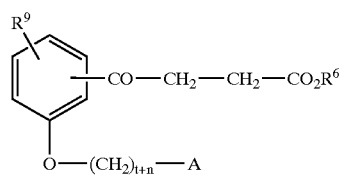

XI via the reaction scheme in Scheme 25.

In the reaction scheme of Scheme 25, A, t, and n are as above. $R^6$ is an alkyl group containing from 1 to 7 carbon atoms.

The compound of formula XI is prepared in the same manner as described in the reaction scheme of Scheme 1.

The compound of formula XI can be converted to compound of formula CV via reaction step (e'''), by treating the compound of formula XI with bromine or the like in an organic solvent, for example ether, carbon tetrachloride with the preferred organic solvent being ether.

As the reaction temperature, ice cooling to room temperature can be used with the preferred being ice cooling.

The compound of formula CV can be converted to the compound of formula CVI via reaction step (f'''), by dehydrobromination. The reaction is carried out using conventional base preferred base being triethylamine or the like in an organic solvent for example carbon tetrachloride or the like. Any of the conditions conventional in dehydrobromination can be utilized to carry out the reaction of step (f'').

The compound of formula CVI is the compound of formula V' where $R^1$ is an alkyl group containing from 1 to 7 carbon atoms. The compound of formula CVI can be converted to the free acid i.e. the compound of formula V' where $R^1$ is H by ester hydrolysis. Any conventional method of ester hydrolysis will produce the compound of formula V' where $R^1$ is H.

Scheme 25

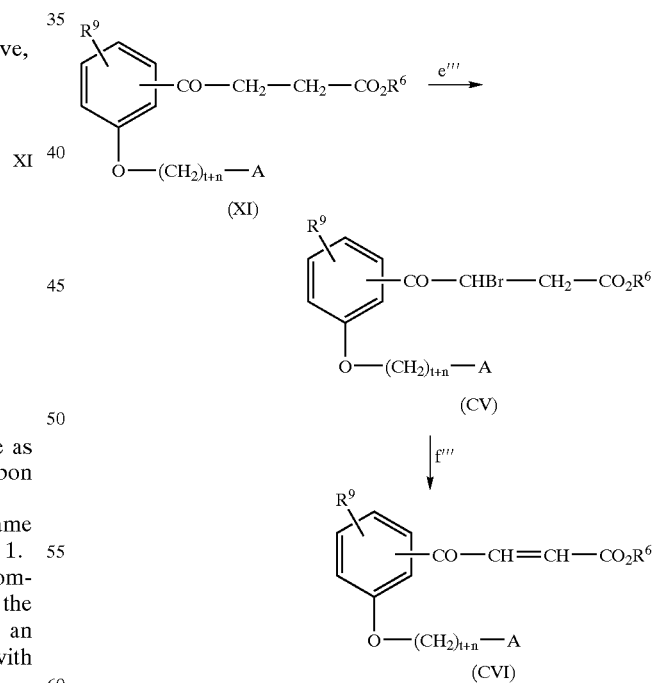

The compound of formula CXVI where X is —$CH_2$—$CH_2$—, t is 0 or 1, and n is 1 or 2, $R^1$ and $R^9$ are H, i.e. compounds of formula:

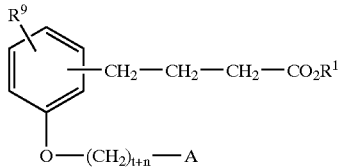

CVII wherein t, n, A, and $R^9$ are as described above, $R^1$ is H. can be prepared from the compound of the formula

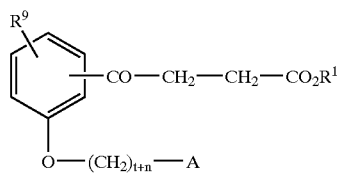

XI via the reaction scheme in Scheme 26.

In the reaction scheme of 26, A, t, n and $R^9$ are as above. $R^1$ is H. $R^6$ is an alkyl group having 1 to 7 carbon atoms.

The compound of formula XI is prepared in the same manner as described in the reaction scheme of Scheme 1. The compound of formula XI is the compound of formula I' where $R^1$ is an alkyl group containing from 1 to 7 carbon atoms. The compound of formula XI can be converted to the free acid i.e. the compound of formula I' where $R^1$ is H by ester hydrolysis. Any conventional method of ester hydrolysis will produce the compound of formula I' where $R^1$ is H.

The compound of formula XI is converted to compound of formula CVII via reaction step (g''') via Wolff-Kishner reduction by treating the compound of formula XI with hydrazine hydrate and potassium hydroxide in an organic solvent for example, ethylene glycol or the like. Any of the conditions conventional in Wolff-Kishner reductions can be utilized to carry out the reaction of step (g''').

Scheme 26

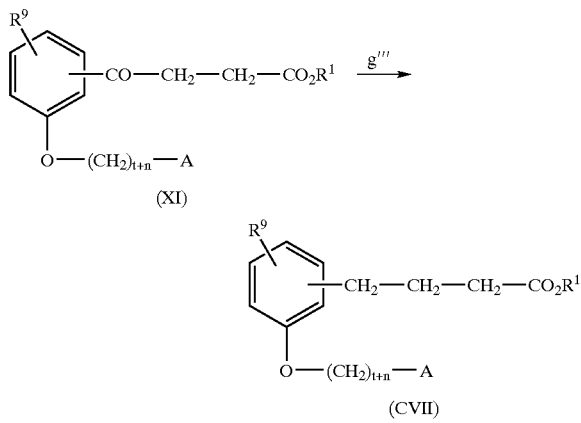

The compound of formula XCI where n is 1 or 2, $R^9$ is H and $R^1$ is hydrogen or alkyl having 1 to 3 carbon atoms, i.e. compounds of formula:

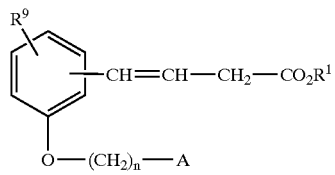

CX wherein n, A, $R^9$ and $R^1$ are as described above, can be prepared from the compound of the formula

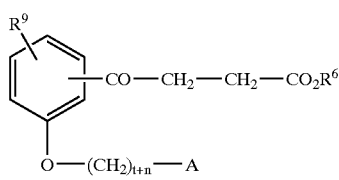

XI via the reaction scheme in Scheme 27.

In the reaction scheme of Scheme 27, $R^9$ is a hydrogen atom, t is 0, $R^6$ is an alkyl having 1 to 7 carbon atoms, A and n are as described above.

The compound of formula XI is prepared in the same manner as described in the reaction scheme of Scheme 1.

The compound of formula XI can be converted to the compound of formula CVIII via reaction step (h''') by selectively reducing ketone group to an alcohol. This reaction is carried out utilizing conventional reducing agents for example, sodium borohydride in ethanol, Bis-3-methyl-2-butyl-borane in tetahydrofuran or the like. Any of the conditions conventional in such selective reduction reactions can be utilized to carry out the reaction of step (h''').

The compound of formula CVIII can be converted to compound of formula CIX via reaction step (i''') by bromination of compound of formula CVIII with brominating reagents for example, phosphorous tribromide in tetrahydrofuran or dioxane, hydrogen bromide in acetic acid or dioxane, carbon tetrabromide and bis-(1,2-diphenylphosphino)ethane or the like. Any of the conditions conventional in such bromination reactions can be utilized to carry out the reaction of step (i''').

The compound of formula CIX can be converted to the compound of formula CX via reaction step (j'''), by dehydrobromination. The reaction is carried out using conventional base preferred base being triethylamine or the like in an organic solvent for example carbon tetrachloride or the like. Any of the conditions conventional in such dehydrobromination reactions can be utilized to carry out the reaction of step (j''').

The compound of formula CX is the compound of formula XCI where $R^1$ is an alkyl group containing from 1 to 3 carbon atoms. The compound of formula CX can be converted to the free acid i.e. the compound of formula XCI where $R^1$ is H by ester hydrolysis. Any conventional method of ester hydrolysis will produce the compound of formula XCI where $R^1$ is H.

Scheme 27

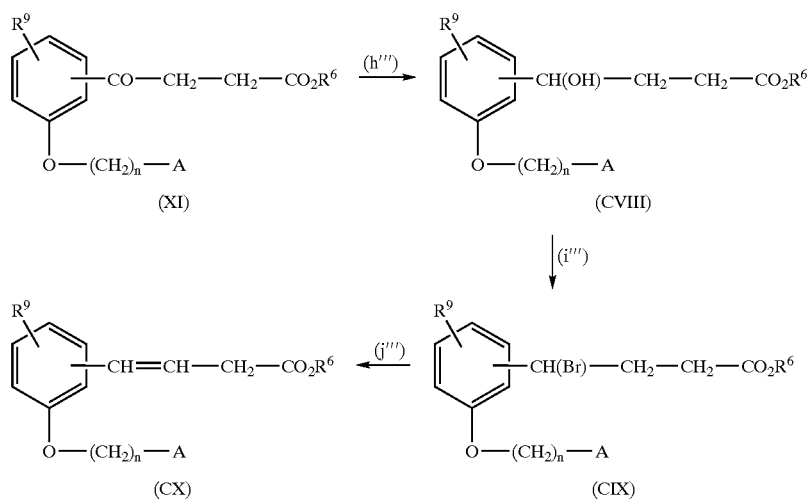

The compound of formula CXVII where X is —CH$_2$—CH$_2$—, and n is 0 or 2, R$^{15}$ is a hydrogen or lower alkyl group having 1 to 3 carbon atoms, R$^9$ is hydroxy, hydrogen, alkoxy group having 1 to 3 carbon atoms, halogen atom, R$^1$ is hydrogen or alkyl having 1 to 3 carbon atoms, i.e. compounds of formula:

CXIV

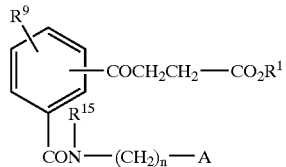

wherein n, A, R$^9$ and R$^{15}$ are as described above, can be prepared by reacting the compound of the formula

CXI

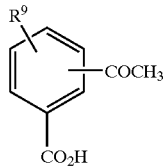

with compound of formula

CXII

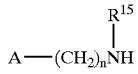

via the reaction scheme in Scheme 28.

In the reaction scheme of Scheme 28, A, n, R$^9$, R$^{15}$ are described as above, R$^6$ is an alkyl having 1 to 3 carbon atoms.

The compound of formula CXI can be converted to compound of formula CXIII via reaction step (k''') by treating compound of formula CXI with condensing agent, for example diethyl cyanophosphate, 1-ethyl-3-(3'-dimethylaminopropyl)carbodiimide or the like in an organic solvent, for example, methylene chloride, N,N-dimethylformamide followed by addition of compound of formula CXII.

The reaction temperature can be from 0° C. to room temperature.

The compound of formula CXIII can be converted to the compound of formula CXIV via reaction of step (l''') by alkylating the compound of formula CXIII with the compound of formula X. This reaction is carried out in the same manner as described in the reaction step (c) of reaction scheme 1.

The compound of formula CXIV is the compound of formula CXVII where R$^9$ is an alkoxy group having 1 to 3 carbon atoms, halogen atom. The R$^9$ can be converted to hydroxy via demethylation by using for example, boron tribromide in methylene chloride or the like. Any of the conditions conventional in such demethylation reactions can be utilized to carry out the reaction.

The compound of formula CXIV is the compound of formula CXVII where R$^1$ is an alkyl group having 1 to 3 carbon atoms. The compound of formula CXIV can be converted to the free acid i.e. the compound of formula CXVII where R$^1$ is H by ester hydrolysis. Any conventional method of ester hydrolysis will produce the compound of formula CXVII where R$^1$ is H.

Compounds of general formula CXI can be prepared by etherification of compound of formula CI by using alkyl halide followed by an ester hydrolysis.

CI

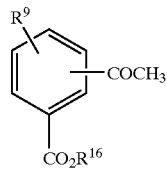

wherein R$^{16}$ is a lower alkyl group having 1 to 3 carbon atoms. R$^9$ is a hydroxyl group.

The reaction between compound of formula CI and alkyl halide can be carried like in an organic solvent, for example N,N-dimethylformamide or the like, using base, for example potassium carbonate, cesium carbonate or the like. Any of the conditions conventional in such alkylation reactions can be utilized to carry out this reaction. Ester hydrolysis can be conducted under acidic conditions for example, hydrochloric acid or hydrochloric acid mixed with organic solvent for example, ethanol or using acetic acid or the like. The reaction can be carried out at room temperature to solvent refluxing temperature. Any conventional conditions for acidic ester hydrolysis can be utilized to carry out this reaction. Further, if needed, ester hydrolysis can be carried out using basic conditions, for example, in an aqueous solution of sodium hydroxide or a mixed solution of sodium hydroxide in an organic solvent for example, ethanol or the like. Any conditions conventional for basic hydrolysis can be utilized to carry out this reaction Compounds of general formula CXII can be prepared by reacting compound of formula VII with chlorinating agent for example, trimethylsilyl chloride, thionyl chloride or the like in an organic solvent for example, dimethyl sulfoxide, N,N-dimethylformamide or the like. The reaction temperature can be room temperature to organic refluxing temperature. Any conditions conventional for chlorination reactions can be utilized to carry out the reaction.

The chloromethyl intermediate was converted to compound of formula CXII via Gabriel synthesis by treating chloromethyl intermediate with potassium phthalimide in an organic solvent for example, N,N-dimethylformamide, dioxane or the like. The phthalimide is then reacted with hydrazine by an exchange reaction in an organic solvent for example, ethanol, dioxane or the like to produce the compound of formula CXII. Any of the conditions conventionally used in the Gabriel synthesis can be utilized to carry out the reaction.

Scheme 28

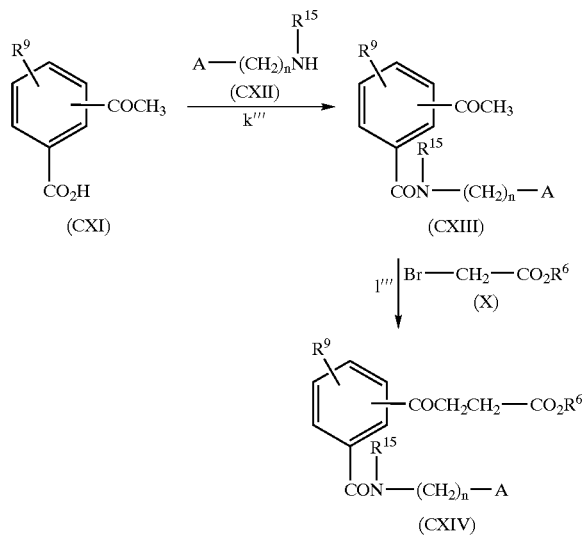

The invention will be better understood by reference to the following examples which illustrate but do not limit the invention described herein.

CHEMICAL SYNTHESIS EXAMPLES

Example 1

Synthesis of 4-(4-(2-Fluorobenzyloxy)phenyl)-4-oxobutyric acid

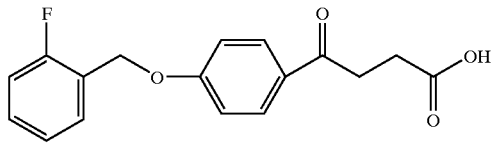

Step A: Preparation of 4-(2-Fluorobenzyloxy)acetophenone:

A solution of 4-Hydroxyacetophenone (2.80 g, 20.6 mmol) in dry DMF (15 ml) was added at room temperature to a suspension of NaH (60% in oil, 0.794 g) in dry DMF (20 ml). When evolution of hydrogen ceased, 2-Fluorobenzyl bromide (3 g, 15.8 mmol) was added drop wise. The reaction mixture was stirred at room temperature for 6 hours, quenched with sat aq. $NH_4Cl$ and concentrated in vacuo. The crude residue was taken in EtOAc and washed with water and brine. The organic layer was dried over $Na_2SO_4$, filtered and concentrated. The residue was purified by flash chromatography on silica gel column (hex:ethyl acetate, 2:1) to provide the title compound as an off white solid.

$^1$H NMR (270 MHz, $CDCl_3$): 2.5 (s, 3H); 5.2 (s, 2H); 6.9–7.1 (m, 4H); 7.2–7.3 (m, 1H); 7.4 (t, 1H); 7.9 (d, 2H).

Step B: Preparation of tert-Butyl 4-(4-(2-fluorobenzyloxy)phenyl)-4-oxobutyrate:

To a stirred solution of 4-(2-fluorobenzyloxy)acetophenone (Step A, 1.5 g, 6.1 mmol) in dry THF (20 ml) and DMPU (5 ml) was added a solution of lithium bis(trimethylsilyl)amide (1.0M, 7 ml) at −60° C. under argon. After 10 minutes of stirring at −60° C., tert-Butyl bromoacetate (4.75 g, 24.4 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over $Na_2SO_4$, filtered, concentrated and purified by flash chromatography on a silica gel column (hex:ethyl acetate, 2:1) to provide the title compound.

$^1$H NMR (270 MHz, $CDCl_3$): 1.4 (s, 9H); 2.7 (t, 2H); 3.2 (t, 2H); 5.1 (s, 2H); 6.9–7.1 (m, 4H); 7.2–7.3 (m, 1H); 7.4 (t, 1H); 7.9 (d, 2H).

Step C: Preparation of 4-(4-(2-Fluorobenzyloxy)phenyl)-4-oxobutyric acid:

A solution of tert-Butyl 4-(4-(2-fluorobenzyloxy)phenyl)-4-oxobutyrate (Step B, 1.27 g, 4.2 mmol) in dichloromethane (25 ml) was treated with trifluoroacetic acid (5 ml). The reaction mixture was stirred at ambient temperature for 3 hours and concentrated in vacuo. The purification was done by flash chromatography on silica gel column (chloroform:methanol, 95:5 spiked with acetic acid) to afford the title compound as a white powder.

$^1$H NMR (270 MHz, $CDCl_3$:$CD_3OD$): 2.6 (t, 2H); 3.2 (t, 2H); 5.1 (s, 2H); 6.9–7.1 (m, 4H); 7.2–7.3 (m, 1H); 7.4 (t, 2H); 7.9 (d, 2H).

Example 2

Synthesis of 4-(4-(2-Methoxybenzyloxy)phenyl)-4-oxobutyric acid

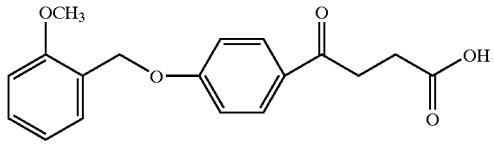

Step A: Preparation of 4-(2-Methoxybenzyloxy)acetophenone:

A solution of 2-Methoxybenzyl alcohol (2.99 g, 21.7 mmol) in dry THF (5 ml) and dry DMF (5 ml) was added to a stirred solution of 4-Hydroxyacetophenone (3.25 g, 23.8 mmol), triphenylphosphine (7.36 g, 28.0 mmol), and diethyl azodicarboxylate (4.51 g, 25.9 mmol) in dry THF (20 ml) at 5–10° C. The reaction mixture was stirred at 0° C. for 2 hours, warmed to room temperature and concentrated in vacuo. The residue was taken in EtOAc and washed twice with saturated $NaHCO_3$. The organic layer was dried over $Na_2SO_4$, filtered, concentrated and purified by flash chromatography on a silica gel column (choloroform:methanol, 99:1) to provide the title compound as a white solid.

$^1$H NMR (270 MHz, CDCl$_3$): 2.5 (s, 3H); 3.9 (s, 3H); 5.2 (s, 2H); 6.9–7.1 (m, 4H); 7.3 (m, 1H); 7.4 (d, 1H); 7.9 (d, 2H).

Step B: Preparation of Ethyl 4-(4-(2-methoxybenzyloxy)phenyl)-4-oxobutyrate:

To a stirred solution of 4-(2-Methoxybenzyloxy)acetophenone (Step A, 1.22 g, 4.7 mmol) in dry THF (20 ml) and DMPU (5 ml) was added a solution of lithium bis(trimethylsilyl)amide (1.0M, 5 ml) under argon at −60° C. After 10 minutes of stirring at −60° C., ethyl bromoacetate (2.59 g, 15.6 mmol) was added rapidly. The reaction mixture was stirred for an additional 10 minutes and then warmed to room temperature for 2 hours. The crude mixture was taken in EtOAc and washed with water. The aqueous layer was extracted one more time with EtOAc and combined organic layers were dried over Na$_2$SO$_4$, filtered and concentrated. The purification was done by flash chromatography on silica gel column (hex:ethyl acetate, 4:1) to provide the title compound as a white solid.

$^1$H NMR (270 MHz, CDCl$_3$): 1.2 (t, 3H); 2.6 (t, 2H); 3.2 (t, 2H); 3.8 (s, 3H); 4.1 (q, 2H); 5.1 (s, 2H); 6.9–7.0 (m, 4H); 7.1–7.3 (m, 2H); 7.9 (d, 2H).

Step C: Preparation of 4-(4-(2-Methoxybenzyloxy)phenyl)-4-oxobutyric acid:

A solution of Ethyl 4-(4-(2-methoxybenzyloxy)phenyl)-4-oxobutyrate (Step B, 1.49 g, 4.3 mmol) in abs ethanol (20 ml) was treated with 1N NaOH (6 ml). The reaction mixture was stirred at room temperature for 2 hours and then acidified with 1M HCl. The resulting white solid was filtered, washed with cold water and dried under vacuum to provide the title compound.

$^1$H NMR (270 MHz, CDCl$_3$: CD$_3$OD): 2.6 (t, 2H); 3.2 (t, 2H); 3.8 (s, 3H); 5.1 (s, 2H); 6.9–7.0 (m, 4H); 7.2–7.3 (m, 2H); 7.8 (d, 2H).

Example 3

Synthesis of 3-[(4-(2-Fluorobenzyloxy)phenyl)-methylthio]propionic acid

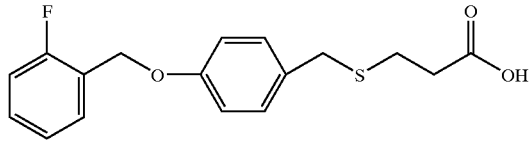

Step A: Preparation of 4-Hydroxybenzyl bromide:

To a stirred solution of PBr$_3$ (1.38 g, 5.0 mmol) in dry THF (2 ml) at −5° C. was added a solution of dry pyridine (0.201 ml) in dry THF (0.4 ml). A solution of 4-Hydroxybenzyl alcohol (1.89 g, 15.2 mmol) in dry THF (23 ml) was added drop wise to the reaction mixture. The reaction mixture was allowed to stand at room temperature for 18 hours, then diluted with THF and filtered through celite pad. The filtrate was evaporated, the resulting semisolid was redissolved in dry toluene (16 ml). The solution was maintained at −20° C. for 2 hours, and then filtered through celite pad to provide the title compound as a light yellow solution which was used without further purification.

Step B: Preparation of Ethyl 3-((4-hydroxyphenyl)-methylthio)propionate:

To a solution of NaH (60% dispersed in oil, 0.731 g, 21.7 mmol) in dry DMF (15 ml) was added Ethyl 0.3-mercaptopropionate (2.66 g, 19.8 mmol). When the evolution of hydrogen ceased, 4-Hydroxybenzyl bromide from Step A was added. The reaction mixture was stirred for 16 hours at room temperature, quenched with sat. NH$_4$Cl and concentrated in vacuo. The crude residue was taken in EtOAc and washed with water and brine. The aqueous layer was washed one more time with EtOAc. The combined organic layers were dried over Na$_2$SO$_4$, filtered and concentrated. The purification was done by flash chromatography on silica gel column (dichloromethane:ethyl acetate, 95:5) to provide the title compound.

$^1$H NMR (270 MHz, CDCl$_3$): 1.2 (t, 3H); 2.4–2.6 (m, 4H); 3.6 (s, 2H); 4.1 (q, 2H); 6.7 (d, 2H); 7.2 (d, 2H).

Step C: Preparation of Ethyl 3-((4-(2-fluorobenzyloxy)phenyl)-methylthio)propionate:

To a solution of NaH (60% dispersed in oil, 0.054 g, 1.3 mmol) in dry DMF (10 ml) was added Ethyl 3-((4-hydroxyphenyl)-methylthio)propionate (Step B, 2.5 g, 1.0 mmol). When the evolution of hydrogen ceased, 2-Fluorobenzyl bromide (0.263 g, 1.3 mmol) was added. The reaction mixture was stirred for 4 hours at room temperature, quenched with sat. NH$_4$Cl, and concentrated in vacuo. The crude residue was taken in EtOAc and washed twice with water and brine. The aqueous layer was washed one more time with EtOAc. The combined organic layers were dried over Na$_2$SO$_4$, filtered and concentrated. The purification was done by flash chromatography on silica gel column (hex:ethyl acetate, 4:1) to provide the title compound.

$^1$H NMR (270 MHz, CDCl$_3$): 1.2 (t, 3H); 2.4–2.6 (m, 4H); 3.6 (s, 2H); 4.2 (q, 2H); 5.15 (s, 2H); 6.9 (d, 2H); 7.2–7.4 (m, 5H); 7.5 (t, 1H).

Step D: Preparation of 3-((4-(2-fluorobenzyloxy)phenyl)-methylthio)propionic acid:

To a solution of Ethyl 3-((4-(2-fluorobenzyloxy)phenyl)-methylthio)propionate (Step C, 0.122 g, 0.35 mmol) in ethanol (5 ml) was added 1N NaOH (0.5 ml) at room temperature. The reaction mixture was stirred for 3 hours, acidified with 1M HCl and concentrated in vacuo to give white solid which was purified by flash chromatography on silica gel column (chloroform:methanol, 92.5:7.5 spiked with acetic acid) to provide the title compound as a white solid.

$^1$H NMR (270 MHz, CDCl$_3$): 2.4–2.6 (m, 4H); 3.7 (s, 2H); 5.1 (s, 2H); 6.9 (d, 2H); 7.2–7.4 (m, 5H); 7.5 (t, 1H).

Example 4

Synthesis of 4-(4-(3-Fluorobenzyloxy)phenyl)-4-oxobutyric acid

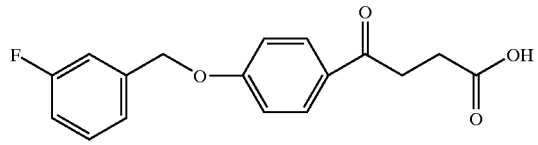

Step A: Preparation of 4-(3-Fluorobenzyloxy)acetophenone:

Using the method of Example 1, Step A, using 3-Fluorobenzyl bromide as the starting material, the title compound was obtained.

$^1$H NMR (270 MHz, CDCl$_3$): 2.5 (s, 3H); 5.1 (s, 2H); 7.0 (m, 3H); 7.2–7.3 (t, 2H); 7.4 (m, 1H); 7.9 (d, 2H).

Step B: Preparation of tert-Butyl 4-(4-(3-fluorobenzyloxy)phenyl)-4-oxobutyrate:

Using the method of Example 1, Step B, the title compound was obtained.

$^1$H NMR (270 MHz, CDCl$_3$): 1.4 (s, 9H); 2.7 (t, 2H); 3.2 (t, 2H); 5.1 (s, 2H); 7.0 (m, 3H); 7.2 (t, 2H); 7.4 (m, 1H); 8.0 (d, 2H).

Step C: Preparation of 4-(4-(3-Fluorobenzyloxy)phenyl)-4-oxobutyric acid:

Using the method of Example 1, Step C, the title compound was obtained.

$^1$H NMR (270 MHz, CDCl$_3$): 2.8 (t, 2H); 3.2 (t, 2H); 5.1 (s, 2H); 6.9–7.1 (m, 3H); 7.2–7.3 (m, 2H); 7.4 (q, 1H); 7.9 (d, 2H).

Example 5

Synthesis of 4-(4-(4-Fluorobenzyloxy)phenyl)-4-oxobutyric acid

Step A: Preparation of 4-(4-Fluorobenzyloxy)acetophenone:

Using the method of Example 1, Step A, using 4-Fluorobenzyl bromide as the starting material, the title compound was obtained.

$^1$H NMR (270 MHz, CDCl$_3$): 2.5 (s, 3H); 5.1 (s, 2H); 7.0 (d, 2H); 7.1 (t, 2H); 7.4 (m, 2H); 7.9 (d, 2H).

Step B: Preparation of tert-Butyl 4-(4-(4-fluorobenzyloxy)phenyl)-4-oxobutyrate:

Using the method of Example 1, Step B, the title compound was obtained $^1$H NMR (270 MHz, CDCl$_3$): 1.4 (s, 9H); 2.8 (t, 2H); 3.2 (t, 2H); 5.1 (s, 2H); 7.0 (m, 2H); 7.2 (t, 2H); 7.4 (m, 2H); 8.0 (d, 2H).

Step C: Preparation of 4-(4-(4-Fluorobenzyloxy)phenyl)-4-oxobutyric acid:

Using the method of Example 1, Step C, the title compound was obtained.

$^1$H NMR (270 MHz, CDCl$_3$): 2.8 (t, 2H); 3.2 (t, 2H); 5.1 (s, 2H); 6.9–7.1 (m, 2H); 7.2–7.3 (d, 2H); 7.4 (m, 2H); 7.9 (d, 2H).

Example 6

Synthesis of 4-(4-((2-Pyridinyl)-methoxy)phenyl)-4-oxobutyric acid

Step A: Preparation of 4-((2-Pyridinyl)-methoxy)acetophenone:

A solution of 4-Hydroxyacetophenone (1.99 g, 14.6 mmol) in dry DMF (5 ml) was added at room temperature to a suspension of NaH (60% in oil, 0.604 g) in dry DMF (20 ml). When evolution of hydrogen ceased, 2-Picolyl chloride hydrochloride (2 g, 12.1 mmol) was added. The reaction mixture was stirred at room temperature for 16 hours, quenched with sat aq. NH$_4$Cl and concentrated in vacuo. The crude residue was taken in EtOAc and washed with water and brine. The aqueous layer was washed twice with EtOAc. The combined organic layers were dried over Na$_2$SO$_4$, filtered and concentrated. The residue was purified by flash chromatography on silica gel column (hex:ethyl acetate, 1:1) to provide the title compound.

$^1$H NMR (270 MHz, CDCl$_3$): 2.5 (s, 3H); 5.2 (s, 2H); 7.0 (d, 2H); 7.2 (m, 1H); 7.5 (d, 1H); 7.7 (t, 1H); 7.9 (d, 2H); 8.6 (s, 1H).

Step B: Preparation of tert-Butyl 4-(4-((2-pyridinyl)-methoxy)phenyl)-4-oxobutyrate:

To a stirred solution of 4-((2-Pyridinyl)-methoxy) acetophenone (Step A, 0.968 g, 3.6 mmol) in dry THF (16 ml) and DMPU (4 ml) was added a solution of lithium bis(trimethylsilyl)amide (1.0M, 5 ml) at −60° C. under argon. After stirring for 10 minutes at −60° C., tert-Butyl bromoacetate (2.64 g, 13.5 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over Na$_2$SO$_4$, filtered, concentrated and purified by flash chromatography on silica gel column (hex:ethyl acetate, 2:1) to provide the title compound.

$^1$H NMR (270 MHz, CDCl$_3$): 1.4 (s, 9H); 2.7 (t, 2H); 3.2 (t, 2H); 5.3 (s, 2H); 7.0 (d, 2H); 7.2 (m, 1H); 7.5 (d, 1H); 7.7 (t, 1H); 7.9 (d, 2H); 8.6 (s, 1H).

Step C: Preparation of 4-(4-((2-Pyridinyl)-methoxy) phenyl)-4-oxobutyric acid:

A solution of tert-Butyl 4-(4-((2-pyridinyl)-methoxy) phenyl)-4-oxobutyrate (Step C, 1.27 g, 4.2 mmol) in dichloromethane (25 ml) was treated with trifluoroacetic acid (5 ml). The mixture was stirred at ambient temperature for 3 hours and concentrated in vacuo. The purification was done by flash chromatography on silica gel column (chloroform:methanol, 95:5 spiked with acetic acid) to provide the title compound as a white solid.

$^1$H NMR (270 MHz, CDCl$_3$:CD$_3$OD): 2.7 (t, 2H); 3.2 (t, 2H); 5.3 (s, 2H); 7.0 (d, 2H); 7.3 (m, 1H); 7.5 (d, 1H); 7.9 (m, 3H); 8.6 (s, 1H).

Example 7

Synthesis of 4-(4-(Benzyloxy)phenyl)-4-oxobutyric acid

Step A: Preparation of 4-(Benzyloxy)acetophenone:

Using the method of Example 1, Step A, using Benzyl bromide as the starting material, the title compound was obtained.

$^1$H NMR (270 MHz, CDCl$_3$): 2.5 (s, 3H); 5.1 (s, 2H); 7.0 (d, 2H); 7.3–7.5 (m, 5H); 7.9 (d, 2H).

Step B: Preparation of tert-Butyl 4-(4-(benzyloxy)phenyl)-4-oxobutyrate:

Using the method of Example 1, Step B, the title compound was obtained.

$^1$H NMR (270 MHz, CDCl$_3$): 1.4 (s, 9H); 2.6 (t, 2H); 3.2 (t, 2H); 5.2 (s, 2H); 7.0 (d, 2H); 7.3–7.5 (m, 5H); 7.9 (d, 2H).

Step C: Preparation of 4-(4-(Benzyloxy)phenyl)-4-oxobutyric acid:

Using the method of Example 1, Step C, the title compound was obtained.

$^1$H NMR (270 MHz, CDCl$_3$): 2.8 (t, 2H); 3.2 (t, 2H); 5.1 (s, 2H); 7.0 (d, 2H); 7.3–7.5 (m, 5H); 7.9 (d, 2H).

Example 8

Synthesis of 4-(4-(2,6-Difluorobenzyloxy)phenyl)-4-oxobutyric acid

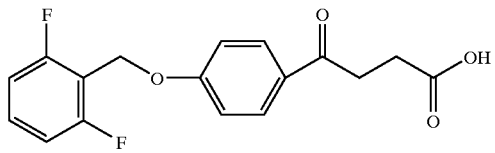

Step A: Preparation of 4-(2,6-Difluorobenzyloxy) acetophenone:

A solution of 4-Hydroxyacetophenone (3.61 g, 26.5 mmol) in dry DMF (5 ml) was added at room temperature to a suspension of NaH (60% in oil, 1.21 g) in dry DMF (40 ml). When evolution of hydrogen ceased, 2,6-Difluorobenzyl bromide (5 g, 24.1 mmol) was added dropwise. The reaction mixture was stirred at room temperature for 6 hours, quenched with sat aq. NH$_4$Cl and concentrated in vacuo. The crude residue was taken in EtOAc and washed with water and brine. The aqueous layer was extracted one more time with EtOAc. The combined organic layers were dried over Na$_2$SO$_4$, filtered and concentrated. The residue was purified by flash chromatography on silica gel column (hex:ethyl acetate, 2:1) to provide the title compound.

$^1$H NMR (270 MHz, CDCl$_3$): 2.5 (s, 3H); 5.2 (s, 2H); 6.9–7.0 (m, 4H); 7.3–7.4 (m, 1H); 7.9 (d, 2H).

Step B: Preparation of tert-Butyl 4-(4-(2,6-difluorobenzyloxy)phenyl)-4-oxobutyrate:

To a stirred solution of 4-(2,6-Difluorobenzyloxy) acetophenone (Step A, 0.6 g, 22.8 mmol) in dry THF (60 ml) and DMPU (12 ml) was added a solution of lithium bis(trimethylsilyl)amide (1.0M, 30 ml) at −60° C. under argon. After stirring for 10 minutes at −60° C., tert-Butyl bromoacetate (8.97 g, 46 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over Na$_2$SO$_4$, filtered, concentrated and purified by flash chromatography on a silica gel column (hex:ethyl acetate, 2:1) to provide the title compound as a white solid.

$^1$H NMR (270 MHz, CDCl$_3$): 1.4 (s, 9H); 2.6 (t, 2H); 3.2 (t, 2H); 5.2 (s, 2H); 6.9–7.0 (m, 4H); 7.3–7.4 (m, 1H); 7.9 (d, 2H).

Step C: Preparation of 4-(4-(2,6-Difluorobenzyloxy) phenyl)-4-oxobutyric acid:

A solution of tert-Butyl 4-(4-(2,6-difluorobenzyloxy) phenyl)-4-oxobutyrate (Step B, 4.76 g, 12.6 mmol) in dichloromethane (40 ml) was treated with trifluoroacetic acid (20 ml). The mixture was stirred at ambient temperature for 3 hours and concentrated in vacuo. The purification was done by flash chromatography on silica gel column (chloroform:methanol, 95:5 spiked with acetic acid) to provide the title compound as a white powder.

$^1$H NMR (270 MHz, CDCl$_3$): 2.8 (t, 2H); 3.2 (t, 2H); 5.2 (s, 2H); 6.9–7.0 (m, 4H); 7.4 (m, 1H); 7.9 (d, 2H).

Example 9

Synthesis of 4-(4-(2-Chlorobenzyloxy)phenyl)-4-oxobutyric acid

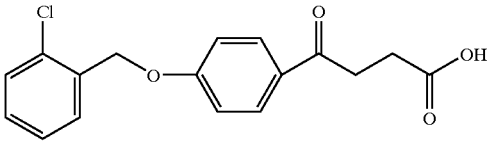

Step A: Preparation of 4-(2-Chlorobenzyloxy) acetophenone:

Using the method of Example 1, Step A, using 2-Chlorobenzyl bromide as the starting material, the title compound was obtained.

$^1$H NMR (270 MHz, CDCl$_3$): 2.5 (s, 3H); 5.2 (s, 2H); 7.0 (d, 2H); 7.2–7.5 (m, 4H); 7.9 (d, 2H).

Step B: Preparation of tert-Butyl 4-(4-(2-chlorobenzyloxy) phenyl)-4-oxobutyrate:

Using the method of Example 1, Step B, the title compound was obtained.

$^1$H NMR (270 MHz, CDCl$_3$): 1.4 (s, 9H); 2.6 (t, 2H); 3.2 (t, 2H); 5.2 (s, 2H); 7.0 (d, 2H); 7.2–7.5 (m, 4H); 7.9 (d, 2H).

Step C: Preparation of 4-(4-(2-Chlorobenzyloxy)phenyl)-4-oxobutyric acid:

Using the method of Example 1, Step C, the title compound was obtained.

$^1$H NMR (270 MHz, CDCl$_3$:CD$_3$OD): 2.6 (t, 2H); 3.2 (t, 2H); 5.2 (s, 2H); 7.0 (d, 2H); 7.2 (m, 2H); 7.3 (m, 1H); 7.4 (m, 1H); 7.9 (d, 2H).

Example 10

Synthesis of 4-(4-(2-(2-Fluorophenyl)ethoxy) phenyl)-4-oxobutyric acid

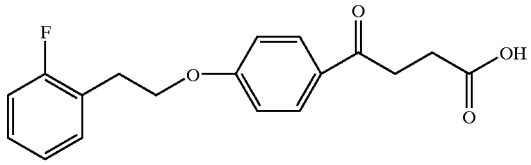

Step A: Preparation of 4-(2-(2-fluorophenyl)ethoxy) acetophenone:

Using the method of Example 2, Step A, using 2-Fluorophenethyl alcohol as the starting material, the title compound was obtained.

$^1$H NMR (270 MHz, CDCl$_3$): 2.3 (s, 3H); 2.9 (t, 2H); 4.2 (t, 2H); 6.9 (d, 2H); 7.1 (m, 2H); 7.3 (m, 2H); 7.9 (d, 2H).

Step B: Preparation of tert-Butyl 4-(4-(2-(2-fluorophenyl) ethoxy)phenyl)-4-oxobutyrate:

Using the method of Example 2, Step B, using tert-Butyl bromoacetate as the starting material, the title compound was obtained.

$^1$H NMR (270 MHz, CDCl$_3$): 1.4 (s, 9H); 2.6 (t, 2H); 3.2 (m, 4H); 4.2 (t, 2H); 6.9 (d, 2H); 7.1 (m, 2H); 7.3 (t, 2H); 7.9 (d, 2H).

Step C: Preparation of 4-(4-(2-(2-Fluorophenyl)ethoxy) phenyl)-4-oxobutyric acid:

A solution of tert-Butyl 4-(4-(2-(2-Fluorophenyl)ethoxy) phenyl)-4-oxobutyrate (Step 2, 1.2 g, 3.2 mmol) in dichloromethane (25 ml) was treated with trifluoroacetic acid (10 ml). The reaction mixture was stirred at ambient temperature for 4 hours and concentrated in vacuo. The purification was done by flash chromatography on silica gel column (chloroform:methanol, 95:5 spiked with acetic acid) to provide the title compound as a white solid.

¹H NMR (270 MHz, CDCl₃): 2.8 (t, 2H); 3.3 (t, 2H); 4.2 (t, 2H); 6.9 (d, 2H); 7.1 (m, 2H); 7.3 (t, 2H); 7.9 (d, 2H).

Example 11

Synthesis of Ethyl 4-(4-(2-Fluorobenzyloxyl)phenyl)-4-oxobutyrate

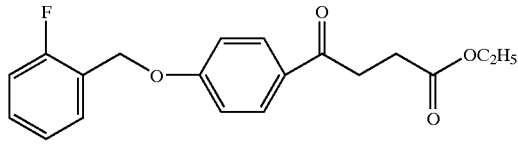

Step A: Preparation of 4-(4-(2-Fluorobenzyloxy)acetophenone:

Using the method of Example 1, Step A, the title compound was obtained.

¹H NMR (270 MHz, CDCl₃): 2.5 (s, 3H); 5.2 (s, 2H); 6.9–7.1 (m, 4H); 7.2–7.3 (m, 1H); 7.4 (t, 1H); 7.9 (d, 2H).

Step B: Preparation of Ethyl 4-(4-(2-fluorobenzyloxy)phenyl)-4-oxobutyrate:

To a stirred solution of 4-(2-Fluorobenzyloxy)acetophenone (7.26 g, 29.7 mmol) in dry THF (80 ml) and DMPU (16 ml) was added a solution of lithium bis(trimethylsilyl)amide (1.0M, 35 ml) at −60° C. under argon. After stirring for 10 minutes at −6⁰° C., Ethyl bromoacetate (10.12 g, 60.5 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over Na₂SO₄, filtered, concentrated and purified by flash chromatography on a silica gel column (hex:ethyl acetate, 4:1) to provide the title compound as a white powder.

¹H NMR (270 MHz, CDCl₃): 1.2 (t, 3H); 2.7 (t, 2H); 3.2 (t, 2H); 4.2 (q, 2H); 5.1 (s, 2H); 6.9 (d, 2H); 7.2 (m, 2H); 7.4 (m, 1H); 7.5 (m, 1H); 7.9 (d, 2H).

Example 12

Synthesis of 4-(4-(2-Methylbenzyloxy)phenyl)-4-oxobutyric acid

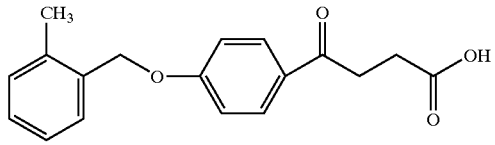

Step A: Preparation of 4-(2-Methylbenzyloxy)acetophenone:

Using the method of Example 1, Step A, using 2-Methylbenzyl bromide as the starting material, the title compound was obtained.

¹H NMR (270 MHz, CDCl₃): 2.4 (s, 3H); 2.5 (s, 3H); 5.2 (s, 2H); 6.9 (d, 2H); 7.2–7.3 (m, 3H); 7.4 (m, 1H); 7.9 (d, 2H).

Step B: Preparation of tert-Butyl 4-(4-(2-methylbenzyloxy)phenyl)-4-oxobutyrate:

Using the method of Example 1, Step B, the title compound was obtained.

¹H NMR (270 MHz, CDCl₃): 1.5 (s, 9H); 2.4 (s, 3H); 2.6 (t, 2H); 3.2 (t, 2H); 5.2 (s, 2H); 6.9 (d, 2H); 7.2–7.3 (m, 3H); 7.4 (m, 1H); 7.9 (d, 2H).

Step C: Preparation of 4-(4-(2-Methylbenzyloxy)phenyl)-4-oxobutyric acid:

Using the method of Example 1, Step C, the title compound was obtained.

¹H NMR (270 MHz, CDCl₃): 2.4 (s, 3H); 2.8 (t, 2H); 3.2 (t, 2H); 5.1 (s, 2H); 6.9 (d, 2H); 7.2–7.3 (m, 3H); 7.4 (m, 1H); 7.9 (d, 2H).

Example 13

Synthesis of 4-[4-(2-(N-(2-fluorobenzyl)-N-methylamino)ethoxy)phenyl]-4-oxobutyric acid

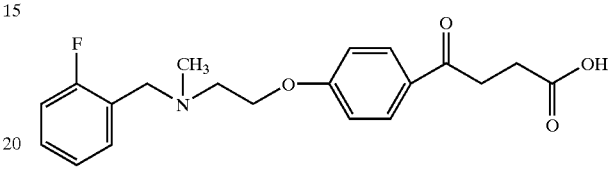

Step A: Preparation of 2-Fluorobenzyl methanesulfonate:

To a solution of 2-Fluorobenzyl alcohol (10 g, 79.28 mmol) in dry dichloromethane (200 ml) was added triethylamine (12.03 g, 118.9 mmol) under argon at room temperature. Methanesulfonyl chloride (10.71 g, 93.5 mmol) was added to the above reaction mixture at 0° C., and stirring was continued for another 3 hours. Water (100 ml) was added to the reaction mixture and the mixture was extracted twice with dichloromethane. The combined organic layers were washed with water and brine. The reaction mixture was dried over Na₂SO₄, filtered and concentrated to give the title compound as an yellow oil which was used without further purification.

¹H NMR (270 MHz, CDCl₃): 1.3 (t, 3H); 2.4–2.6 (m, 4H); 5.25 (s, 2H); 6.9–7.5 (m, 4H).

Step B: Preparation of 2-(N-(2-fluorobenzyl)-N-methylamino)-ethanol:

A mix of 2-Fluorobenzyl methanesulfonate (Step A, 5 g, 24.5 mmol) and 2-(Methylamino)-ethanol (18.4 g, 244.9 mmol) was heated under argon at 120° C. with stirring for 7 hours. The mixture was cooled to room temperature and concentrated. The crude residue was purified by flash chromatography on silica gel column (chloroform:methanol, 90:10 spiked with triethylamine) to provide the title compound.

¹H NMR (270 MHz, CDCl₃): 2.3 (s, 3H); 2.6 (m, 2H); 3.6 (m, 4H); 6.9–7.5 (m, 4H).

Step C: Preparation of 2-(N-(2-fluorobenzyl)-N-methylamino)-ethyl chloride:

To a solution of 2-(N-(2-fluorobenzyl)-N-methylamino)-ethanol (Step. B, 7.51 g, 41 mmol) in dry toluene (50 ml) was added thionyl chloride (16 ml). The reaction mixture was stirred at room temperature for 16 hours and concentrated. The crude mixture was diluted with chloroform and washed with aq NaHCO₃, water and brine. The organic layer was dried over Na₂SO₄, filtered and concentrated to provide the title compound which was used without further purification.

¹H NMR (270 MHz, CDCl₃): 2.3 (s, 3H); 2.8 (t, 2H); 3.6 (t, 2H); 3.7 (s, 2H); 7.0–7.15 (m, 2H); 7.25 (m, 1H), 7.4 (t, 1H).

Step D: Preparation of 4-(2-(N-(2-fluorobenzyl)-N-methylamino)ethoxy)acetophenone:

To a solution of 2-(N-(2-fluorobenzyl)-N-methylamino)-ethyl chloride (Step C, 7.48 g, 37 mmol) and 4-Hydroxyacetophenone (10.07 g, 74 mmol) in dry DMF (10 ml) was added K$_2$CO$_3$ (7.77 g, 56.2 mmol). The mixture was heated at 80° C. for 6 hours, cooled, quenched with water and extracted twice with EtOAc. The combined organic layers were dried over Na$_2$SO$_4$, filtered and concentrated. The crude residue was purified by flash chromatography on silica gel column (hex:ethyl acetate, 2:1) to provide the title compound as a light yellow oil.

$^1$H NMR (270 MHz, CDCl$_3$): 2.35 (s, 3H); 2.4 (s, 3H); 2.8 (t, 2H); 3.7 (s, 2H); 4.2 (t, 2H); 6.9 (d, 2H); 7.0–7.15 (m, 2H); 7.25 (m, 1H), 7.4 (t, 1H); 7.9 (d, 2H).

Step E: Preparation of tert-Butyl 4-[4-(2-(N-(2-fluorobenzyl)-N-methylamino)ethoxy)phenyl]-4-oxobutyrate:

Lithium bis(trimethylsilyl)amide (1.0M, 20 ml) was added slowly over 10 minutes to a stirred solution of 4-(2-(N-(2-fluorobenzyl)-N-methylamino)ethoxy)acetophenone (Step D, 4.91 g, 16.3 mmol) in dry THF (60 ml) and DMPU (15 ml) at −65° C. under argon. After 15 minutes of stirring, tert-Butyl bromoacetate (6.35 g, 32.6 mmol) was added rapidly. The stirring continued for an additional 10 minutes at −65° C. and then reaction was warmed to room temperature for 2 hours, quenched with water and extracted twice with EtOAc. The combined organic layers were purified by flash chromatography on silica gel column (hex:ethyl acetate, 1:1) to provide the title compound.

$^1$H NMR (270 MHz, CDCl$_3$): 1.5 (s, 9H); 2.4 (s, 3H); 2.6 (t, 2H); 2.8 (t, 2H); 3.2 (t, 2H); 3.7 (br, 2H); 4.2 (br, 2H); 6.9 (d, 2H); 7.0–7.15 (m, 2H); 7.25 (m, 1H), 7.4 (t, 1H); 7.9 (d, 2H).

Step F: Preparation of 4-[4-(2-(N-(2-fluorobenzyl)-N-methylamino)ethoxy)phenyl]-4-oxobutyric acid:

A solution of tert-Butyl 4-[4-(2-(N-(2-fluorobenzyl)-N-methylamine)ethoxy)phenyl]-4-oxobutyrate (Step E, 2.23 g, 5.3 mol) in dichloromethane (20 ml) was treated with trifluoroacetic acid (10 ml). The reaction mixture was stirred at ambient temperature for 2 hours, and concentrated in vacuo. The purification was done by flash chromatography on silica gel column (chloroform:methanol, 92.5:7.5–90:10 spiked with acetic acid) to provide the title compound.

$^1$H NMR (270 MHz, CDCl$_3$:CD$_3$OD): 2.5 (t, 2H); 2.6 (s, 3H); 3.0 (t, 2H); 3.4 (t, 2H); 4.2–4.5 (m, 4H); 6.9 (d, 2H); 7.0–7.15 (m, 2H); 7.3 (m, 1H), 7.5 (t, 1H); 7.9 (d, 2H).

Example 14

Synthesis of 4-(3-(2-Methylbenzyloxy)phenyl)-4-oxobutyric acid

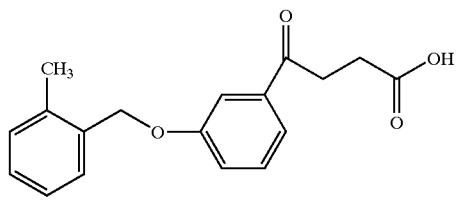

Step A: Preparation of 3-(2-Methylbenzyloxy) acetophenone:

Using the method of Example 12, Step A, using 3-Hydroxyacetophenone as the starting material, the title compound was obtained.

$^1$H NMR (270 MHz, CDCl$_3$): 2.3 (s, 3H); 2.5 (s, 3H); 5.1 (s, 2H); 7.2–7.3 (m, 4H); 7.4 (m, 2H); 7.6 (m, 2H).

Step B: Preparation of tert-Butyl 4-(3-(2-methylbenzyloxy)phenyl)-4-oxobutyrate:

Using the method of Example 1, Step B, the title compound was obtained.

$^1$H NMR (270 MHz, CDCl$_3$): 1.5 (s, 9H); 2.4 (s, 3H); 2.6 (t, 2H); 3.2 (t, 2H); 5.2 (s, 2H); 7.2–7.3 (m, 4H); 7.4 (m, 2H); 7.6 (m, 2H).

Step C: Preparation of 4-(3-(2-Methylbenzyloxy)phenyl)-4-oxobutyric acid:

Using the method of Example 1, Step C, the title compound was obtained $^1$H NMR (270 MHz, CDCl$_3$): 2.4 (s, 3H); 2.8 (t, 2H); 3.3 (t, 2H); 5.1 (s, 2H); 7.2–7.3 (m, 4H); 7.4 (m, 2H); 7.6 (m, 2H).

Example 15

Synthesis of Ethyl 4-(3-(2-fluorobenzyloxyl)phenyl)-4-oxobutyrate

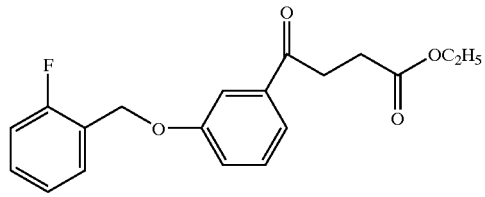

Step A: Preparation of 3-(2-Fluorobenzyloxy)acetophenone:

Using the method of Example 1, Step A, using 3-Hydroxyacetophenone as the starting material, the title compound was obtained.

$^1$H NMR (270 MHz, CDCl$_3$): 2.5 (s, 3H); 5.2 (s, 2H); 7.1 (m, 4H); 7.3 (m, 2H); 7.6 (m, 2H).

Step B: Preparation of Ethyl 4-(3-(2-fluorobenzyloxy)phenyl)-4-oxobutyrate:

Using the method of Example 11, Step B, the title compound was obtained.

$^1$H NMR (270 MHz, CDCl$_3$): 1.3 (s, 9H); 2.8 (t, 2H); 3.3 (t, 2H); 5.1 (s, 2H); 7.1 (t, 2H); 7.2 (d, 2H); 7.4 (m, 1H); 7.5 (t, 1H); 7.6 (d, 2H).

Example 16

Synthesis of Ethyl 4-(4-(2-methylbenzyloxyl)phenyl)-4-oxobutyrate

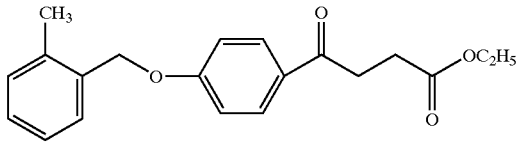

Step A: Preparation of 4-(2-Methylbenzyloxy) acetophenone:

Using the method of Example 12, Step A, the title compound was obtained.

$^1$H NMR (270 MHz, CDCl$_3$): 2.4 (s, 3H); 2.5 (s, 3H); 5.2 (s, 2H); 6.9 (d, 2H); 7.2–7.3 (m, 3H); 7.4 (m, 1H); 8.0 (d, 2H).

Step B: Preparation of Ethyl 4-(4-(2-methylbenzyloxy)phenyl)-4-oxobutyrate:

Using the method of Example 11, Step B, the title compound was obtained.

$^1$H NMR (270 MHz, CDCl$_3$): 1.2 (t, 3H); 2.4 (s, 3H); 2.7 (t, 2H); 3.2 (t, 2H); 4.2 (q, 2H); 5.1 (s, 2H); 7.0 (d, 2H); 7.2–7.3 (m, 3H); 7.4 (m, 1H); 8.0 (d, 2H).

Example 17

Synthesis of Ethyl 4-(4-(2,6-difluorobenzyloxyl)phenyl)-4-oxobutyrate

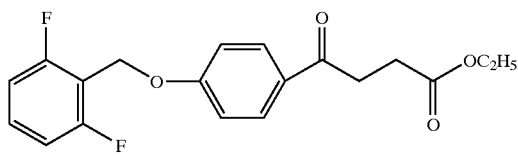

Step A: Preparation of 4-(2,6-Difluorobenzyloxy)acetophenone:

Using the method of Example 8, Step A, the title compound was obtained $^1$H NMR (270 MHz, CDCl$_3$): 2.5 (s, 3H); 5.2 (s, 2H); 6.9–7.0 (m, 4H); 7.3–7.4 (m, 1H); 7.9 (d, 2H).

Step B: Preparation of Ethyl 4-(4-(2,6-Difluorobenzyloxy)phenyl)-4-oxobutyrate:

To a stirred solution of 4-(2,6-Difluorobenzyloxy)acetophenone (Step A, 0.6 g, 22.8 mmol) in dry THF (60 ml) and DMPU (12 ml) was added a solution of lithium bis(trimethylsilyl)amide (1.0M, 30 ml) at −60° C. under argon. After stirring for 10 minutes at −60° C., Ethyl bromoacetate (7.61 g, 45.6 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over Na$_2$SO$_4$, filtered, concentrated and purified by flash chromatography on silica gel column (hex:ethyl acetate, 4:1) to provide the title compound as a white solid.

$^1$H NMR (270 MHz, CDCl$_3$): 1.3 (t, 3H); 2.8 (t, 3H); 3.2 (t, 2H); 4.1 (q, 2H); 5.2 (s, 2H); 6.9–7.0 (m, 4H); 7.3–7.4 (m, 1H); 7.9 (d, 2H).

Example 18

Synthesis of 4-(4-(2-(2-Thienyl)ethoxy)phenyl)-4-oxobutyric acid

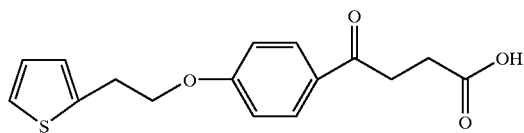

Step A: Preparation of 4-(2-(2-Thienyl)ethoxy)acetophenone:

Using the method of Example 2, Step A, using 2-(2-Thienyl)ethanol as the starting material and purification by flash chromatography on silica gel column (hex:ethylacetate, 3:1), the title compound was obtained.

$^1$H NMR (270 MHz, CDCl$_3$): 2.5 (s, 3H); 3.3 (t, 2H); 4.2 (t, 2H); 6.9–7.1 (m, 4H); 7.2 (d, 1H); 7.9 (d, 2H).

Step B: Preparation of Ethyl 4-(4-(2-(2-thienyl)ethoxy)phenyl)-4-oxobutyrate:

Using the method of Example 2, Step B, the title compound was obtained.

$^1$H NMR (270 MHz, CDCl$_3$): 1.3 (t, 3H); 2.8 (t, 2H); 3.3 (m, 4H); 4.1 (q, 2H); 4.2 (t, 2H); 6.9–7.1 (m, 4H); 7.2 (d, 1H); 7.9 (d, 2H).

Step C: Preparation of 4-(4-(2-(2-Thienyl)ethoxy)phenyl)-4-oxobutyric acid:

Using the method of Example 2, Step C, the title compound was obtained $^1$H NMR (270 MHz, CDCl$_3$): 2.8 (t, 2H); 3.3 (m, 4H); 4.2 (t, 2H); 6.9–7.1 (m, 4H); 7.2 (d, 1H); 7.9 (d, 2H).

Example 19

Synthesis of 4-(2,6-Difluorophenyl)-4-oxobutyric acid

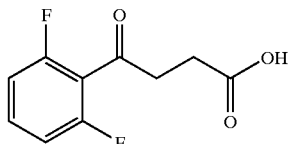

Step A: Preparation of tert-Butyl 4-(2,6-difluorophenyl)-4-oxobutyrate:

To a stirred solution of 2,6-Difluoroacetophenone (5 g, 32 mmol) in dry THF (40 ml) and DMPU (8 ml) was added a solution of lithium bis(trimethylsilyl)amide (1.0M, 45 ml) at 60° C. under argon. After stirring for 10 minutes at −60° C., tert-Butyl bromoacetate (6.99 g, 35.8 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over Na$_2$SO$_4$, filtered, concentrated and purified by flash chromatography on a silica gel column (hex:ethyl acetate, 2:1) to provide the title compound.

$^1$H NMR (270 MHz, CDCl$_3$): 1.4 (s, 9H); 2.8 (t, 2H); 3.2 (t, 2H); 6.9–7.0 (m, 2H); 7.4 (m, 1H).

Step B: Preparation of Compound AS:

A solution of tert-Butyl 4-(2,6-difluorophenyl)-4-oxobutyrate (Step A, 9.52 g, 35.2 mmol) in dichloromethane (30 ml) was treated with trifluoroacetic acid (20 ml). The mixture was stirred at ambient temperature for 3 hours and concentrated. The purification was done by flash chromatography on silica gel column (chloroform:methanol, 95:5 spiked with acetic acid) to provide the title compound as a white solid.

$^1$H NMR (270 MHz, CDCl$_3$): 2.8 (t, 2H); 3.2 (t, 2H); 6.9–7.0 (m, 2H); 7.4 (m, 1H).

Example 20

Synthesis of 4-(4-(2,5-Dimethylbenzyloxy)phenyl)-4-oxobutyric acid

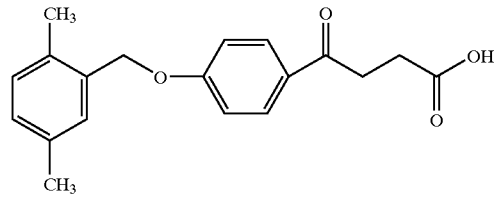

Step A: Preparation of 4-(2,5-Dimethylbenzyloxy)acetophenone:

Using the method of Example 8, Step A, using 2,5-Dimethylbenzyl chloride as the starting material, the title compound was obtained.

$^1$H NMR (270 MHz, CDCl$_3$): 2.3 (s, 3H); 2.5 (s, 3H); 5.1 (s, 2H); 6.9–7.2 (m, 5H); 7.9 (d, 2H).

Step B: Preparation of Ethyl 4-(4-(2,5-dimethylbenzyloxy)phenyl)-4-oxobutyrate:

Using the method of Example 17, Step B, the title compound was obtained.

¹H NMR (270 MHz, CDCl₃): 1.2 (s, 3H); 2.3 (s, 6H); 2.8 (t, 2H); 3.2 (t, 2H); 4.4 (q, 2H); 5.1 (s, 2H); 7.0 (d, 2H); 7.2–7.3 (m, 3H); 7.9 (d, 2H).

Step C: Preparation of 4-(4-(2,5-Dimethylbenzyloxy)phenyl)-4-oxobutyric acid:

To a solution of Ethyl 4-(4-(2,5-dimethylbenzyloxy)phenyl)-4-oxobutyrate (Step B, 2.62 g, 7.7 mmol) in abs ethanol (30 ml) was added 1N NaOH (10 ml) at room temperature. The reaction mixture was stirred for 3 hours and then acidified with 1M HCl. The occuring white precipitate was filtered, washed with water and dried under vacuum to provide the title compound as a white solid.

¹H NMR (270 MHz, CDCl₃): 2.3 (s, 6H); 2.8 (t, 2H); 3.2 (t, 2H); 5.1 (s, 2H); 7.0 (d, 2H); 7.2–7.3 (m, 3H); 8.0 (d, 2H).

Example 21

Synthesis of 4-(4-(2,5-Difluorobenzyloxy)phenyl)-4-oxobutyric acid

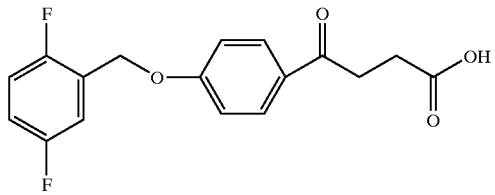

Step A: Preparation of 4-(2,5-Difluorobenzyloxy)acetophenone:

Using the method of Example 8, Step A, using 2,5-Difluorolbenzyl bromide as the starting material, the title compound was obtained.

¹H NMR (270 MHz, CDCl₃): 2.5 (s, 3H); 5.1 (s, 2H); 6.9–7.0 (m, 3H); 7.2 (m, 2H); 8.0 (d, 2H).

Step B: Preparation of Ethyl 4-(4-(2,5-difluorobenzyloxy)phenyl)-4-oxobutyrate:

Using the method of Example 17, Step B, the title compound was obtained.

¹H NMR (270 MHz, CDCl₃): 1.2 (s, 3H); 2.8 (t, 2H); 3.2 (t, 2H); 4.4 (q, 2H); 5.1 (s, 2H); 6.9–7.0 (m, 3H); 7.2 (m, 2H); 8.0 (d, 2H).

Step C: Preparation of 4-(4-(2,5-Difluorobenzyloxy)phenyl)-4-oxobutyric acid:

To a solution of Ethyl 4-(4-(2,5-Difluorobenzyloxy)phenyl)-4-oxobutyrate (Step B, 16.51 g, 47.4 mmol) in abs ethanol (100 ml) was added 1N NaOH (40 ml) at room temperature. The reaction mixture was stirred for 3 hours, acidified with 1M HCl and concentrated in vacuo. The crude mixture was taken in chloroform and washed with water. The aqueous layer was washed one more time with chloroform. The combined organic layers were dried over Na₂SO₄, filtered and concentrated. The purification was done by flash chromatography on silica gel column (chloroform:methanol, 95:5 spiked with acetic acid) to provide the title compound as a white solid.

¹H NMR (270 MHz, CDCl₃): 2.8 (t, 2H); 3.3 (t, 2H); 5.1 (s, 2H); 6.9–7.0 (m, 3H); 7.2 (m, 2H); 8.0 (d, 2H).

Example 22

Synthesis of 4-(4-(2,4-Difluorobenzyloxy)phenyl)-4-oxobutyric acid

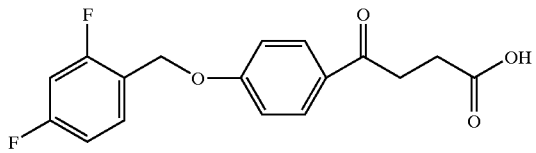

Step A: Preparation of 4-(2,4-Difluorobenzyloxy)acetophenone:

Using the method of Example 8, Step A, using 2,4-Difluorolbenzyl bromide as the starting material, the title compound was obtained.

¹H NMR (270 MHz, CDCl₃): 2.5 (s, 3H); 5.1 (s, 2H); 6.9–7.0 (m, 2H); 7.1 (d, 2H); 7.4 (m, 1H); 8.0 (d, 2H).

Step B: Preparation of Ethyl 4-(4-(2,4-difluorobenzyloxy)phenyl)-4-oxobutyrate:

Using the method of Example 17, Step B, the title compound was obtained.

¹H NMR (270 MHz, CDCl₃): 1.2 (s, 3H); 2.8 (t, 2H); 3.2 (t, 2H); 4.4 (q, 2H); 5.1 (s, 2H); 6.9–7.0 (m, 2H); 7.1 (d, 2H); 7.4 (m, 1H); 8.0 (d, 2H).

Step C: Preparation of 4-(4-(2,4-Difluorobenzyloxy)phenyl)-4-oxobutyric acid:

Using the method of Example 21, Step C, the title compound was obtained.

¹H NMR (270 MHz, CDCl₃): 2.8 (t, 2H); 3.2 (t, 2H); 5.1 (s, 2H); 6.9–7.0 (m, 2H); 7.1 (d, 2H); 7.4 (m, 1H); 8.0 (d, 2H).

Example 23

Synthesis of 4-(3-(2,6-Difluorobenzyloxy)phenyl)-4-oxobutyric acid

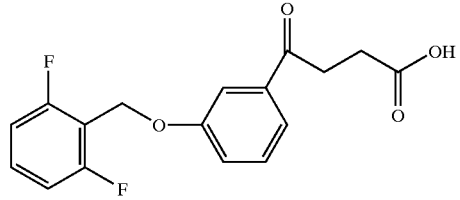

Step A: Preparation of 3-(2,6-Difluorobenzyloxy)acetophenone:

Using the method of Example 8, Step A, using 3-Hydroxyacetophenone as the starting material, the title compound was obtained.

¹H NMR (270 MHz, CDCl₃): 2.5 (s, 3H); 5.2 (s, 2H); 6.9–7.0 (m, 2H); 7.2 (m, 1H); 7.4 (m, 2H); 7.9 (d, 2H).

Step B: Preparation of Ethyl 4-(3-(2,6-difluorobenzyloxy)phenyl)-4-oxobutyrate:

Using the method of Example 17, Step B, the title compound was obtained.

¹H NMR (270 MHz, CDCl₃): 1.2 (s, 3H); 2.8 (t, 2H); 3.2 (t, 2H); 4.4 (q, 2H); 5.1 (s, 2H); 6.9–7.0 (m, 2H); 7.2 (m, 1H); 7.4 (m, 2H); 7.9 (d, 2H).

Step C: Preparation of 4-(3-(2,6-difluorobenzyloxy)phenyl)-4-oxobutyric acid:

Using the method of Example 21, Step C, the title compound was obtained.

¹H NMR (270 MHz, CDCl₃): 2.8 (t, 2H); 3.2 (t, 2H); 5.1 (s, 2H); 6.9–7.0 (m, 2H); 7.2 (m, 1H); 7.4 (m, 2H); 7.9 (d, 2H).

Example 24

Synthesis of 4-(4-((Cyclopropyl)-methoxy)phenyl)-4-oxobutyric acid

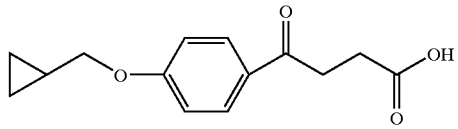

Step A: Preparation of 4-((Cyclopropyl)-methoxy) acetophenone:

Using the method of Example 8, Step A, using Cyclopropylmethyl bromide as the starting material, the title compound was obtained.

$^1$H NMR (270 MHz, CDCl$_3$): 0.4 (m, 2H); 0.6 (m, 2H); 1.2 (m, 1H); 2.5 (s, 3H); 3.8 (d, 2H); 6.9 (d, 2H); 7.9 (d, 2H).

Step B: Preparation of tert-Butyl 4-(4-((cyclopropyl)-methoxy)phenyl)-4-oxobutyrate:

Using the method of Example 8, Step B, the title compound was obtained.

$^1$H NMR (270 MHz, CDCl$_3$): 0.4 (m, 2H); 0.6 (m, 2H); 1.2 (m, 1H); 1.4 (s, 9H); 2.6 (t, 2H); 3.2 (t, 2H); 3.8 (d, 2H); 6.9 (d, 2H); 7.9 (d, 2H).

Step C: Preparation of 4-(4-((Cyclopropyl)-methoxy)phenyl)-4-oxobutyric acid:

Using the method of Example 8, Step C, the title compound was obtained.

$^1$H NMR (270 MHz, CDCl$_3$): 0.4 (m, 2H); 0.6 (m, 2H); 1.2 (m, 1H); 2.8 (t, 2H); 3.2 (t, 2H); 3.8 (d, 2H); 6.9 (d, 2H); 7.9 (d, 2H).

Example 25

Synthesis of 4-(4-(2-Trifluoromethylbenzyloxy)phenyl)-4-oxobutyric acid

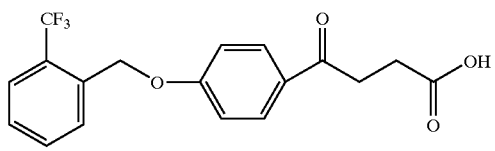

Step A: Preparation of 4-(2-Trifluoromethylbenzyloxy) acetophenone:

Using the method of Example 8, Step A, using 2-(Trifluoromethyl)benzyl bromide as the starting material, the title compound was obtained.

$^1$H NMR (270 MHz, CDCl$_3$): 2.5 (s, 3H); 5.3 (s, 2H); 6.9 (d, 2H); 7.4 (t, 1H); 7.6 (t, 1H); 7.7 (d, 2H); 7.9 (d, 2H).

Step B: Preparation of tert-Butyl 4-(4-(2-trifluoromethylbenzyloxy)phenyl)-4-oxobutyrate:

Using the method of Example 8, Step B, the title compound was obtained.

$^1$H NMR (270 MHz, CDCl$_3$): 1.4 (s, 9H); 2.7 (t, 2H); 3.2 (t, 2H); 5.3 (s, 2H); 6.9 (d, 2H); 7.4 (t, 1H); 7.6 (t, 1H); 7.7 (d, 2H); 7.9 (d, 2H).

Step C: Preparation of 4-(4-(2-Trifluoromethylbenzyloxy)phenyl)-4-oxobutyric acid:

Using the method of Example 8, Step C, the title compound was obtained.

$^1$H NMR (270 MHz, CDCl$_3$): 2.8 (t, 2H); 3.2 (t, 2H); 5.3 (s, 2H); 6.9 (d, 2H); 7.4 (t, 1H); 7.6 (t, 1H); 7.7 (d, 2H); 7.9 (d, 2H).

Example 26

Synthesis of 3-[(4-(2,6-Difluorobenzyloxy)phenyl)-methylthio]propionic acid

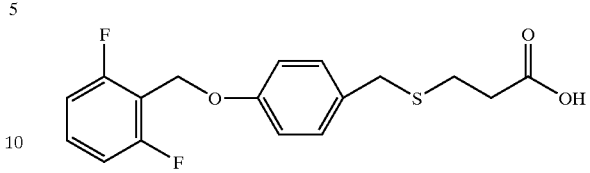

Step A: Preparation of 4-Hydroxybenzyl bromide:

Using the method of Example 3, Step A, the title compound was obtained which was used without further purification.

Step B: Preparation of Ethyl 3-[(4-hydroxyphenyl)-methylthio]propionate:

Using the method of Example 3, Step B, the title compound was obtained.

$^1$H NMR (270 MHz, CDCl$_3$): 1.2 (t, 3H); 2.4–2.6 (m, 4H); 3.6 (s, 2H); 4.1 (q, 2H); 6.7 (d, 2H); 7.2 (d, 2H).

Step C: Preparation of Ethyl 3-[(4-(2,6-difluorobenzyloxy)phenyl)methylthio]propionate:

Using the method of Example 3, Step C, using 2,6-Difluorobenzyl bromide as the starting material, the title compound was obtained.

$^1$H NMR (270 MHz, CDCl$_3$): 1.2 (t, 3H); 2.4–2.6 (m, 4H); 3.6 (s, 2H); 4.2 (q, 2H); 5.15 (s, 2H); 6.9 (d, 4H); 7.2–7.4 (m, 3H).

Step D: Preparation of 3-[(4-(2,6-Difluorobenzyloxy)phenyl)-methylthio]propionic acid:

Using the method of Example 3, Step D, the title compound was obtained.

$^1$H NMR (270 MHz, CDCl$_3$): 2.5–2.6 (m, 4H); 3.7 (s, 2H); 5.1 (s, 2H); 6.9–7.0 (m, 4H); 7.2–7.4 (m, 3H).

Example 27

Synthesis of 4-(2-(2,6-Difluorobenzyloxy)phenyl)-4-oxobutyric acid

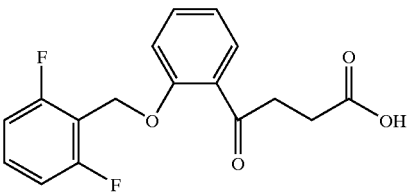

Step A: Preparation of 2-(2,6-Difluorobenzyloxy) acetophenone:

Using the method of Example 8, Step A, using 2-Hydroxyacetophenone as the starting material, the title compound was obtained.

$^1$H NMR (270 MHz, CDCl$_3$): 2.5 (s, 3H); 5.2 (s, 2H); 6.9–7.0 (m, 3H); 7.1 (d, 1H); 7.4 (m, 1H); 7.5 (t, 1H); 7.8 (d, 1H).

Step B: Preparation of Ethyl 4-(2-(2,6-difluorobenzyloxy)phenyl)-4-oxobutyrate:

Using the method of Example 17, Step B, the title compound was obtained.

$^1$H NMR (270 MHz, CDCl$_3$): 1.2 (s, 3H); 2.6 (t, 2H); 3.2 (t, 2H); 4.1 (q, 2H); 5.2 (s, 2H); 6.9–7.0 (m, 3H); 7.1 (d, 1H); 7.4 (m, 1H); 7.5 (t, 1H); 7.8 (d, 1H).

Step C: Preparation of 4-(2-(2,6-Difluorobenzyloxy) phenyl)-4-oxobutyric acid:

Using the method of Example 21, Step C, the title compound was obtained.

$^1$H NMR (270 MHz, CDCl$_3$): 2.6 (t, 2H); 3.2 (t, 2H); 5.2 (s, 2H); 6.9–7.0 (m, 3H); 7.1 (d, 1H); 7.4 (m, 1H); 7.5 (t, 1H); 7.8 (d, 1H).

Example 28

Synthesis of Ethyl 4-(4-(2,6-difluorobenzyloxy) phenyl)-3-oxobutyrate

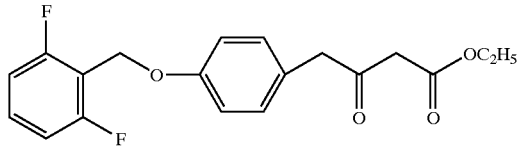

Step A: Preparation of Ethyl 4-hydroxybenzylate:

To a stirred solution of 4-Hydroxybenzyl alcohol (4 g, 26.28 mmol) in dry DMF (15 ml), pyridine (1 ml) and N,N-Dicyclohexylcarbodiimide (6.50 g, 31.5 mmol) was added abs EtOH (3.26 g, 78.84 mmol). The reaction mixture was stirred for 18 hours at room temperature and then filtered. The filtrate was concentrated under reduced pressure and purified by flash chromatography on silica gel column (hex:ethyl acetate, 2:1) to provide the title compound.

$^1$H NMR (270 MHz, CDCl$_3$): 1.2 (t, 3H); 3.5 (s, 2H); 4.1 (q, 2H); 6.7 (d, 2H); 7.1 (d, 2H).

Step B: Preparation of Ethyl 4-(2,6-difluorobenzyloxy) benzylate:

To a solution of NaH (60% dispersed in oil, 0.393 g, 9.8 mmol) in dry DMF (20 ml) was added Ethyl 4-hydroxybenzylate (Step A, 1.59 g, 8.8 mmol). When the evolution of hydrogen ceased, 2,6-Difluorobenzyl bromide (1.64 g, 7.9 mmol) was added. The reaction mixture was stirred for 4 hours at room temperature, quenched with sat. NH$_4$Cl, and concentrated in vacuo. The residue was taken in EtOAc and washed twice with water and brine. The organic layer was dried over Na$_2$SO$_4$, filtered, concentrated and purified by flash chromatography on silica gel column (hex:ethyl acetate, 2:1) to provide the title compound.

$^1$H NMR (270 MHz, CDCl$_3$): 1.2 (t, 3H); 3.5 (s, 2H); 4.1 (q, 2H); 5.1 (s, 2H); 6.9 (m, 4H); 7.2–7.4 (m, 3H).

Step C: Preparation of 4-(2,6-Difluorobenzyloxy)benzylic acid:

To a stirred solution of Ethyl 4-(2,6-difluorobenzyloxy) benzylate (Step B, 2.14 g, 6.9 mmol) in abs EtOH (30 ml) was added 1N NaOH (10 ml) at room temperature. The reaction mixture was stirred for 3 hours, acidified by 1M HCl and filtered. The white precipitate was washed with water and dried under high vacuum to provide the title compound.

$^1$H NMR (270 MHz, CDCl$_3$): 3.6 (s, 2H); 5.1 (s, 2H); 6.9 (m, 4H); 7.2–7.4 (m, 3H).

Step D: preparation of 4-(2,6-Difluorobenzyloxy) benzylcarbonyl chloride:

Thionyl chloride (10 ml) was added to 4-(2,6 Difluorobenzyloxy)benzylic acid (Step C, 1.61 g, 5.79 mmol). The reaction mixture was refluxed for 3 hours and concentrated in vacuo to provide light yellow oil which was used without further purification.

Step E: Ethyl 4-(4-(2,6-difluorobenzyloxy)phenyl)-3-oxobutyrate:

To a solution of Meldrum's acid (0.846 g, 5.8 mmol) in dichloromethane (5 ml) was added pyridine (2 ml) over a period of 10 minutes at 0° C. To this solution was added 4-(2,6-Difluorobenzyloxy)benzylcarbonyl chloride (Step D, 1.71 g, 5.7 mmol) in dichloromethane (5 ml), which resulted in an orange solution. The dark orange solution was stirred for 1 hour at 0° C., allowed to warm to room temperature and stirred for an additional hour. The reaction mixture was diluted with dichloromethane and poured onto 2M HCl and ice. The phases were separated and the aqueous phase was extracted twice with dichloromethane. The combined organic layers were washed twice with 2M HCl and brine, dried over Na$_2$SO$_4$, filtered and concentrated to a solid. The solid was suspended in abs EtOH (15 ml) and refluxed for 2.5 hours. The solvent was removed in vacuo to give a dark oil. The residue was purified by flash chromatography on silica gel column (hex:ethyl acetate, 2:1) to provide the title compound as a white solid.

$^1$H NMR (270 MHz, CDCl$_3$): 1.2 (t, 3H); 3.4 (s, 2H); 3.7 (s, 2H); 4.2 (q, 2H); 5.1 (s, 2H); 6.9 (m, 4H); 7.1 (d, 2H); 7.3 (m, 1H).

Example 29

Synthesis of 3-(2-(4-(2,6-Difluorobenzyloxy) phenyl)-2-oxoethyl)thio-1H-1,2,4-triazole

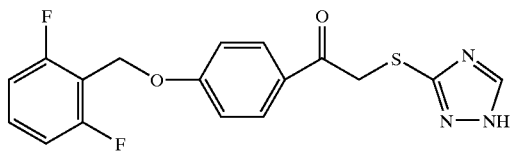

Step A: Preparation of 4-(2,6-Difluorobenzyloxy) acetophenone:

Using the method of Example 8, Step A, the title compound was obtained.

$^1$H NMR (270 MHz, CDCl$_3$): 2.5 (s, 3H); 5.2 (s, 2H); 6.9–7.0 (m, 4H); 7.3–7.4 (m, 1H); 7.9 (d, 2H).

Step B: Preparation of 2-Bromo-1-(4-(2,6-difluorobenzyloxy)phenyl)-1-Ethanone:

To a stirred solution of copper (2) bromide (3.70 g, 16.6 mmol) in ethyl acetate (20 ml) was added a solution of 4-(2,6-Difluorobenzyloxy)acetophenone (Step A, 2.74 g, 10.4 mmol) in chloroform (20 ml) at room temperature. The reaction mixture was refluxed for 16 hours and then water was added. The crude mixture was extracted twice with EtOAc. The organic layers were combined and washed with water, brine, dried over Na$_2$SO$_4$, filtered, concentrated and purified by flash chromatography on silica gel column (hex:ethyl acetate, 4:1) to provide the title compound as a white flaky solid.

$^1$H NMR (270 MHz, CDCl$_3$): 4.4 (s, 2H); 5.2 (s, 2H); 6.9–7.1 (m, 4H), 7.3 (m, 1H); 8.0 (d, 2H).

Step C: Preparation of 3-(2-(4-(2,6-Difluorobenzyloxy) phenyl)-2-oxoethyl)thio-1H-1,2,4-triazole:

To a solution of 1H-1,2,4-Triazole-3-thiol (0.250 g, 2.4 mmol) and triethylamine (2.50 g, 2.4 mmol) in dry dichloromethane (20 ml) was added 2-Bromo-1-(4-(2,6-difluorobenzyloxy)phenyl)-1-Ethanone (Step B, 0.851 g, 2.4 mmol) in dry dichloromethane (5 ml) at room temperature. The reaction mixture was stirred for 50 minutes and then concentrated in vacuo. The crude residue was taken in EtOAc and washed with 0.1M HCl, and brine. The organic layer was dried over Na$_2$SO$_4$, filtered, concentrated and purified by flash chromatography on silica gel column (chloroform:methanol, 9:1) to provide the title compound.

$^1$H NMR (270 MHz, CDCl$_3$): 4.5 (s, 2H); 5.1 (s, 2H); 6.8–7.0 (m, 4H), 7.2 (m, 1H); 7.9 (d, 2H); 8.0 (s, 1H).

Example 30

Synthesis of 5-((4-(2,6-Difluorobenzyloxy)phenyl)-methyl)-1H-tetrazole

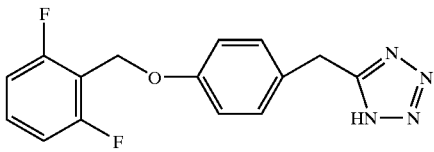

Step A: Preparation of (4-(2,6-Difluorobenzyloxy)phenyl)-acetonitrile:

To a solution of 4-Hydroxybenzyl cyanide (5 g, 37.5 mmol) and $K_2CO_3$ (6.74 g, 48.8 mmol) in dry DMF (20 ml) was added 2,6-Difluorobenzyl bromide (7.77 g, 37.5 mmol). The reaction mixture was stirred for 4 hours at room temperature and concentrated in vacuo. The crude residue was taken in EtOAc and washed with water and brine. The aqueous layer was washed one more time with EtOAc. The combined organic layers were dried over $Na_2SO_4$, filtered, and concentrated to provide the title compound as a white solid.

$^1$H NMR (270 MHz, CDCl$_3$): 3.65 (s, 2H); 5.1 (s, 2H); 6.9–7.0 (m, 4H); 7.2–7.4 (m, 3H);

Step B: Preparation of 5-((4-(2,6-Difluorobenzyloxy)phenyl)-methyl)-1H-tetrazole:

A mixture of (4-(2,6-Difluorobenzyloxy)phenyl)-acetonitrile (Step A, 5 g, 19.3 mmol), NaN$_3$ (1.3 g, 20 mmol), and NH$_4$Cl (1.06 g, 20 mmol) in dry DMF (60 ml) was heated at 90° C. for 16 hours. The solvent was removed in vacuo and the oily residue was partitioned between EtOAc and water (acidified to pH 1 with conc. HCl). The organic layer was washed with water, dried over Na$_2$SO$_4$, filtered and concentrated to a brown semisolid. The purification was done by flash chromatography on silica gel column (chloroform:methanol, 9:1) to provide the title compound as a light creamy solid.

$^1$H NMR (270 MHz, CDCl$_3$): 4.0 (s, 2H); 5.1 (s, 2H); 6.7–6.9 (m, 4H); 7.0 (d, 2H); 7.2 (m, 1H).

Example 31

Synthesis of (2RS)2-(N-Boc)-3-[2-(4-(2,6-difluorobenzyloxy)phenyl)-2-oxoethyl]thiopropionic acid

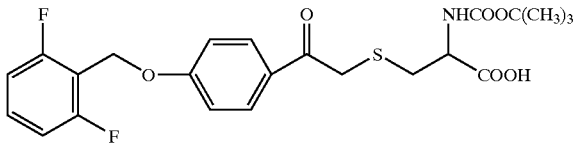

Step A: Preparation of 4-(2,6-Difluorobenzyloxy) acetophenone:

To a solution of 4-Hydroxyacetophenone (3.28 g, 24 mmol) and K$_2$CO$_3$ (4.33 g, 31.3 mmol) in dry DMF (15 ml) was added 2,6-Difluorobenzyl bromide (5 g, 24.1 mmol). The reaction mixture was stirred at room temperature for 5 hours, quenched with water and concentrated in vacuo. The crude residue was taken in EtOAc and washed with water and brine. The aqueous layer was extracted twice with EtOAc. The combined organic layers were dried over Na$_2$SO$_4$, filtered, concentrated and purified by flash chromatography on silica gel column (hex:ethyl acetate, 2:1) to provide the title compound.

$^1$H NMR (270 MHz, CDCl$_3$): 2.5 (s, 3H); 5.2 (s, 2H); 6.9–7.0 (m, 4H); 7.3–7.4 (m, 1H); 7.9 (d, 2H).

Step B: Preparation of 2-Bromo-1-(4-(2,6-difluorobenzyloxy)phenyl)-1-Ethanone:

Using the method of Example 29, Step B, the title compound was obtained.

$^1$H NMR (270 MHz, CDCl$_3$): 4.4 (s, 2H); 5.2 (s, 2H); 6.9–7.1 (m, 4H), 7.3 (m, 1H); 8.0 (d, 2H).

Step C: Preparation of Ethyl (2RS)2-(N-Boc)-3-[2-(4-(2,6-difluorobenzyloxy)phenyl)-2-oxoethyl]thiopropionate:

To a stirred solution of 2-Bromo-1-(4-(2,6-difluorobenzyloxy)phenyl)-1-Ethanone (Step B, 2.07 g, 8.3 mmol) in dry dichloromethane (20 ml) and triethylamine (8.39 g, 83 mmol) was added Boc-Cys-OEt (2.94 g, 8.6 mmol). The reaction mixture was stirred at room temperature for an hour and concentrated in vacuo. The crude residue was taken in EtOAc, washed with 0.1M HCl, and brine. The organic layer was dried over Na$_2$SO$_4$, filtered, concentrated and purified by flash chromatography on silica gel column (chloroform:methanol, 97.5:2.5) to provide the title compound.

$^1$H NMR (270 MHz, CDCl$_3$): 1.2 (t, 3H); 1.4 (s, 9H); 3.0 (m, 2H); 3.8 (s, 2H); 4.2 (q, 2H); 4.5 (br, 1H); 5.2 (s, 2H); 5.4 (d, 1H); 6.9–7.1 (m, 4H); 7.3 (m, 1H); 7.9 (d, 2H).

Step D: Preparation of (2RS)2-(N-Boc)-3-[2-(4-(2,6-difluorobenzyloxy)phenyl)-2-oxoethyl]thiopropionic acid:

To a solution of Ethyl (2RS)2-(N-Boc)-3-[2-(4-(2,6-difluorobenzyloxy)phenyl)-2-oxoethyl]thiopropionate (Step C, 0.761 g, 1.5 mmol) in abs EtOH (10 ml) was added 1N NaOH (3 ml). The reaction mixture was stirred at room temperature for 4 hours, acidified with 1M HCl and concentrated in vacuo. The crude residue was taken in chloroform, and washed with water and brine. The organic layer was dried over Na$_2$SO$_4$, filtered, concentrated and purified by flash chromatography on silica gel column (chloroform:methanol, 92.7:7.5) to provide the title compound.

$^1$H NMR (270 MHz, CDCl$_3$): 1.4 (s, 9H); 3.0 (t, 2H); 4.0 (q, 2H); 4.5 (br, 1H); 5.2 (s, 2H); 5.4 (d, 1H); 6.9–7.1 (m, 4H); 7.3 (m, 1H); 7.9 (d, 2H).

Example 32

Synthesis of Ethyl 2-Hydroxy-4-oxo-4-(4-(2,6-difluorobenzyloxy)phenyl)but-2-enoate

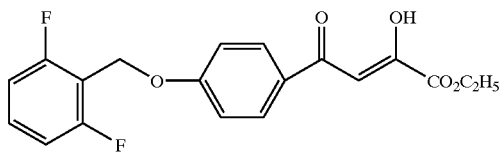

Step A: Preparation of 4-(2,6-Difluorobenzyloxy) acetophenone:

Using the method of example 31, Step A, the title compound was obtained.

$^1$H NMR (270 MHz, CDCl$_3$): 2.5 (s, 3H); 5.2 (s, 2H); 6.9–7.0 (m, 4H); 7.3–7.4 (m, 1H); 7.9 (d, 2H).

Step B: Preparation of Ethyl 2-Hydroxy-4-oxo-4-(4-(2,6-difluorobenzyloxy)phenyl)but-2-enoate:

A mixture of 4-(2,6-Difluorobenzyloxy)acetophenone (Step A, 5.64 g, 21.5 mmol) and diethyl oxalate (3.14 g, 21.5 mmol) was added to an ice-cooled solution of NaOEt (0.490 g, 22.4 mmol of metallic Na) in abs EtOH (25 ml). After being allowed to stand overnight at room temperature, the mixture was diluted with water (50 ml), acidified with 10% HCl, and extracted thrice with EtOAc. The combined organic layers were washed with brine, dried over Na₂SO₄, filtered, concentrated and purified by flash chromatography on silica gel column (hex:ethyl acetate, 4:1) to provide the title compound.

¹H NMR (270 MHz, CDCl₃): 1.4 (t, 3H); 4.4 (q, 2H); 5.2 (s, 2H); 6.9–7.1 (m, 5H); 7.3–7.4 (m, 1H); 8.0 (d, 2H).

Example 33

Synthesis of (2RS)2-(N-Acetyl)-4-(4-(2,6-difluorobenzyloxy)phenyl)-4-oxobutyric acid

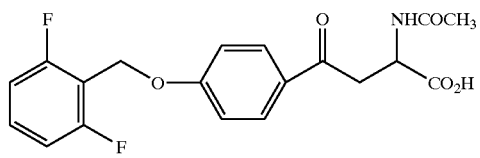

Step A: Preparation of 4-(2,6-Difluorobenzyloxy) acetophenone:

Using the method of example 31, Step A, the title compound was obtained.

¹H NMR (270 MHz, CDCl₃): 2.5 (s, 3H); 5.2 (s, 2H); 6.9–7.0 (m, 4H); 7.3–7.4 (m, 1H); 7.9 (d, 2H).

Step B: Preparation of 2-Bromo-1-(4-(2,6-difluorobenzyloxy)phenyl)-1-Ethanone:

Using the method of Example 29, Step B, the title compound was obtained.

¹H NMR (270 MHz, CDCl₃): 4.4 (s, 2H); 5.2 (s, 2H); 6.9–7.1 (m, 4H), 7.3 (m, 1H); 8.0 (d, 2H).

Step C: Preparation of Diethyl (N-Acetyl)(2-(4-(2,6-difluorobenzyloxy)phenyl)-2-oxoethyl)propanedioate:

To a solution of Diethyl acetamidomalonate (0.949 g, 4.3 mmol) and NaOEt (0.301 g, 4.4 mmol) in abs EtOH (25 ml) was added 2-Bromo-1-(4-(2,6-difluorobenzyloxy)phenyl)-1-Ethanone (Step B, 1.42 g, 4.1 mmol). The reaction mixture was stirred at room temperature for 2 hours and concentrated in vacuo. The crude residue was partitioned between EtOAc and 0.01 N NaOH. The organic layer was washed with water and 0.001 M HCl, dried over Na₂SO₄, filtered and concentrated. The purification was done by flash chromatography on silica gel column (hex:ethyl acetate, 2:1) to provide the title compound.

¹H NMR (270 MHz, CDCl₃): 1.2 (t, 6H); 2.0 (s, 3H); 4.2–4.3 (m, 6H); 5.2 (s, 2H); 6.9–7.1 (m, 4H), 7.3–7.4 (m, 1H); 7.9 (d, 2H).

Step D: Preparation of (2RS)2-(N-Acetyl)-4-(4-(2,6-difluorobenzyloxy)phenyl)-4-oxobutyric acid:

To a solution of Diethyl (N-Acetyl)(2-(4-(2,6-difluorobenzyloxy)phenyl)-2-oxoethyl)propanedioate (Step C, 1.28 g, 2.6 mmol) in water (20 ml) was added NaOH (0.529 g, 13.2 mmol). The reaction mixture was refluxed for 16 hours, then glacial acetic acid (18 ml) was added and refluxing continued for an additional 3 hours. The mixture was concentrated in vacuo and purified by flash chromatography on silica gel column (chloroform:methanol, 9:1) to provide the title compound.

¹H NMR (270 MHz, CDCl₃:CD₃OD): 2.0 (s, 3H); 3.5 (m, 2H); 4.8 (t, 1H); 5.1 (s, 2H); 6.9–7.1 (m, 4H), 7.3–7.4 (m, 1H); 7.9 (d, 2H).

Example 34

Synthesis of 4-(3-((Cyclopropyl)-methoxy)phenyl)-4-oxobutyric acid

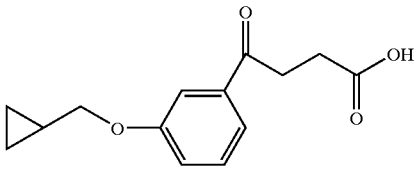

Step A: Preparation of 3-((Cyclopropyl)-methoxy) acetophenone:

Using the method of Example 31, Step A, using Cyclopropylmethyl bromide and 3-Hydroxyacetophenone as the starting materials, the title compound was obtained.

¹H NMR (270 MHz, CDCl₃): 0.4 (m, 2H); 0.6 (m, 2H); 1.2 (m, 1H); 2.5 (s, 3H); 3.8 (d, 2H); 7.1 (m, 1H); 7.4 (m, 1H); 7.5–7.6 (m, 2H).

Step B: Preparation of tert-Butyl 4-(3-((cyclopropyl)-methoxy)phenyl)-4-oxobutyrate:

Using the method of Example 8, Step B, the title compound was obtained.

¹H NMR (270 MHz, CDCl₃): 0.4 (m, 2H); 0.6 (m, 2H); 1.2 (m, 1H); 1.4 (s, 9H); 2.6 (t, 2H); 3.2 (t, 2H); 3.8 (d, 2H); 7.1 (m, 1H); 7.4 (m, 1H); 7.5–7.6 (m, 2H).

Step C: Preparation of 4-(3-((Cyclopropyl)-methoxy) phenyl)-4-oxobutyric acid:

Using the method of Example 8, Step C, the title compound was obtained.

¹H NMR (270 MHz, CDCl₃): 0.4 (m, 2H); 0.6 (m, 2H); 1.2 (m, 1H); 2.8 (t, 2H); 3.2 (t, 2H); 3.8 (d, 2H); 7.1 (m, 1H); 7.4 (m, 1H); 7.5–7.6 (m, 2H).

Example 35

Synthesis of 4-(3-(2,6-Dimethylbenzyloxy)phenyl)-4-oxobutyric acid

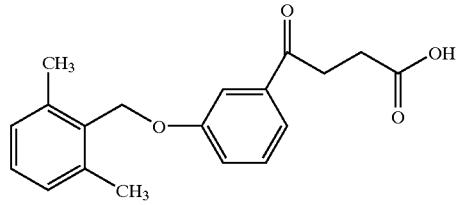

Step A: Preparation of 2,6-Dimethylbenzyl Alcohol:

To a solution of 2,6-dimethylbenzoic acid (10 g, 66.5 mmol) and potassium carbonate (9.18 g, 66.5 mmol) in dimethylformamide (67 ml), was added methyl iodide (8.28 ml, 133.16 mmol) in an ice bath, and the mixture was stirred for 16 hours. To the reaction mixture was added toluene and water, and the organic layer was washed with 3% K₂CO₃, 1N HCl, and brine. The organic layer was dried over Na₂SO₄, filtered and concentrated. The oily residue was redissolved in dry THF (135 ml), added to LiAlH₄ (3.79 g, 99.8 mmol), and stirred for 4 hours in an ice bath. To the reaction mixture was added 1N HCl slowly followed by ethyl acetate, and the organic layer was washed with brine, dried over Na₂SO₄, filtered and concentrated. The oily residue was used without further purification.

¹H NMR (270 MHz, CDCl₃): 2.4 (s, 6H); 4.7 (s, 2H); 7.0–7.15 (m, 3H).

89

Step B: Preparation of 3-(2,6-Dimethylbenzyloxy) acetophenone:

To a stirred solution of 3'-Hydroxyacetophenone (8.07 g, 59.24 mmol) and Triphenylphosphine (16.93 g, 64.5 mmol) in dry THF (180 ml) was added dropwise 2,6-Dimethylbenzyl alcohol (8.05 g, 59.24 mmol) and diethyl azodicarboxylate (11.24 g, 64.57 mmol) in dry THF (45 ml) and dry DMF (18 ml) at ambient temperature. After stirring for 1.5 hours at ambient temperature, the reaction mixture was diluted with ether and washed twice with water, 1N NaOH and brine, dried over $Na_2SO_4$, filtered and concentrated. The purification was done by flash chromatography on silica gel column (hex:ethyl acetate, 2:1) to provide the title compound.

$^1$H NMR (270 MHz, $CDCl_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy) phenyl)-4-oxobutyrate:

Using the method of Example 17, Step B, the title compound was obtained.

$^1$H NMR (270 MHz, $CDCl_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of 4-(3-(2,6-Dimethylbenzyloxy) phenyl)-4-oxobutyric acid:

To a solution of Ethyl 4-(3-(2,6-dimethylbenzyloxy) phenyl)-4-oxobutyrate (Step C, 12.31 g, 36.2 mmol) in abs ethanol (160 ml) was added 1N NaOH (50 ml) at room temperature. The reaction mixture was stirred for 3 hours and then acidified with 1M HCl. The occuring white precipitate was filtered, washed with water and dried under vacuum to provide the title compound as a white solid.

$^1$H NMR (270 MHz, $CDCl_3$): 2.4 (s, 6H); 2.8 (t, 2H); 3.3 (t, 2H); 5.1 (s, 2H); 7.1 (d, 2H); 7.2–7.3 (m, 2H); 7.4 (t, 1H); 7.6 (m, 2H).

Example 36

Synthesis of 4-(3-(2-Fluoro-6-methylbenzyloxy) phenyl)-4-oxobutyric acid

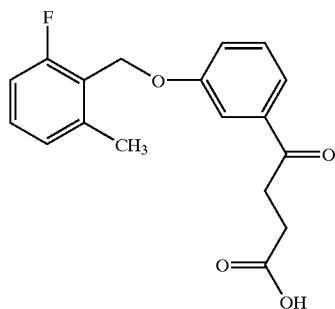

Step A: Preparation of 2-Fluoro-6-methylbenzoic Acid:

Synthesized as described in Example 89(d) of International Patent Publication No. WO 97/34893, page 43.

Step B: Preparation of 2-Fluoro-6-methylbenzyl Alcohol:

Using the method of Example 35, Step A, the title compound was obtained.

$^1$H NMR (270 MHz, $CDCl_3$): 2.4 (s, 3H); 4.7 (s, 2H); 6.85 (t, 1H); 6.95 (d, 1H); 7.15 (m, 1H).

Step C: Preparation of 3-(2-Fluoro-6-methylbenzyloxy) acetophenone:

Using the method of Example 35, Step B, the title compound was obtained.

$^1$H NMR (270 MHz, $CDCl_3$): 2.4 (s, 3H); 2.6 (s, 3H); 5.1 (s, 2H); 7.1 (m, 2H); 7.2 (m, 2H); 7.4 (t, 1H); 7.6 (m, 2H).

90

Step D: Preparation of Ethyl 4-(3-(2-Fluoro-6-methylbenzyloxy)phenyl)-4-oxobutyrate:

Using the method of Example 17, Step B, the title compound was obtained.

$^1$H NMR (270 MHz, $CDCl_3$): 1.2 (s, 3H); 2.4 (s, 3H); 2.8 (t, 2H); 3.3 (t, 2H); 4.4 (q, 2H); 5.2 (s, 2H); 6.9–7.1 (m, 2H); 7.2 (m, 2H); 7.4 (t, 1H); 7.6 (m, 2H).

Step E: Preparation of 4-(3-(2-Fluoro-6-methylbenzyloxy) phenyl)-4-oxobutyric acid:

To a solution of Ethyl 4-(3-(2-Fluoro-6-methylbenzyloxy) phenyl)-4-oxobutyrate (Step D, 8.56 g, 24.9 mmol) in abs ethanol (100 ml) was added 1N NaOH (40 ml) at room temperature. The reaction mixture was stirred for 3 hours, acidified with 1M HCl and concentrated. The residue was taken in chloroform and washed with 0.1 M HCl, brine, dried over $Na_2SO_4$, filtered and concentrated. The purification was done by flash chromatography on silica gel column (chloroform:methanol 95:5 spiked with acetic acid) to provide the title compound as white solid.

$^1$H NMR (270 MHz, $CDCl_3$): 2.4 (s, 3H); 2.8 (t, 2H); 3.3 (t, 2H); 5.1 (s, 2H); 6.9–7.1 (m, 2H); 7.2 (m, 2H); 7.4 (t, 1H); 7.6 (m, 2H).

Example 37

Synthesis of Ethyl 4-(3-(2,6-dimethylbenzyloxyl) phenyl)-4-oxobutyrate

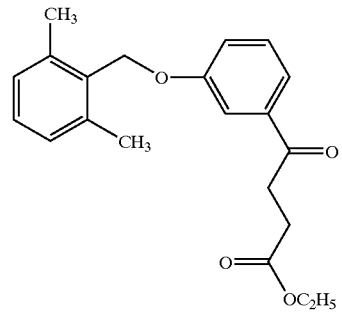

Step A: Preparation of 2,6-Dimethylbenzyl Alcohol:

Using the method of Example 35, Step A, the title compound was obtained.

$^1$H NMR (270 MHz, $CDCl_3$): 2.4 (s, 6H); 4.7 (s, 2H); 7.0–7.15 (m, 3H).

Step B: Preparation of 3-(2,6-Dimethylbenzyloxy) acetophenone:

Using the method of Example 35, Step B, the title compound was obtained.

$^1$H NMR (270 MHz, $CDCl_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy) phenyl)-4-oxobutyrate:

Using the method of Example 17, Step B, the title compound was obtained.

$^1$H NMR (270 MHz, $CDCl_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Example 38

Synthesis of 4-(3-(2,6-Dimethylbenzyloxy)phenyl)-4-oxobutyric acid Sodium salt

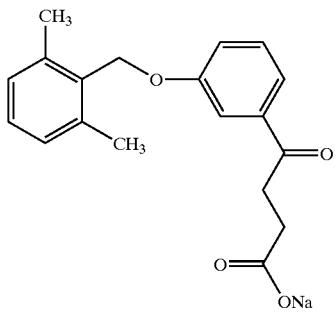

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 3-(2,6-Dimethylbenzyloxy) acetophenone:

Using the method of Example 35, Step B, the title compound was obtained.

$^1$H NMR (270 MHz, CDCl$_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy) phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of 4-(3-(2,6-Dimethylbenzyloxy) phenyl)-4-oxobutyric acid:

Using the method of Example 36, Step E, the title compound was obtained.

$^1$H NMR (270 MHz, CDCl$_3$): 2.4 (s, 6H); 2.8 (t, 2H); 3.3 (t, 2H); 5.1 (s, 2H); 7.1 (d, 2H); 7.2–7.3 (m, 2H); 7.4 (t, 1H); 7.6 (m, 2H).

Step E: Preparation of 4-(3-(2,6-Dimethylbenzyloxy) phenyl)-4-oxobutyric acid Sodium salt:

The 4-(3-(2,6-Dimethylbenzyloxy)phenyl)-4-oxobutyric acid (Step D, 5.5 g, 17.6 mmol) was dissolved in abs ethanol (20 ml) by warming gently followed by addition of NaOH (0.705 g) at 0° C. temperature. The reaction mixture was stirred for one hour, concentrated in vaccuo and lyophilized to give as a white solid.

$^1$H NMR (270 MHz, D$_2$O): 2.0 (s, 6H); 2.5 (t, 2H); 3.0 (t, 2H); 4.8 (s, 2H); 6.8 (d, 2H); 6.9 (m, 2H); 7.2 (t, 1H); 7.5 (d, 2H).

Example 39

Synthesis of 4-(4-(2,6-Dimethylbenzyloxy)phenyl)-4-oxobutyric acid

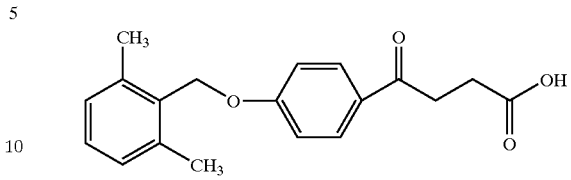

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 4-(2,6-Dimethylbenzyloxy) acetophenone:

Using the method of Example 35, Step B, the title compound was obtained.

$^1$H NMR (270 MHz, CDCl$_3$): 2.4 (s, 6H); 2.6 (s, 3H); 5.1 (s, 2H); 7.0–7.2 (m, 5H); 8.0 (d, 2H).

Step C: Preparation of Ethyl 4-(4-(2,6-dimethylbenzyloxy) phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.3 (t, 2H); 4.4 (q, 2H); 5.1 (s, 2H); 7.0–7.2 (m, 5H); 8.0 (d, 2H).

Step D: Preparation of 4-(4-(2,6-Dimethylbenzyloxy) phenyl)-4-oxobutyric acid:

Using the method of Example 36, Step E, the title compound was obtained.

$^1$H NMR (270 MHz, CDCl$_3$): 2.4 (s, 6H); 2.8 (t, 2H); 3.3 (t, 2H); 5.1 (s, 2H); 7.0–7.2 (m, 5H); 8.0 (d, 2H).

Example 40

Synthesis of 4-(3-(2,6-Dimethylbenzyloxy)phenyl)-4-oxobutyric acid Potassium salt

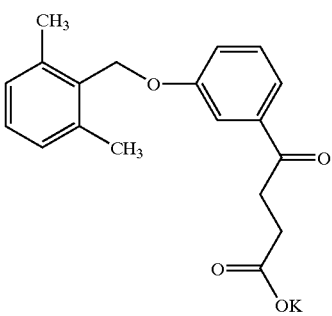

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 3-(2,6-Dimethylbenzyloxy) acetophenone:

Using the method of Example 35, Step B, the title compound was obtained.

$^1$H NMR (270 MHz, CDCl$_3$): 2.3 (s, 6H); 2.6 (s, 3H); 5.1 (s, 2H); 7.1 (d, 2H); 7.2 (m, 2H); 7.45 (t, 1H); 7.6 (m, 2H).

Step C: Preparation of Ethyl 4-(3-(2,6-dimethylbenzyloxy)phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.45 (t, 1H); 7.6 (m, 2H).

Step D: Preparation of 4-(3-(2,6-Dimethylbenzyloxy)phenyl)-4-oxobutyric acid:

Using the method of Example 36, Step E, the title compound was obtained.

$^1$H NMR (270 MHz, CDCl$_3$): 2.4 (s, 6H); 2.5 (t, 2H); 3.2 (t, 2H); 5.1 (s, 2H); 7.1 (d, 2H); 7.2–7.3 (m, 2H); 7.45 (t, 1H); 7.6 (m, 2H).

Step E: Preparation of 4-(3-(2,6-Dimethylbenzyloxy)phenyl)-4-oxobutyric acid Potassium salt:

The 4-(3-(2,6-Dimethylbenzyloxy)phenyl)-4-oxobutyric acid (Step D, 6.0 g, 19.4 mmol) was dissolved in abs ethanol (20 ml) by warming gently followed by addition of KOH (1.21 g) at 0° C. temperature. The reaction mixture was stirred for one hour, concentrated in vaccuo and lyophilized to give the title compound as white solid.

$^1$H NMR (270 MHz, D$_2$O): 2.3 (s, 6H); 2.5 (t, 2H); 3.3 (t, 2H); 5.1 (s, 2H); 7.1 (d, 2H); 7.2–7.3 (m, 2H); 7.45 (t, 1H); 7.6 (m, 2H).

Example 41

Synthesis of 4-(3-(2,6-Dimethoxybenzyloxy)phenyl)-4-oxobutyric acid

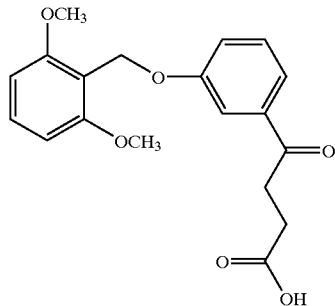

Step A: Preparation of 2,6-Dimethoxylbenzyl Alcohol:

Using the method of Example 35, Step A, the title compound was obtained.

$^1$H NMR (270 MHz, CDCl$_3$): 3.9 (s, 6H); 4.8 (s, 2H); 6.5 (d, 2H); 7.25 (m, 1H).

Step B: Preparation of 3-(2,6-Dimethoxybenzyloxy)acetophenone:

Using the method of Example 35, Step B, the title compound was obtained.

$^1$H NMR (270 MHz, CDCl$_3$): 2.6 (s, 3H); 3.9 (s, 6H); 5.2 (s, 2H); 6.6 (d, 2H); 7.3 (m, 3H); 7.5 (d, 1H); 7.7 (d, 1H).

Step C: Preparation of Ethyl 4-(3-(2,6-dimethoxybenzyloxy)phenyl)-4-oxobutyrate:

Using the method of Example 17, Step B, the title compound was obtained.

$^1$H NMR (270 MHz, CDCl$_3$): 1.2 (t, 3H); 2.8 (t, 2H); 3.3 (t, 2H); 3.8 (s, 6H); 4.1 (q, 2H); 5.2 (s, 2H); 6.5 (d, 2H); 7.3–7.4 (m, 3H); 7.6 (d, 1H); 7.7 (d, 1H).

Step D: Preparation of 4-(3-(2,6-dimethoxybenzyloxy)phenyl)-4-oxobutyric acid:

Using the method of Example 36, Step E, the title compound was obtained.

$^1$H NMR (270 MHz, CDCl$_3$): 2.8 (t, 2H); 3.3 (t, 2H); 3.8 (s, 6H); 5.2 (s, 2H); 6.5 (d, 2H); 7.3–7.4 (m, 3H); 7.6 (d, 1H); 7.7 (d, 1H).

Example 42

Synthesis of 4-(3-(2,6-Dimethylbenzyloxy)phenyl)-4-oxo-2,2-dimethylbutyric acid

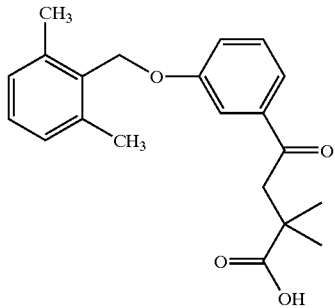

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 3-(2,6-Dimethylbenzyloxy)acetophenone:

Using the method of Example 35, Step B, the title compound was obtained.

$^1$H NMR (270 MHz, CDCl$_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy)phenyl)-4-oxo-2,2-dimethylbutyrate:

To a stirred solution of 3-(2,6-Dimethylbenzyloxy)acetophenone (Step B, 4.11 g, 16.1 mmol) in dry THF (60 ml) and DMPU (12 ml) was added a solution of lithium bis(trimethylsilyl)amide (1.0M, 17.74 ml) at −60° C. under argon. After stirring for 10 minutes at −60° C., Ethyl 2-bromoisobutyrate (4.73 g, 24.2 mmol) was added rapidly. The reaction mixture was stirred for an additional 10 minutes and then warmed to room temperature for 4 hours. The crude mixture was taken in EtOAc and washed with water. The aqueous layer was extracted one more time with EtOAc. The combined organic layers were washed with brine, dried over Na$_2$SO$_4$, filtered, concentrated and purified by flash chromatography on silica gel column (hex:ethyl acetate, 4:1) to provide the title compound as white solid.

$^1$H NMR (270 MHz, CDCl$_3$): 1.2 (t, 3H); 1.3 (s, 6H); 2.3 (s, 6H); 3.3 (s, 2H); 4.1 (q, 2H); 5.1 (s, 2H); 7.1 (d, 2H); 7.2 (m, 2H); 7.4 (t, 1H); 7.6 (m, 2H).

Step D: Preparation of 4-(3-(2,6-Dimethylbenzyloxy)phenyl)-4-oxo-2,2-dimethylbutyric acid:

Using the method of Example 36, Step E, the title compound was obtained.

$^1$H NMR (270 MHz, CDCl$_3$): 1.3 (s, 6H); 2.3 (s, 6H); 3.3 (s, 2H); 5.1 (s, 2H); 7.1 (d, 2H); 7.2 (m, 2H); 7.4 (t, 1H); 7.6 (m, 2H).

Example 43

Synthesis of 4-(3-(4-(Trifluoromethyl)benzyloxy)phenyl)-4-oxobutyric acid:

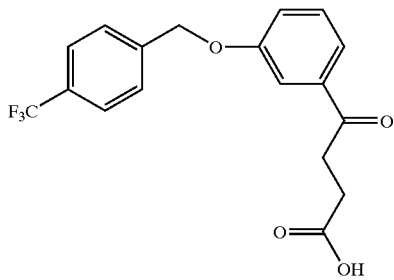

Step A: Preparation of 3-(4-(Trifluoromethyl)benzyloxy) acetophenone:

Using the method of Example 31, Step A, using 4-(Trifluoromethyl)benzyl bromide and 3-Hydroxyacetophenone as the starting materials, the title compound was obtained.

$^1$H NMR (270 MHz, CDCl$_3$): 2.5 (s, 3H); 5.1 (s, 2H); 7.1 (d, 2H); 7.4–7.6 (m, 6H).

Step B: Preparation of Ethyl 4-(3-(4-(trifluoromethyl)benzyloxy)phenyl)-4-oxobutyrate:

Using the method of Example 17, Step B, the title compound was obtained.

$^1$H NMR (270 MHz, CDCl$_3$): 1.3 (t, 3H); 2.7 (t, 2H); 3.3 (t, 2H); 4.1 (q, 2H); 5.1 (s, 2H); 7.1 (d, 2H); 7.4–7.6 (m, 6H).

Step C: Preparation of 4-(3-(4-(Trifluoromethyl)benzyloxy)phenyl)-4-oxobutyric acid:

Using the method of Example 36, Step E, the title compound was obtained.

$^1$H NMR (270 MHz, CDCl$_3$): 2.7 (t, 2H); 3.3 (t, 2H); 5.1 (s, 2H); 7.1 (d, 2H); 7.4–7.6 (m, 6H).

Example 44

Synthesis of 4-(3-((Cyclobutyl)-methoxy)phenyl)-4-oxobutyric acid

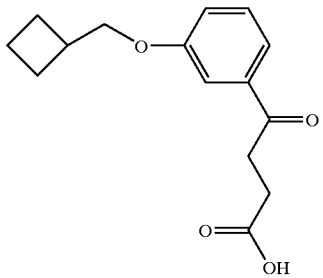

Step A: Preparation of 3-((Cyclobutyl)-methoxy) acetophenone:

Using the method of Example 31, Step A, using Cyclobutylmethyl bromide and 3-Hydroxyacetophenone as the starting materials, the title compound was obtained.

$^1$H NMR (270 MHz, CDCl$_3$): 1.9 (m, 4H); 2.1 (m, 2H); 2.5 (s, 3H); 2.7 (m, 1H); 4.0 (d, 2H); 7.1 (dd, 1H); 7.4 (t, 1H); 7.5–7.6 (m, 2H).

Step B: Preparation of Ethyl 4-(3-((cyclobutyl)-methoxy)phenyl)-4-oxobutyrate:

Using the method of Example 35, Step C, the title compound was obtained.

$^1$H NMR (270 MHz, CDCl$_3$): 1.2 (t, 3H); 1.9 (m, 4H); 2.1 (m, 2H); 2.7 (m, 1H); 2.8 (t, 2H); 3.3 (t, 2H); 4.0 (d, 2H); 4.1 (q, 2H); 7.1 (dd, 1H); 7.4 (t, 1H); 7.5–7.6 (m, 2H).

Step C: Preparation of 4-(3-((Cyclobutyl)-methoxy)phenyl)-4-oxobutyric acid:

Using the method of Example 36, Step E, the title compound was obtained.

$^1$H NMR (270 MHz, CDCl$_3$): 1.9 (m, 4H); 2.1 (m, 2H); 2.7 (m, 1H); 2.8 (t, 2H); 3.3 (t, 2H); 4.0 (d, 2H); 7.1 (dd, 1H); 7.4 (t, 1H); 7.5–7.6 (m, 2H).

Example 45

Synthesis of 4-(3-(2,6-Dimethylbenzyloxy)phenyl) butyric acid

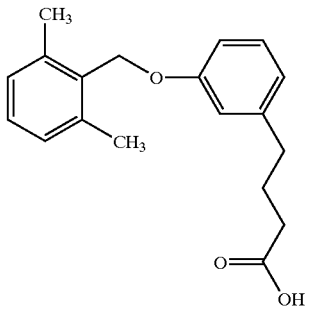

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 3-(2,6-Dimethylbenzyloxy) acetophenone:

Using the method of Example 35, Step B, the title compound was obtained.

$^1$H NMR (270 MHz, CDCl$_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy)phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of 4-(3-(2,6-Dimethylbenzyloxy)phenyl)-4-oxobutyric acid:

Using the method of Example 36, Step E, the title compound was obtained.

$^1$H NMR (270 MHz, CDCl$_3$): 2.4 (s, 6H); 2.8 (t, 2H); 3.3 (t, 2H); 5.1 (s, 2H); 7.1 (d, 2H); 7.2–7.3 (m, 2H); 7.4 (t, 1H); 7.6 (m, 2H).

Step E: Preparation of 4-(3-(2,6-Dimethylbenzyloxy) phenyl)butyric acid:

A solution of 4-(3-(2,6-Dimethylbenzyloxy)phenyl)-4-oxobutyric acid (Step D, 3 g, 9.6 mmol), hydrazine (1.41 ml, 28.8 mmol) and potassium hydroxide (1.61 g, 28.8 mmol) in ethylene glycol (12 ml) was refluxed for 4 h, water (18 ml) and 6 N HCl (10 ml) were added to the reaction mixture. The crude reaction mixture was concentrated, and the residue was dissolved in EtOAc, washed with water and brine, dried over Na$_2$SO$_4$, filtered, and concentrated. The purification was done by flash chromatography on silica gel column (chloroform:methanol 95:5 spiked with acetic acid) to provide the title compound as a white solid.

$^1$H NMR (270 MHz, CDCl$_3$): 2.4 (m, 8H); 2.8 (t, 2H); 3.3 (t, 2H); 5.1 (s, 2H); 7.1 (d, 2H); 7.2–7.3 (m, 2H); 7.4 (t, 1H); 7.6 (m, 2H).

Example 46

Synthesis of 4-[[4-(2,6-Dimethylbenzyloxy)-3-methoxy]phenyl]-4-oxobutyric acid

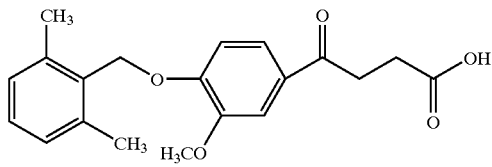

Step A: Preparation of 2,6-Dimethylbenzyl Alcohol:
Using the method of Example 35, Step A, the title compound was obtained.
$^1$H NMR (270 MHz, CDCl$_3$): 2.4 (s, 6H); 4.7 (s, 2H); 7.0–7.15 (m, 3H).

Step B: Preparation of 4-(2,6-Dimethylbenzyloxy)-3-methoxyacetophenone:
Using the method of Example 35, Step B, the title compound was obtained.
$^1$H NMR (270 MHz, CDCl$_3$): 2.4 (s, 6H); 2.6 (s, 3H); 3.9 (s, 3H); 5.1 (s, 2H); 7.1 (d, 2H); 7.2 (m, 2H); 7.6 (m, 2H).

Step C: Preparation of Ethyl 4-[[4-(2,6-dimethylbenzyloxy)-3-methoxy]phenyl]-4-oxobutyrate:
Using the method of Example 17, Step. B, the title compound was obtained.
$^1$H NMR (270 MHz, CDCl$_3$): 1.2 (s, 3H); 2.4 (s, 6H); 2.8 (t, 2H); 3.3 (t, 2H); 3.9 (s, 3H); 4.4 (q, 2H); 5.1 (s, 2H); 7.0–7.2 (m, 4H); 7.6 (m, 2H).

Step D: Preparation of 4-[[4-(2,6-Dimethylbenzyloxy)-3-methoxy]phenyl]-4-oxobutyric acid:
Using the method of Example 36, Step E, the title compound was obtained.
$^1$H NMR (270 MHz, CDCl$_3$): 2.4 (s, 6H); 2.8 (t, 2H); 3.3 (t, 2H); 3.9 (s, 3H); 5.1 (s, 2H); 7.0–7.2 (m, 4H); 7.6 (m, 2H).

Example 47

Synthesis of 4-{3-[((4-Trifluoromethylbenzylamino)-carbonyl)-4-methoxy]phenyl}-4-oxobutyric acid

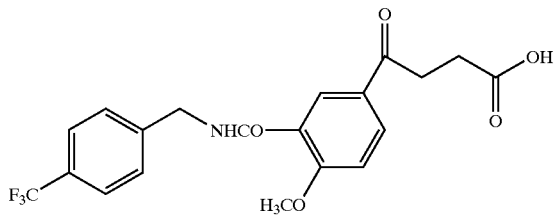

Step A: Preparation of Methyl 2-methoxy-5-acetylbenzoate:
To a stirred solution of Methyl 2-hydroxy-5-acetylbenzoate (12 g, 61.7 mmol) in DMF (200 ml) was added cesium carbonate (24.15 g, 74.1 mmol) and MeI (9.64 g, 68 mmol). The reaction mixture was stirred for 16 hours at 0° C. and then diluted with ethyl acetate, washed with aq Na$_2$S$_2$O$_5$, brine, dried over Na$_2$SO$_4$, filtered and concentrated. The purification was done by flash chromatography on silica gel column (ethyl acetate:hexane 1:2) to provide the title compound as an off white solid.
$^1$H NMR (270 MHz, DMSO): 2.6 (s, 3H); 3.8 (s, 3H); 3.9 (s, 3H); 7.3 (d, 1H); 8.1 (dd, 1H); 8.2 (s, 1H).

Step B: Preparation of 2-Methoxy-5-acetylbenzoic acid:
Methyl 2-methoxy-5-acetylbenzoate (Step A, 3 g, 14.4 mmol) was dissolved in acetic acid (80 ml) and then treated with c HCl (28 ml). The reaction mixture was refluxed for 4 hours, concentrated under reduced pressure and lyophilized to provide the title compound as cream color solid, which was used without further purification.
$^1$H NMR (270 MHz, DMSO): 2.6 (s, 3H); 3.9 (s, 3H); 7.3 (d, 1H); 8.1 (dd, 1H); 8.2 (s, 1H).

Step C: Preparation of 5-Acetyl-2-methoxy-N-[[4-(trifluoromethyl)phenyl]methyl]benzamide:
To a stirred solution of 2-Methoxy-5-acetylbenzoic acid (Step B, 2.5 g, 12.8 mmol), HOBt.H$_2$O (2.08 g, 15.4 mmol), and EDC (3.70 g, 19.3 mmol) in CH$_2$Cl$_2$ (20 ml) and DMF (5 ml) was added 4-(Trifluoromethyl)benzylamine (2.48 g, 14.1 mmol), and the mixture was stirred for 16 hours at room temperature. The reaction mixture was concentrated under reduced pressure and then redissolved in ethyl acetate. The organic layer was washed with 3% K$_2$CO$_3$, 1 N HCl, and brine, dried over Na$_2$SO$_4$, filtered and concentrated. The purification was done by flash chromatography on silica gel column (chloroform:methanol 95:5) to provide the title compound as white solid.
$^1$H NMR (270 MHz, CDCl$_3$): 2.6 (s, 3H); 4.0 (s, 3H); 4.8 (d, 2H); 7.0 (d, 1H); 7.5 (d, 2H); 7.6 (d, 2H); 8.1 (dd, 1H); 8.8 (s, 1H).

Step D: Preparation of Ethyl 4-{3-[((4-Trifluoromethylbenzylamino)-carbonyl)-4-methoxy]phenyl}-4-oxobutyrate:
Using the method of Example 17, Step B, the title compound was obtained.
$^1$H NMR (270 MHz, CDCl$_3$): 1.2 (s, 3H); 2.6 (t, 2H); 3.3 (t, 2H); 4.0 (s, 3H); 4.4 (q, 2H); 4.8 (s, 2H); 7.0 (d, 1H); 7.4 (d, 2H); 7.6 (d, 2H); 8.1 (dd, 1H); 8.8 (s, 1H).

Step E: Preparation of 4-{3-[((4-Trifluoromethylbenzylamino)-carbonyl)-4-methoxy]phenyl}-4-oxobutyric acid:
Using the method of Example 36, Step E, the title compound was obtained.
$^1$H NMR (270 MHz, CDCl$_3$: CD$_3$OD): 2.6 (t, 2H); 3.3 (t, 2H); 4.0 (s, 3H); 4.7 (s, 2H); 7.0 (d, 1H); 7.4 (d, 2H); 7.6 (d, 2H); 8.1 (dd, 1H); 8.8 (s, 1H).

Example 48

Synthesis of 4-{3-[((2,6-Dimethylbenzylamino)-carbonyl)-4-methoxy]phenyl}-4-oxobutyric acid

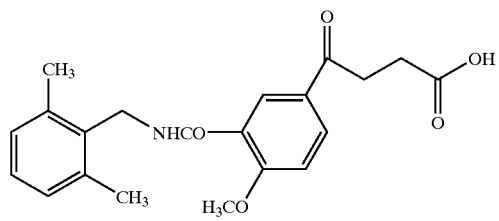

Step A: Preparation of 2,6-Dimethylbenzyl Alcohol:
Using the method of Example 35, Step A, the title compound was obtained.
$^1$H NMR (270 MHz, CDCl$_3$): 2.4 (s, 6H); 4.7 (s, 2H); 7.0–7.15 (m, 3H).

Step B: Preparation of N-(2,6-Dimethylbenzyl)phthalimide:
To a stirred solution of 2,6-Dimethylbenzyl Alcohol (Step A, 6.59 g, 48.4 mmol) in DMSO (20 ml) was added chlorotrimethylsilane (15.75 ml, 145 mmol) at room temperature, and the mixture was stirred for one hr. To this reaction mixture were added ethyl acetate and water, the organic layer was washed with brine, dried over Na₂SO₄, filtered and concentrated to give an oil. The oily residue was redissolved in DMF (100 ml) and potassium phthalimide (10.76 g, 58.1 mmol) was added. The reaction mixture was stirred for 16 hours at room temperature, ethyl acetate was added, and the organic layer was washed with 3% Na₂CO₃, 1 N HCl, dried over Na₂SO₄, filtered and concentrated to give white solid. The purification was done by flash chromatography on silica gel column (chloroform:methanol 95:5) to provide the title compound as white solid.

¹H NMR (270 MHz, DMSO): 2.3 (s, 6H); 4.8 (s, 2H); 7.0 (m, 3H); 7.8 (s, 4H).

Step C: Preparation of 2,6-Dimethylbenzyl Amine:

To a stirred solution of N-(2,6-Dimethylbenzyl) phthalimide (Step B, 7.77 g, 29.3 mmol) in ethanol (80 ml) was added hydrazine monohydrate (2.16 ml, 44.52 mmol) and the reaction mixture was refluxed for 3.5 hours. To this reaction mixture was added c HCl to bring pH to 1 and refluxing continued for another 3.5 hours, water was added and reaction mixture was filtered, the filtrate was concentrated and pH was adjusted to 10 with 2 N NaOH. The residue was taken in methylene chloride and washed with brine, dried over Na₂SO₄, filtered and concentrated to give an oil which was used without further purification.

¹H NMR (270 MHz, DMSO): 2.3 (s, 6H); 3.8 (s, 2H); 7.0 (m, 3H).

Step D: Preparation of 5-Acetyl-2-methoxy-N-[[2,6-dimethyl)phenyl]methyl]benzamide:

To a stirred solution of 2-Methoxy-5-acetylbenzoic acid (Example 47, Step B, 2.5 g, 12.8 mmol), HOBt (2.08 g, 15.4 mmol), and EDC (3.70 g, 19.3 mmol) in CH₂Cl₂ (20 ml) and DMF (5 ml) was added 2,6-Dimethylbenzyl amine (Step C, 1.72 g, 12.8 mmol), and the mixture was stirred for 16 hours at room temperature. The reaction mixture was concentrated under reduced pressure and then redissolved in ethyl acetate. The organic layer was washed with 3% K₂CO₃, 1 N HCl, and brine, dried over Na₂SO₄, filtered and concentrated. The purification was done by flash chromatography on silica gel column (chloroform:methanol 95:5) to provide the title compound as white solid.

¹H NMR (270 MHz, CDCl₃): 2.5 (s, 6H); 2.6 (s, 3H); 3.9 (s, 3H); 4.7 (s, 2H); 7.0 (d, 1H); 7.2 (m, 3H); 7.6 (br, 1H); 8.1 (dd, 1H); 8.8 (s, 1H).

Step E: Preparation of Ethyl 4-{3-[((2,6-Dimethylbenzylamino)-carbonyl)-4-methoxy]phenyl}-4-oxobutyrate:

Using the method of Example 17, Step B, the title compound was obtained.

¹H NMR (270 MHz, CDCl₃): 1.2 (t, 3H); 2.4 (s, 6H); 2.7 (t, 2H); 3.3 (t, 2H); 3.9 (s, 3H); 4.4 (q, 2H); 4.7 (s, 2H); 7.0 (m, 3H); 7.2 (m, 1H); 8.1 (dd, 1H); 8.7 (s, 1H).

Step F: Preparation of 4-{3-[((2,6-Dimethylbenzylamino)-carbonyl)-4-methoxy]phenyl}-4-oxobutyric acid:

Using the method of Example 36, Step E, the title compound was obtained.

¹H NMR (270 MHz, CDCl₃: CD₃OD): 2.4 (s, 6H); 2.7 (t, 2H); 3.3 (t, 2H); 3.9 (s, 3H); 4.7 (s, 2H); 7.0 (m, 3H); 7.2 (m, 1H); 8.1 (dd, 1H); 8.7 (s, 1H).

Example 49

Synthesis of 4-(3-(2,6-Dimethylbenzyloxy)phenyl)-4-oxobutanecarbohydroxamic acid:

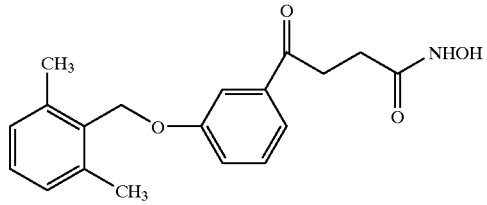

Step A: Preparation of 2,6-Dimethylbenzyl Alcohol:

Using the method of Example 35, Step A, the title compound was obtained.

¹H NMR (270 MHz, CDCl₃): 2.4 (s, 6H); 4.7 (s, 2H); 7.0–7.15 (m, 3H).

Step B: Preparation of 3-(2,6-Dimethylbenzyloxy) acetophenone:

Using the method of Example 35, Step B, the title compound was obtained.

¹H NMR (270 MHz, CDCl₃): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy) phenyl)-4-oxobutyrate:

Using the method of Example 17, Step B, the title compound was obtained.

¹H NMR (270 MHz, CDCl₃): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of 4-(3-(2,6-Dimethylbenzyloxy) phenyl)-4-oxobutanecarbohydroxamic acid:

To a hydroxylamine hydrochloride solution in dry ethanol, add a solution of potassium hydroxide in dry ethanol at 35° C. Cool the mix and add Ethyl 4-(3-(2,6-dimethylbenzyloxy)phenyl)-4-oxobutyrate (Step C), and powdered potassium hydroxide. After few hours, reaction mixture can be diluted with water and neutralize with hydrochloric acid, filter and recrystallize to give title compound.

Example 50

Synthesis of 4-(3-(2,6-Dimethylbenzyloxy)phenyl)-4-oxobutyramide

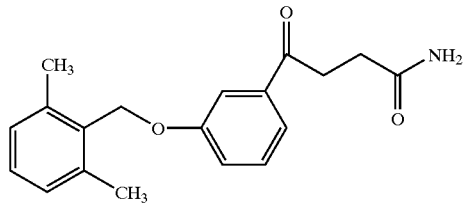

Step A: Preparation of 2,6-Dimethylbenzyl Alcohol:

Using the method of Example 35, Step A, the title compound was obtained.

¹H NMR (270 MHz, CDCl₃): 2.4 (s, 6H); 4.7 (s, 2H); 7.0–7.15 (m, 3H).

Step B: Preparation of 3-(2,6-Dimethylbenzyloxy) acetophenone:

Using the method of Example 35, Step B, the title compound was obtained.

¹H NMR (270 MHz, CDCl₃): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy)phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of 4-(3-(2,6-Dimethylbenzyloxy)phenyl)-4-oxobutyric acid:

Using the method of Example 35, Step D, the title compound was obtained.

$^1$H NMR (270 MHz, CDCl$_3$): 2.4 (s, 6H); 2.8 (t, 2H); 3.3 (t, 2H); 5.1 (s, 2H); 7.1 (d, 2H); 7.2–7.3 (m, 2H); 7.4 (t, 1H); 7.6 (m, 2H).

Step E: Preparation of 4-(3-(2,6-Dimethylbenzyloxy)phenyl)-4-oxobutyramide:

To a solution of 4-(3-(2,6-Dimethylbenzyloxy)phenyl)-4-oxobutyric acid (Step D) in DMF, add triethylamine and BOP, after couple of hours of stirring, reaction mixture can be added to liquid ammonia at −40° C. and the resulting mixture can be warmed for 16 hours to give title compound.

Example 51

Synthesis of 4-(3-(2,6-Dimethylbenzyloxy)phenyl)-4-oxo-2-butenoic acid

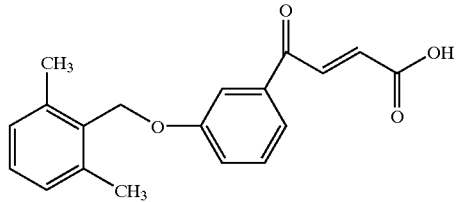

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 3-(2,6-Dimethylbenzyloxy)acetophenone:

Using the method of Example 35, Step B, the title compound was obtained.

$^1$H NMR (270 MHz, CDCl$_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy)phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of Ethyl 4-(3-(2,6-dimethylbenzyloxy)phenyl)-4-oxo-3-bromo-butyrate:

To a ice cooled solution of Ethyl 4-(3-(2,6-dimethylbenzyloxy)phenyl)-4-oxobutyrate (Step C, 3 g, 9 mmol) in dry ether (70 ml) was added dropwise bromine (0.7971 g, 9.9 mmol) diluted in ether (30 ml). After 4 hours of stirring, reaction mixture was concentrated and purified by flash chromatography on silica gel column (EtOAc:Hex, 1:4) to provide the title compound.

$^1$H NMR (270 MHz, CDCl$_3$): 1.2 (s, 3H); 2.4 (s, 6H); 3.1 (m, 1H); 3.5 (m, 1H); 4.2 (q, 2H); 5.1 (s, 2H); 5.5 (m, 1H); 7.1 (d, 2H); 7.2 (m, 2H); 7.4 (t, 1H); 7.6 (m, 2H).

Step E: Preparation of Ethyl 4-(3-(2,6-dimethylbenzyloxy)phenyl)-4-oxo-2-butenoate:

Triethylamine (5.95 g, 58.9 mmol) was added to a solution of Ethyl 4-(3-(2,6-dimethylbenzyloxy)phenyl)-4-oxo-3-bromo-butyrate (Step D, 2.47 g, 5.8 mmol) in carbon tetrachloride (50 ml). After stirring for 4 hours at room temperature, the reaction mixture was filtered through a pad of silica gel few times, and concentrated to give the title compound.

$^1$H NMR (270 MHz, CDCl$_3$): 1.2 (s, 3H); 2.4 (s, 6H); 4.2 (q, 2H); 5.1 (s, 2H); 6.9 (dd, 1H); 7.1 (d, 2H); 7.2 (m, 2H); 7.4 (t, 1H); 7.6 (m, 2H); 7.9 (dd, 1H).

Step F: Preparation of 4-(3-(2,6-Dimethylbenzyloxy)phenyl)-4-oxo-2-butenoic acid:

To a solution of Ethyl 4-(3-(2,6-dimethylbenzyloxy)phenyl)-4-oxo-2-butenoate (Step E) in abs ethanol at low temp, add aqueous sodium hydroxide, after an hour, concentrate and purify by flash chromatography on silica gel column (chloroform:methanol 95:5 spiked with acetic acid).

Example 52

Synthesis of 4-(3-(2,6-Dimethylbenzyloxy)phenyl)-3-butenoic acid

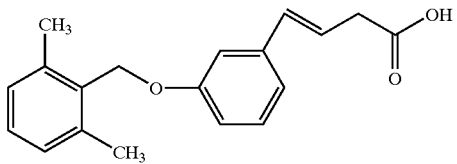

Step A: Preparation of 2,6-Dimethylbenzyl Alcohol:

Using the method of Example 35, Step A, the title compound was obtained.

$^1$H NMR (270 MHz, CDCl$_3$): 2.4 (s, 6H); 4.7 (s, 2H); 7.0–7.15 (m, 3H).

Step B: Preparation of 3-(2,6-Dimethylbenzyloxy)acetophenone:

Using the method of Example 35, Step B, the title compound was obtained.

$^1$H NMR (270 MHz, CDCl$_3$): 2.4 (s, 6H); 2.6 (s, 3H); 5.1 (s, 2H); 7.1 (dd, 2H); 7.2 (m, 2H); 7.4 (t, 1H); 7.6 (m, 2H).

Step C: Preparation of Ethyl 4-(3-(2,6-dimethylbenzyloxy)phenyl)-4-oxobutyrate:

Using the method of Example 17, Step B, the title compound was obtained.

$^1$H NMR (270 MHz, CDCl$_3$): 1.2 (s, 3H); 2.4 (s, 6H); 2.8 (t, 2H); 3.2 (t, 2H); 4.4 (q, 2H); 5.1 (s, 2H); 7.1 (d, 2H); 7.2 (m, 2H); 7.4 (t, 1H); 7.6 (m, 2H).

Step D: Preparation of Ethyl 4-(3-(2,6-dimethylbenzyloxy)phenyl)-4-hydroxy-butyrate:

To a solution of Ethyl 4-(3-(2,6-dimethylbenzyloxy)phenyl)-4-oxobutyrate (Step C) in tetrahydrofuran, add sodium borohydride dissolved in water, After 3–4 hours of stirring at room temperature, quench with an acid. The organic layer can be taken in dichloromethane, wash with water, aqueous sodium bicarbonate, and brine, dry over Na$_2$SO$_4$, filter and concentrate. If needed, the compound can be purified by flash chromatography on silica gel column (EtOAc:Hex).

Step E: Preparation of Ethyl 4-(3-(2,6-dimethylbenzyloxy)phenyl)-4-bromo-butyrate:

To a solution of Ethyl 4-(3-(2,6-dimethylbenzyloxy)phenyl)-4-hydroxy-butyrate (Step D) in dioxane, add phosphorous tribromide in dioxane dropwise. After stirring at room temperature for 16 hours, quench with water and chloroform. After few minutes, the reaction mixture can be neutralized by mild aqueous base, dry organic layer over $Na_2SO_4$, filter, concentrate and purify by flash chromatography on silica gel column (EtOAc:hex).

Step F: Preparation of Ethyl 4-(3-(2,6-dimethylbenzyloxy) phenyl)-3-butenoate:

Add Triethylamine to a solution of Ethyl 4-(3-(2,6-dimethylbenzyloxy)phenyl)-4-bromo-butyrate (Step E) in carbon tetrachloride. After stirring approximately for 4 hours, the mixture can be filtered through a pad of silica gel few times, and concentrate to give the title compound.

Step G: Preparation of 4-(3-(2,6-Dimethylbenzyloxy) phenyl)-3-butenoic acid:

To a solution of Ethyl 4-(3-(2,6-dimethylbenzyloxy) phenyl)-3-butenoate (Step F) in abs ethanol at low temp, add aqueous sodium hydroxide, after an hour, concentrate and purify by flash chromatography on silica gel column (chloroform:methanol 95:5 spiked with acetic acid).

BIOLOGICAL ACTIVITY EXAMPLES

Example A

Compound AH Improves Metabolic Abnormalities in Insulin-dependent Diabetes

Streptozotocin (STZ) is a toxin that selectively destroys insulin-producing pancreatic beta cells, and is widely used to induce insulin-dependent diabetes in experimental animals.

Female Balb/C mice (8 weeks old; 18–20 grams body weight) were treated with streptozotocin (STZ) (50 mg/kg i.p. on each of five consecutive days). Fourteen days after the last dose of STZ, blood glucose was measured to verify that the animals were diabetic, and the mice were divided into two groups of 5 animals each, one group receiving Compound AH (250 mg/kg) daily by oral gavage, and the other receiving vehicle (0.75% hydroxypropylmethylcellulose, a suspending agent, in water). A group of nondiabetic mice from the same cohort that did not receive STZ were also monitored. Blood samples were taken periodically for determination of blood glucose concentrations, and body weights were also recorded.

After several weeks of treatment, blood glucose concentrations in mice treated with oral Compound AH began to decrease toward baseline, whereas blood glucose in the vehicle-treated control animals continued to rise. Body weights and blood glucose, triglyceride and cholesterol concentrations 14 weeks after the beginning of drug treatment are shown in Table 1.

TABLE 1

Serum chemistries and body weights in streptozotocin diabetic mice treated with oral Compound AH for 14 weeks

| Group | Glucose mg/dL | Triglycerides mg/dL | Cholesterol mg/dL | Body Weight (g) |
| --- | --- | --- | --- | --- |
| Nondiabetic + Vehicle | 138 ± 6 | 88 ± 9 | 88 ± 6 | 21 + 0.6 |
| Diabetic + Vehicle | 615 ± 46 | 154 ± 16 | 133 ± 6 | 17.5 + 1.0 |
| Diabetic + Compound AH | 207 ± 12 | 62 ± 7* | 82 ± 2* | 21.7 + 0.8* |

*significantly different from STZ Diabetic group, P < .001

Oral Compound AH treatment resulted in significant amelioration of metabolic abnormalities associated with insulin-dependent diabetes.

Example B

Oral Compound AH Improves Survival of Mice with Lethal Insulin-dependent Diabetes Female Balb/C mice (14 weeks old) were treated with a single dose of streptozotocin (175 mg/kg i.p.) to induce severe insulin-dependent diabetes. Seven days later, mice were divided into three treatment groups: Compound AH, pioglitazone, and vehicle. Mice were treated daily via oral gavage, and survival was monitored over time.

TABLE 2

| Groups | Survival at 12 weeks Survivors |
| --- | --- |
| Vehicle | 0/5 |
| Pioglitazone 30 mg/kg/day | 2/5 |
| Compound AH 250 mg/kg/day | 4/5 |

All of the diabetic animals treated with oral vehicle died of severe, uncontrolled diabetes. Two of five animals treated with pioglitazone, an antidiabetic insulin sensitizer used to treat humans with noninsulin-dependent diabetes, were alive at 12 weeks, but had lost 15–20% of their body weight. Four of the five animals treated with oral Compound AH were alive at 12 weeks, and their body weights recovered and were maintained in the normal range.

Example C

Oral Compound AA Reduces Mortality in Severe Insulin-dependent Diabetes

Female balb/C mice (19 wks of age at start of experiment) were challenged with multiple high doses of STZ (75 mg/kg i.p. on 5 consecutive days). Animals were then divided in two groups (20 mice/group) matched for severity of diabetes. Four days after the last dose of STZ, treatments were initiated. One group received Vehicle (0.4 ml of 0.75% HPMC, p.o.), and the other group received oral COMPOUND AA (30 mg/kg/day). After three weeks of daily treatment, cumulative mortality in the Vehicle Control group was 19/20 mice. In contrast, only 5/20 of the COMPOUND AA mice died during this time.

Example D

Compound AH Reduces the Incidence of Spontaneous Diabetes and Mortality in NOD Mice A substantial proportion of NOD ("non-obese diabetic") mice develop insulin-dependent diabetes as a consequence of spontaneous autoimmune destruction of pancreatic islet cells.

Two groups of 20 NOD mice (6 weeks old) were treated daily with either oral Vehicle (0.4 ml of 0.75% hydroxypropyl methylcellulose in water; HPMC) or Compound AH (200 mg/kg/day) suspended in HPMC. The incidence of mortality due to spontaneous development of severe insulin-dependent diabetes was monitored over a period of seven months. At the end of this time, 13/20 mice treated with vehicle had died of uncontrolled diabetes, whereas only 5/20 mice treated with Compound AH had died.

Example E

Compound AW Reduces Hyperglycemia and Hyperlipidemia, and Ameliorates Fatty Liver Disease in Ob/ob Obese Diabetic Mice Ob/ob mice have a defect in the gene for leptin, a protein involved in appetite regulation and energy metabolism, and are hyperphagic, obese, and insulin resistant. They develop hyperglycemia and fatty liver.

Male lean (ob/+ heterozygote) and obese (ob/ob homozygote) C57BL/6 mice approximately 8 weeks of age were obtained from Jackson Labs (Bar Harbor, Me.) and randomly assigned into groups of 5 animals such that body weights and blood glucose concentrations were similar between groups. All animals were maintained under the control of temperature (23 C), relative humidity (50±5%) and light (7:00–19:00), and allowed free access to water and laboratory chow (Formulab Diet 5008, Quality Lab Products, Elkridge, Md.). Blood glucose was routinely determined with glucose test strips and a Glucometer Elite XL device (Bayer Corporation). At selected time points, blood samples (~1100 microliters) were obtained with a heparinized capillary tube via the retro-orbital sinus for serum chemistry analysis. Serum chemistry (glucose, triglycerides, cholesterol, BUN, creatinine, AST, ALT, SDH, CPK and free fatty acids) analyses were performed on a Hitachi 717 Analyzer, and plasma insulin and pancreatic insulin were measured by an electrochemiluminescent immunoassay (Origen Analyzer, Igen, Inc., Gaithersburg, Md.).

Groups of ob/ob mice were divided into treatment cohorts as indicated below, and given daily oral doses of Compound AW (10, 30, 100, 150 or 300 mg), rosiglitazone (1, 3, 10 or 30 mg), or pioglitazone (30 or 100 mg). The latter two compounds are insulin-sensitizing drugs used in the treatment of human patients with non-insulin dependent diabetes mellitus, and are used as comparators for efficacy and safety of compounds of the invention. The dose ranges of compounds in this experiment were chosen to include both suboptimal and potentially supraoptimal doses.

Compound AW produced reduction in blood glucose comparable to that achieved with pioglitazone and rosiglitazone, as shown in Table 3. At doses of 100 to 300 mg/kg/day, Compound AW reduced serum triglycerides and fatty acids better than did either rosiglitazone or pioglitazone at their optimum antihyperglycemic doses.

TABLE 3

Effect of Compound AW, pioglitazone (PG) and rosiglitazone (RSG) on serum glucose, triglycerides, and free fatty acids in ob/ob mice

| Group | Glucose ± SEM mg/dL | Triglycerides ± SEM mg/dL | Free Fatty Acids ± SEM micromoles/L |
|---|---|---|---|
| ob/+ | 268.6 ± 12.9 | 111.6 ± 12.0 | 2216 ± 197.4 |
| ob/ob | 384.2 ± 53.8 | 106.6 ± 2.909 | 3399 ± 345.6 |
| AW-10 | 369.6 ± 62.5 | 115.6 ± 7.8 | 3697.4 ± 357.8 |
| AW-30 | 280.2 ± 46.7 | 96.4 ± 7.3 | 2552.2 ± 334.7 |
| AW-100 | 286 ± 47.1 | 66.2 ± 5.9 | 1476 ± 82.1 |
| AW-150 | 188.6 ± 28.8 | 72.6 ± 5.6 | 1481 ± 158.8 |
| AW-300 | 128.4 ± 8.8 | 63.6 ± 3.4 | 1452.6 ± 111.1 |
| PG-30 | 188.2 ± 21.4 | 111.2 ± 7.5 | 2606 ± 139.2 |
| PG-100 | 174.6 ± 11.5 | 95.2 ± 4.8 | 1983.4 ± 66.1 |
| RSG-1 | 142.75 ± 8.8 | 109.75 ± 4.4 | 2090.75 ± 67.7 |
| RSG-3 | 190.2 ± 12.7 | 107.8 ± 3.8 | 2317.6 ± 85.3 |
| RSG-10 | 188.2 ± 21.4 | 111.2 ± 7.5 | 2606.4 ± 139.2 |
| RSG-30 | 174.6 ± 11.5 | 95.2 ± 4.8 | 1983.4 ± 66.1 |

Ob/ob mice develop chronic inflammatory fatty liver disease and are considered to be an animal model for nonalcoholic steatohepatitis (NASH), a condition which can lead toward progressive cirrhosis and liver dysfunction. In NASH, fat accumulation increases the susceptibility of the liver to inflammatory injury. One characeristic sign of NASH in patients is, in the absence of viral infection or alcoholism, elevated levels in serum of enzymes that are released from damaged hepatocytes, e.g. alanine aminotransferase (ALT), aspartate aminotransferase (AST), and sorbitol dehydrogenase (SDH). These enzymes are elevated in ob/ob mice as a consequence of fatty liver and secondary inflammation. In Table 4, ALT, AST, and SDH in serum samples from mice treated with Compound AW, pioglitazone, and rosiglitazone are shown, as are enzyme levels in serum from normal lean mice and from diabetic control mice treated only with vehicle. ALT, AST and SDH are significantly elevated in obese diabetic ob/ob mice compared to lean mice. Compound AW treatment at doses ranging from 30 mg/kg/day to 300 mg/kg/day resulted in a dose-dependent decrease in serum liver enzymes. In contrast, pioglitazone (30 and 100 mg/kg/day) and rosiglitazone (1 to 30 mg/kg/day) induced an elevation in ALT and AST and did not change SDH. The serum liver enzyme profiles correlated with liver histology. Vehicle-treated ob/ob obese diabetic mice had marked fat accumulation in the liver in discrete intracellular droplets. Daily Compound AW treatment for 4 weeks caused a marked reduction in liver fat droplets, whereas neither pioglitazone nor rosiglitazone reduced the size or density of fat droplets in the hepatocytes.

TABLE 4

Effect of Compound AW, pioglitazone and rosiglitazone on serum enzyme indicators of liver injury

| Group | ALT (U/L) ± SEM | AST (U/L) ± SEM | SDH (U/L) ± SEM |
|---|---|---|---|
| Lean | 106.4 ± 16.3 | 25.6 ± 2.7 | 23.2 ± 4.5 |
| Diabetic | 447.2 ± 63.4 | 645.6 ± 104.8 | 745.8 ± 102.4 |
| 2022-10 | 483.8 ± 81.9 | 653.4 ± 104.8 | 626.8 ± 93.8 |
| AW-30 | 320.2 ± 46.2 | 399.6 ± 74.4 | 333.0 ± 66.9 |
| AW-100 | 202.8 ± 38.0 | 143.8 ± 30.4 | 121.2 ± 14.1 |
| AW-150 | 149.2 ± 15.6 | 185.8 ± 26.0 | 166.2 ± 20.0 |
| AW-300 | 188.2 ± 10.3 | 335.4 ± 44.8 | 207.0 ± 29.3 |
| PG-30 | 713.6 ± 80.6 | 1024 ± 88.7 | 782.0 ± 70.6 |
| PG-100 | 646.0 ± 56.1 | 901.0 ± 49.3 | 603.0 ± 27.3 |
| RSG-1 | 668.8 ± 42.9 | 798.0 ± 73.8 | 644.5 ± 51.6 |
| RSG-3 | 716.6 ± 56.6 | 853.8 ± 43.8 | 615.4 ± 38.6 |
| RSG-10 | 713.6 ± 80.5 | 1024.0 ± 88.7 | 782.0 ± 70.6 |
| RSG-30 | 646.0 ± 56.1 | 901.2 ± 49.3 | 603.0 ± 27.3 |

The ob/ob Mice gained body weight during the four week treatment period. As is shown in Table 5, pioglitazone and rosiglitazone exacerbated weight gain relative to vehicle-treated mice; whereas Compound AW induced a dose-dependent attenuation of weight gain.

TABLE 5

Effect of Compound AW, Pioglitazone and Rosiglitazone on body weight gain of ob/ob mice

| Groups | Mean body weight gain (grams) |
|---|---|
| HPMC (Vehicle) | +7.4 |
| AW-3 mg/kg/day | +7.3 |
| AW-10 mg/kg/day | +6.7 |
| AW-30 mg/kg/day | +6.4 |
| AW-100 mg/kg/day | +3.4 |
| AW-150 mg/kg/day | +4.6 |
| AW-300 mg/kg/day | −0.7 |
| PG-30 mg/kg/day | +10.0 |
| PG-100 mg/kg/day | +13.6 |
| RSG-1 mg/kg/day | +8.2 |
| RSG-3 mg/kg/day | +8.5 |
| RSG-10 mg/kg/day | +11.0 |
| RSG-30 mg/kg/day | +12.0 |

Example F

Acute Hypoglycemic Effects of Compounds of the Invention in Diabetic Mice: Experiment 1

Compounds of the invention display acute antihyperglycemic activity in animals with non insulin-dependent diabetes.

Male ob/ob diabetic mice were randomized into groups of five animals each. Body weights were 50–55 g and blood glucose was approximately 300 mg/dL in the fed state. A single oral dose of a test substance suspended in 0.5% carboxymethylcellulose vehicle was administered by gavage. Blood glucose was measured in blood droplets obtained by nicking a tail vein with a razor using glucometer test strips and a Glucometer Elite XL device (Bayer) at 0, 0.5, 2, 4, 6 and 18 hours after the initial dosing. A 10% reduction in blood glucose versus oral vehicle is considered a positive screening result. Blood glucose reductions were generally maximal at 6 hours after drug administration.

TABLE 6

Acute hypoglycemic effect of compounds of the invention in ob/ob obese diabetic mice

| Treatment Group | Blood Glucose After 6 hours | % Reduction vs Control |
|---|---|---|
| Vehicle | 297 ± 35 | 0.0 ± 11.8 |
| Compound AA | 242 ± 25 | −18.5 ± 8.4 |
| Compound AB | 181 ± 19 | −39.1 ± 6.4 |
| Compound AF | 314 ± 32 | −24.6 ± 7.7 * |
| Compound AG | 222 ± 23 | −25.3 ± 7.7 |
| Compound AH | 223 ± 11 | −24.9 ± 3.7 |
| Compound AI | 255 ± 9 | −14.1 ± 3.0 |
| Compound AJ | 190 ± 14 | −36.0 ± 4.7 |
| Compound AK | 210 ± 10 | −29.3 ± 3.4 |
| Compound AL | 168 ± 13 | −43.4 ± 4.4 |

* Initial blood glucose in this group was 416 ± 29 mg/dL and the 6 hour reading is normalized to that initial value. In all other groups in this experiment, mean initial blood glucose was ≦300 mg/dL.

Example G

Acute Hypoglycemic Effects of Compounds of the Invention in Diabetic Mice: Expt 2

Compounds of the invention display acute antihyperglycemic activity in animals with noninsulin-dependent diabetes.

Male ob/ob mice (50–55 grams; blood glucose ~300 mg/dL) were divided into groups of five animals each, and given a single oral dose of test drug (250 mg/kg) suspended in 0.5% carboxymethylcellulose vehicle; a control group received oral vehicle alone.

Six hours after oral administration of test drugs or vehicle (control), blood samples were obtained from a tail vein and glucose content was determined with a glucometer.

TABLE 7

Acute hypoglycemic effect of compounds of the invention in ob/ob obese diabetic mice

| Treatment Group | Blood Glucose after 6 hours 305 ± 20 mg/dL | % Reduction vs Control |
|---|---|---|
| Vehicle Control | | 0.0 ± 5.0 |
| Compound AN | 152 ± 11 | −50.2 ± 4.5% |
| Compound AQ | 220 ± 17 | −27.9 ± 4.2% |
| Compound AR | 179 ± 14 | −41.3 ± 4.2% |
| Compound AS | 167 ± 28 | −45.2 ± 2.0% |
| Compound AT | 198 ± 28 | −35.1 ± 2.3% |
| Compound AU | 224 ± 26 | −26.6 ± 2.8% |
| Compound AV | 207 ± 23 | −32.1 ± 3.0% |
| Compound AW | 143 ± 15 | −53.1 ± 3.1% |
| Compound AX | 165 ± 23 | −45.9 ± 2.4% |
| Compound AY | 185 ± 21 | −39.3 ± 2.9% |
| Compound AZ | 186 ± 10 | −39.0 ± 6.1% |

Oral treatment with compounds of the invention elicits an acute antihyperglycemic effect in obese diabetic mice.

Example H

Antidiabetic Effects of Compounds of the Invention in Db/db Mice

Db/db mice have a defect in leptin signaling, leading to hyperphagia, obesity and diabetes. Moreover, unlike ob/ob mice which have relatively robust islets, their insulin-producing pancreatic islet cells undergo failure during chronic hyperglycemia, so that they transition from hyperinsulinemia (associated with peripheral insulin resistance) to hypoinsulinemic diabetes.

Male db/db mice were given daily oral treatments with vehicle (0.75% hydroxypropylmethylcellulose) or antidiabetic compounds as indicated below. Blood samples were obtained via the retro-orbital sinus for serum chemistry analysis, or via the tail vein for glucose measurement with a test strip and glucometer.

After four weeks of daily oral dosing, Compound AW and Compound BH elicited a significant reduction in blood glucose. While pioglitazone did initially reduce blood glucose over the first 3 weeks, its activity had largely failed at the 4 week time point and thereafter. The dose of pioglitazone used in this experiment was reported in the literature to be a maximally-effective dose for treatment of db/db mice (Shimaya et al. (2000), *Metabolism* 49:411–7).

TABLE 8

| Groups | Glucose mg/dL | Glucose (% of Control) |
|---|---|---|
| Vehicle (Control) | 562 ± 24 | 100 ± 4 |
| Compound AW - 150 mg/kg | 313 ± 34 * | 56 ± 6 * |
| Compound BH - 150 mg/kg | 229 ± 49 * | 41 ± 9 * |
| Pioglitazone - 100 mg/kg | 558 ± 28 | 99 ± 5 |

* Less than Vehicle Control value, $p < .05$

In a second experiment in db/db mice, antidiabetic activity of Compound BI was compared with that of rosiglitazone. After 8 weeks of treatment, blood glucose and triglycerides were significantly lower in animals treated with either Compound BI or rosiglitazone, compared to vehicle-treated controls. The rosiglitazone dose used in this study was reported in published literature as the optimum dose for late stage db/db mice (Lenhard et al., (1999) *Diabetologia* 42:545–54). Groups consisted of 6–8 mice each.

TABLE 9

| Groups | Glucose (mg/dL) | Triglycerides (mg/dL) |
|---|---|---|
| Vehicle (Control) | 686 ± 47 | 147 ± 13 |
| Rosiglitazone-20 mg/kg | 343 ± 38 * | 89 ± 16 * |
| Compound BI-150 mg/kg | 254 ± 30 * | 99 ± 8 * |

* = Less than Vehicle Control value, P < .05 (One-way ANOVA)

Example I

Antidiabetic Effects of Compounds of the Invention in Db/db Mice

Db/db mice have a defect in leptin signaling, leading to hyperphagia, obesity and diabetes. Moreover, unlike ob/ob mice on a C57BL/6J background, db/db mice on a C57BL/KS background undergo failure of their insulin-producing pancreatic islet β cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and randomly assigned into groups of 5–7 animals such that the body weights (50–55 g) and serum glucose levels ($\geq$300 mg/dl in fed state) were similar between groups; male lean (db/+ heterozygote) mice served as cohort controls. A minimum of 7 days was allowed for adaptation after arrival. All animals were maintained under controlled temperature (23° C.), relative humidity (50±5%) and light (7:00–19:00), and allowed free access to standard chow (Formulab Diet 5008, Quality Lab Products, Elkridge, Md.) and water.

Treatment cohorts were given daily oral doses of (1% hydroxypropylmethylcellulose), Compounds BI, BO, BP, BQ or BR for 2 weeks. At the end of the treatment period 100 μl of venous blood was withdrawn in a heparinized capillary tube from the retro-orbital sinus of db/db mice for serum chemistry analysis.

Effects of compounds of the invention on nonfasting blood glucose are shown in Table 10; effects on serum triglycerides and free fatty acids are shown in Table 11.

TABLE 10

The effects of Compounds BI, BO, BP, BQ or BR on blood glucose in the db/db mouse model

| Groups | Glucose mg/dL | Glucose (% of Control) |
|---|---|---|
| Vehicle (Control) | 632 ± 19 | 100 ± 3 |
| BI-150 mg/kg | 279 ± 35 * | 44 ± 6 * |
| BI-100 mg/kg | 423 ± 53 * | 67 ± 8 * |
| BO-100 mg/kg | 586 ± 58 | 93 ± 9 |
| BP-100 mg/kg | 629 ± 86 | 99 ± 14 |
| BQ-100 mg/kg | 473 ± 49 * | 75 ± 7 * |
| BR-82 mg/kg | 703 ± 64 | 111 ± 10 |

Blood glucose levels in lean, nondiabetic db/+ heterozygote mice were 225 ± 15 mg/dL

TABLE 11

Effect of Compounds BI, BO, BP, BQ or BR on serum glucose, triglycerides, and free fatty acids in db/db mice

| Group | Triglycerides ± SEM (mg/dL) | Free Fatty Acids ± SEM (μM) |
|---|---|---|
| Lean | 142.4 ± 6.3 | 2577.6 ± 80.8 |
| Diabetic | 444.3 ± 57.3 | 4044.9 ± 158.5 |
| BI-150 | 103.6 ± 8.3 | 2234.0 ± 162.6 |
| BI-100 | 134.0 ± 13.1 | 2999.9 ± 98.7 |
| BO-100 | 261.1 ± 24.3 | 3766.3 ± 234.5 |
| BP-100 | 302.1 ± 28.1 | 3772.6 ± 182.5 |
| BQ-100 | 131.6 ± 20.7 | 2825.9 ± 110.9 |
| BR-82 | 253.0 ± 32.0 | 3653.4 ± 207.5 |

Example J

Antidiabetic Effects of Compounds of the Invention in Db/db Mice

Db/db mice have a defect in leptin signaling, leading to hyperphagia, obesity and diabetes. Moreover, unlike ob/ob mice on a C57BL/6J background, db/db mice on a C57BL/KS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and randomly assigned into groups of 5–7 animals such that the body weights (50–55 g) and serum glucose levels ($\geq$300 mg/dl in fed state) were similar between groups; male lean (db/+ heterozygote) mice served as cohort controls. A minimum of 7 days was allowed for adaptation after arrival. All animals were maintained under controlled temperature (23° C.), relative humidity (50±5%) and light (7:00–19:00), and allowed free access to standard chow (Formulab Diet 5008, Quality Lab Products, Elkridge, Md.) and water.

Treatment cohorts were given daily oral doses of Vehicle (1% hydroxypropylmethylcellulose), Compounds BI, BS, BT, BU, BV or Fenofibrate for 2 weeks. At the end of the treatment period 100 μl of venous blood was withdrawn in a heparinized capillary tube from the retro-orbital sinus of db/db mice for serum chemistry analysis.

Effects of compounds of the invention on nonfasting blood glucose are shown in Table 12; effects on serum triglycerides and free fatty acids are shown in Table 13.

TABLE 12

The effects of compounds BI, BS, BT, BU, BV and fenofibrate in db/db mice

| Groups | Glucose mg/dL | Glucose (% of Control) |
|---|---|---|
| Vehicle (Control) | 692.5 ± 55.4 | 100 ± 8 |
| BI - 100 mg/kg | 347.0 ± 43.1* | 50 ± 6* |
| BS - 93 mg/kg | 372.0 ± 53.8* | 54 ± 8* |
| BT - 107 mg/kg | 684.3 ± 63.6 | 99 ± 9 |
| BU - 128 mg/kg | 533.3 ± 46.7 | 77 ± 7 |
| BV - 115 mg/kg | 789.5 ± 38.9 | 114 ± 6 |
| Fenofibrate - 113 mg/kg | 563.2 ± 49.0 | 81 ± 7 |

Blood glucose levels in lean, nondiabetic db/+ heterozygote mice were 208.5 ± 6.6 mg/dL

TABLE 13

Effect of compounds BI, BS, BT, BU, BV and Fenofibrate on serum triglycerides and free fatty acids in db/db mice

| Group | Triglycerides ± SEM (mg/dL) | Free Fatty Acids ± SEM (µM) |
|---|---|---|
| Lean | 114.2 ± 8.7 | 2315.8 ± 238.3 |
| Vehicle | 232.8 ± 20.7 | 3511.8 ± 257.6 |
| BI | 77.8 ± 5.3 | 1997.2 ± 196.4 |
| BS | 132.0 ± 15.2 | 2867.4 ± 267.7 |
| BT | 211.5 ± 21.5 | 3897.7 ± 291.3 |
| BU | 172.5 ± 9.9 | 3587.0 ± 156.3 |
| BV | 153.2 ± 14.2 | 3373.8 ± 233.6 |
| Fenofibrate | 109.3 ± 9.1 | 3318.5 ± 208.7 |

Example K

Attenuation of Cataractogenesis of Compounds of the Invention in Zucker Diabetic Fatty (ZDF) Rats Cataracts are one of the leading causes of progressive vision decline and blindness associated with ageing and diabetes, and the Zucker diabetic fatty (ZDF) model has many similarities with human cataractogenesis, including biochemical changes and oxidative stress in the lens. These rats, however, undergo cataractogenesis typically between 14–16 weeks of age.

Male ZDF rats and their aged-match Zucker lean (ZL) counterparts (fa/+ or +/+) were obtained from Genetic Models, Inc. (Indianapolis, Ind.) aged 12 weeks and acclimatized for 1 week prior to study. All animals were maintained under controlled temperature (23° C.), relative humidity (50±5%) and light (7:00–19:00), and allowed free access to standard chow (Formulab Diet 5008; Quality Lab Products, Elkridge, Md.) and tap water ad libitum. Treatment cohorts were given a daily oral dose of vehicle and 100 mg/kg of BI or BH for 10 weeks. Body weights and blood glucose were routinely determined (once a week, usually around 10:00 A.M.) from tail bleeds with glucose test strips and a Glucometer Elite XL device (Bayer Corporation). At the end of the treatment period 100 µl of venous blood was collected (usually 10:00 A.M.) in a heparinized tube from the tail vein for serum chemistry analysis (Anilytics, Inc., Gaithersburg, Md.). Serum chemistry (glucose (GL), triglycerides (TG), aspartate aminotransferase (AST), alanine aminotransferase (ALT), sorbitol dehydrogenase (SDH), and free fatty acids (FFA)) analyses were performed on a Hitachi 717 Analyzer (Anilytics, Inc., Gaithersburg, Md.). Plasma insulin was measured by an electrochemiluminescent immunoassay, ECL (Origen Analyzer, Igen, Inc., Gaithersburg, Md.). The animals were sacrificed and tissues and/or organs (lens and liver) were extirpated, weighed (wet weight) and processed for biochemical analyses. Malondialdehyde (MDA), a major product of lipid peroxidation was assayed in lenses according to Ohkawa et al (1979), Analytical Biochem 95, 351–358).

Table 14 shows the incidence of visible cataracts in the eyes of the ZDF rats. Table 15 indicates additional quantitative indices of cataractogenesis in the same animals.

TABLE 14

Attenuation of cataractogenesis by Compounds BH and BI in ZDF rats.

| Animal Groups | N | Cataract Formation | | % Protection | |
|---|---|---|---|---|---|
| | | Left Eye | Right Eye | Left Eye | Right Eye |
| Vehicle-Control | 6 | 6/6 | 6/6 | 0 | 0 |
| BI | 6 | 3/6 | 1/6 | 50 | 83 |
| BH | 6 | 4/6 | 5/6 | 33 | 17 |
| Lean | 4 | 0/4 | 0/4 | N/A | N/A |

TABLE 15

Attenuation of cataractogenesis by BH and BI in ZDF rats.

| Groups | Weight (mg) | | Size (mm) | | Lenticular MDA nmol/g lens |
|---|---|---|---|---|---|
| | Left Lens | Right Lens | Left Lens | Right Lens | |
| LEAN | 51.2 ± 3.5 | 59.0 ± 0.4 | 3.8 ± 0.2 | 3.9 ± 0.1 | 0.4 ± 0.0 |
| Vehicle | 15.1 ± 1.4 | 16.8 ± 1.7 | 1.9 ± 0.1 | 2.0 ± 0.2 | 2.4 ± 0.2 |
| BI | 38.1 ± 7.3** | 54.9 ± 1.2* | 3.4 ± 0.2* | 3.8 ± 0.1* | 0.8 ± 0.1‡ |
| BH | 27.0 ± 7.2 | 20.0 ± 6.6 | 2.5 ± 0.3 | 2.1 ± 0.4 | 1.9 ± 0.2 |

Data are means ± SEM. *p < 0.05 compared with the vehicle-controls (diabetic) and Compound BH-treated groups, respectively; **p < 0.05 compared with vehicle-controls; ‡p < 0.05 compared with vehicle-controls and Compound BH right lenses, respectively (One Way ANOVA, Tukey Test) All pairwise Multiple Comparison.

Example L

Figure 2:
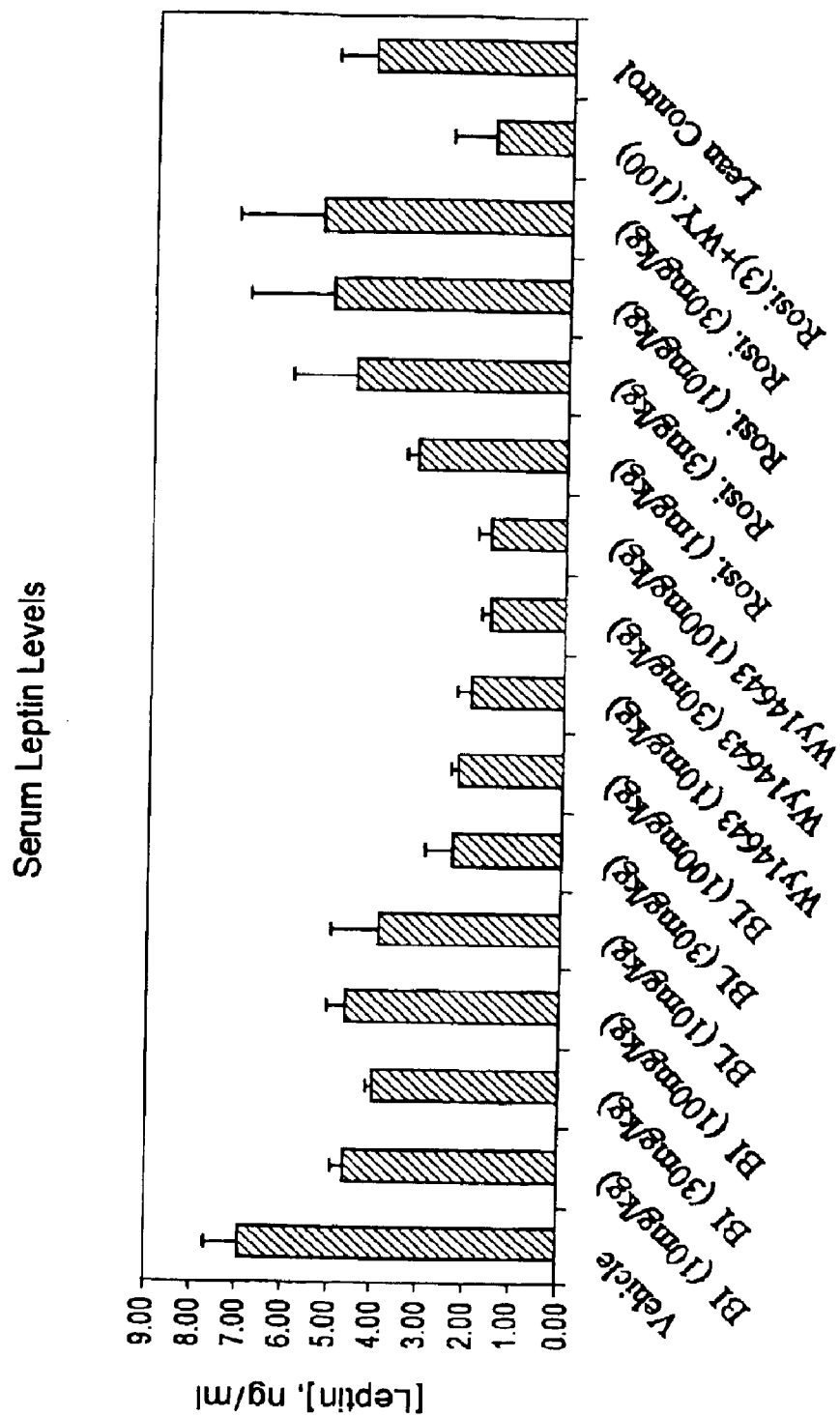
FIG. 2: Serum leptin levels in high fat-fed C57B1/6J mice receiving vehicle (negative control), Compound BI, Compound BL, Wy14643 or rosiglitazone.

Oral BI and BL Lower Circulating Triglycerides, Free Fatty acids, Insulin and Leptin in High Fat-fed C57B1/6J Mice The high fat-fed mouse is a model for the hypertriglyceridemia and high circulating fatty acid levels, and the insulin and leptin resistance that are found in people at risk for and with obesity, diabetes, cardiovascular disease and other disorders. Male C57B1/6J mice, approximately 8 weeks of age, were randomly assigned into groups of 6 animals. They were maintained under controlled temperature (23° C.), relative humidity (50±5%) and light (7:00–19:00), and allowed free access to food and water ad libitum. Mice were fed a high-fat diet (diet number D12451, containing 45% of calories as fat (Research Diets, New Brunswick, N.J.)) for 6 weeks. After the 6 weeks, groups of mice received either vehicle (hydroxymethylcellulose), BI, BL, Wy14,643 or rosiglitazone by oral gavage at the indicated doses for an additional 4 weeks while continuing on the high-fat diet. Plasma chemistries (Anilytics, Inc., Gaithersburg, Md.) were assayed after 2 weeks of drug treatments. Plasma serum insulin (FIG. 1) and leptin (FIG. 2) were measured by an electrochemiluminescent immunoassay (Origen Analyzer, Igen, Inc., Gaithersburg, Md.) after 4 weeks of drug treatments.

BI and BL were effective at lowering serum triglycerides and free fatty acids as well as insulin and leptin serum levels. Serum values from mice from the same cohort ("lean controls") that were maintained on regular lab chow (Formulab Diet 5008, Quality Lab Products, Elkridge, Md.) are shown for comparison.

TABLE 16

| | Triglycerides (mg/dL) | Free Fatty Acids (umol/L) |
|---|---|---|
| Vehicle | 135 ± 40.1 | 1686 ± 359.3 |
| BI (10 mg/kg) | 68.8 ± 5.7 | 1227 ± 193.7 |
| BI (30 mg/kg) | 66.5 ± 14.7 | 1292 ± 231.4 |
| BI (100 mg/kg) | 37.4 ± 8.3 | 992.8 ± 172.1 |
| BL (10 mg/kg) | 80 ± 12.2 | 1571.8 ± 100.9 |
| BL (30 mg/kg) | 66.4 ± 13.7 | 1413.2 ± 228.7 |
| BL (100 mg/kg) | 41 ± 5.6 | 1133.5 ± 132.7 |
| Rosiglitazone (1 mg/kg) | 76.6 ± 16.5 | 1537 ± 256.3 |
| Rosiglitazone (3 mg/kg) | 103.2 ± 10.8 | 1833.2 ± 169.8 |
| Rosiglitazone (10 mg/kg) | 129.5 ± 48.7 | 1810.3 ± 595 |
| Rosiglitazone (100 mg/kg) | 88 ± 7.2 | 1568.5 ± 197 |
| Wy14643 (10 mg/kg) | 70.6 ± 10.8 | 1512.2 ± 172.9 |
| Wy14643 (30 mg/kg) | 88 ± 12.5 | 1676 ± 237 |
| Wy14643 (100 mg/kg) | 88.4 ± 18.8 | 1839.8 ± 154.8 |
| Rosi (3 mg/kg) + Wy14643 (100 mg/kg) | 54.3 ± 10.5 | 1649.7 ± 260.5 |

Example M

Oral BI Lower Circulating Triglycerides, Free Fatty acids, Insulin and Leptin in High Fat-fed Sprague Dawley Rats The high fat-fed rat is a model for insulin and leptin resistance. Sprague-Dawley rats have an intact leptin system and respond to a high fat diet with hyperinsulinemia due to a downregulation of the normal insulin response in peripheral tissues such as liver, adipose tissue and muscle.

Male Sprague-Dawley rats, approximately 17 weeks of age, were obtained from Jackson Labs (Bar Harbor, Me.) and randomly assigned into groups of 5–7 animals; the body weights were similar between groups. All animals were maintained in a temperature-controlled (25° C.) facility with a strict 12 h light/dark cycle and were given free access to water and food. Rats were fed a high-fat diet (diet number D12451 (containing 45% of calories as fat), Research Diets, New Brunswick, N.J.) for one month prior to drug treatment.

Groups of 6 Sprague-Dawley rats were treated with a single daily dose of vehicle (hydroxymethylcellulose), BI (10, 30 and 100 mg/kg), or rosiglitazone (3 mg/kg) for 6 weeks while maintaining the high-fat diet. At the indicated time points, blood samples (~100 μl) were obtained via the tail vein for serum chemistry analysis.

BI (30 mg/kg) reduced serum insulin, triglycerides; BI at all doses reduced free fatty acids.

TABLE 17

Effect of BI and rosiglitazone on serum glucose, insulin, triglycerides and free fatty acids in high-fat fed Sprague-Dawley rats

| Group | Glucose (mg/dL) | Insulin (ng/ml) | Triglycerides (mg/dL) | Free Fatty Acids (μMol/L) |
|---|---|---|---|---|
| Lean | 123.8 ± 7.0 | 0.72 ± 0.1 | 179.0 ± 72.3 | 743.5 ± 57.4 |
| Vehicle | 122.3 ± 5.9 | 1.78 ± 0.3 | 200.7 ± 39.2 | 942.5 ± 181.0 |
| BI-10 | 117.3 ± 8.8 | 2.18 ± 0.9 | 183.7 ± 58.4 | 923.7 ± 161.3 |
| BI-30 | 127.3 ± 22.2 | 1.46 ± 0.2 | 129.3 ± 20.0 | 738.7 ± 50.0 |
| BI-100 | 19.3 ± 3.5 | 1.79 ± 0.2 | 171.7 ± 33.1 | 725.7 ± 87.5 |
| RG-3 | 119.8 ± 5.4 | 1.57 ± 0.2 | 134.2 ± 15.2 | 758.8 ± 61.0 |

What is claimed is:

1. A compound of the formula:

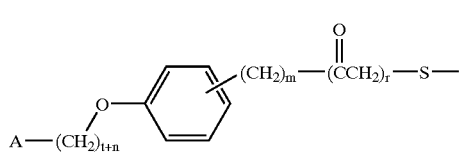

II wherein n is 1 or 2;

t is 0 or 1;

m is 0 and r is 1, or m is 1 and r is 0;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are mono-substituted by methyl or ethyl;

Z is

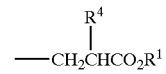

$R^1$ is hydrogen or alkyl having from 1 to 7 carbon atoms;

$R^4$ is hydrogen; —NHCOOC(CH$_3$)$_3$; —NHCH$_3$; or —NHCH$_2$CH$_3$;

or when $R^1$ is hydrogen, a pharmaceutically acceptable salt of the compound.

2. The compound or salt of claim 1, wherein A is cycloalkyl having from 3 to 6 ring carbon atoms wherein the cycloalkyl is unsubstituted or one or both of the ring carbons adjacent to the remainder of the compound of formula II are mono-substituted by methyl or ethyl.

3. The compound or salt of claim 1, wherein A is phenyl, unsubstituted or substituted by 1 or 2 groups selected from: fluoro, alkyl having 1 or 2 carbon atoms, perfluoromethyl, alkoxy having 1 or 2 carbon atoms, and perfluoromethoxy.

4. The compound of claim 3, represented by the formula:

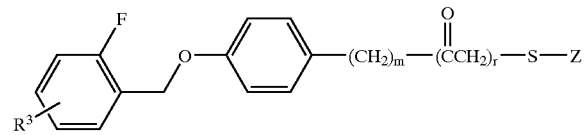

IIA wherein m is 0 or 1;

r is 0 or 1;

Z is

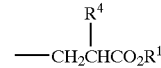

$R^1$ is hydrogen or alkyl having from 1 to 7 carbon atoms;

$R^4$ is hydrogen; —NHCOOC(CH$_3$)$_3$; —NHCH$_3$; or —NHCH$_2$CH$_3$;

$R^3$ is hydrogen or halo;

or when $R^1$ is hydrogen, a pharmaceutically acceptable salt of the compound.

5. The compound or salt of claim 4, wherein $R^1$ is hydrogen or ethyl.

6. The compound or salt of claim 5, wherein the compound is 3-[(4-(2-fluorobenzyloxy)phenyl)-methylthio]propionic acid.

7. The compound or salt of claim 5, wherein the compound is 3-[(4-(2,6-difluorobenzyloxy)phenyl)-methylthio]propionic acid.

8. The compound or salt of claim 5, wherein the compound is (2RS)2-(N-Boc)-3-[2-(4-(2,6-difluorobenzyloxy)phenyl)-2-oxoethyl]thiopropionic acid.

9. A compound of the formula:

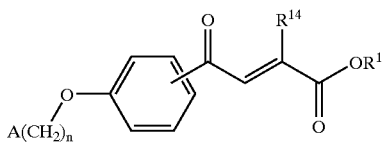
V' wherein n is 1 or 2;

$R^1$ is hydrogen or alkyl having from 1 to 7 carbon atoms;

$R^{14}$ is hydroxy or hydrogen; and

A is
cycloalkyl having from 3 to 6 ring carbon atoms wherein the cycloalkyl is unsubstituted or one or two ring carbons are independently mono-substituted by methyl or ethyl;

or a pharmaceutically acceptable salt of the compound.

10. The compound of claim 9, represented by the formula:

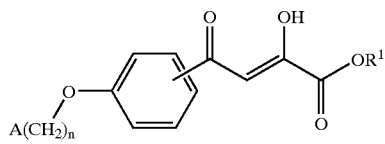
V wherein n is 1 or 2;

$R^1$ is hydrogen or alkyl having from 1 to 7 carbon atoms;

A is
cycloalkyl having from 3 to 6 ring carbon atoms wherein the cycloalkyl is unsubstituted or one or two ring carbons are independently mono-substituted by methyl or ethyl;

or a pharmaceutically acceptable salt of the compound.

11. A compound, ethyl 2-hydroxy-4-oxo-4-(4-(2,6-difluorobenzyloxy)phenyl)but-2-enoate, or a pharmaceutically acceptable salt thereof.

12. A compound, 4-(3-(2,6-Dimethylbenzyloxy)phenyl)-4-oxo-2-butenoic acid, or a pharmaceutically acceptable salt thereof.

13. A compound of the formula:

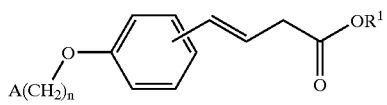
XCI wherein n is 1 or 2;

$R^1$ is hydrogen or alkyl having from 1 to 3 carbon atoms; and

A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl;

or a pharmaceutically acceptable salt of the compound.

14. The compound or salt of claim 13, wherein the compound is 4-(3-(2,6-Dimethylbenzyloxy)phenyl)-3-butenoic acid.

15. A compound of the formula:

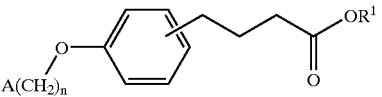
CXVI wherein n is 1 or 2;

$R^1$ is hydrogen or alkyl having from 1 to 3 carbon atoms; and

A is phenyl substituted by 1 or 2 groups selected from halo, alkyl having 1 or 2 carbon atoms, perfluoromethyl, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl;

or a pharmaceutically acceptable salt of the compound.

16. The compound or salt of claim 15, wherein the compound is 4-(3-(2,6-Dimethylbenzyloxy)phenyl)butyric acid.

17. A compound of the formula:

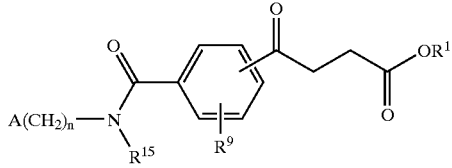
CXVII wherein n is 0, 1 or 2;

$R^1$ is hydrogen or alkyl having from 1 to 3 carbon atoms;

$R^{15}$ is hydrogen or alkyl having from 1 to 3 carbon atoms;

$R^9$ is hydrogen, halo, hydroxy, or alkoxy having from 1 to 3 carbon atoms;

A is phenyl, unsubstituted or substituted by 1 or 2 groups selected from halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl;

or a pharmaceutically acceptable salt of the compound.

18. The compound or salt of claim 17, wherein the compound is 4-{3-[((4-Trifluoromethylbenzylamino)-carbonyl)-4-methoxy]phenyl}-4-oxobutyric acid.

19. The compound or salt of claim 17, wherein the compound is 4-{3-[((2,6-Dimethyllbenzylamino)-carbonyl)-4-methoxy]phenyl}-4-oxobutyric acid.

* * * * *